(12) United States Patent
Han et al.

(10) Patent No.: US 10,106,813 B2
(45) Date of Patent: Oct. 23, 2018

(54) DROUGHT-TOLERANCE IN PLANTS

(71) Applicant: Board of Trustees of Michigan State University, East Lansing, MI (US)

(72) Inventors: Kyung-Hwan Han, Okemos, MI (US); Won-Chan Kim, Okemos, MI (US); Joo-Yeol Kim, Lansing, MI (US); Jae-Heung Ko, Suwon (KR)

(73) Assignee: Board of Trustees of Michigan State University, East Lansing, MI (US)

( * ) Notice: Subject to any disclaimer, the term of this patent is extended or adjusted under 35 U.S.C. 154(b) by 484 days.

(21) Appl. No.: 14/617,061

(22) Filed: Feb. 9, 2015

(65) Prior Publication Data

US 2015/0225737 A1    Aug. 13, 2015

Related U.S. Application Data

(60) Provisional application No. 61/937,865, filed on Feb. 10, 2014.

(51) Int. Cl.
*C12N 15/82* (2006.01)
*C12N 15/113* (2010.01)

(52) U.S. Cl.
CPC ........ *C12N 15/8273* (2013.01); *C12N 15/113* (2013.01); *C12N 15/8237* (2013.01)

(58) Field of Classification Search
None
See application file for complete search history.

(56) References Cited

U.S. PATENT DOCUMENTS

| 7,196,245 | B2 | 3/2007 | Jiang et al. |
| 7,977,535 | B2* | 7/2011 | Han .................. C12N 15/8273 435/320.1 |
| 9,371,539 | B2 | 6/2016 | Han et al. |
| 2001/0047092 | A1* | 11/2001 | Bruce ................ C12N 15/8216 536/24.1 |
| 2003/0082724 | A1 | 5/2003 | Flinn et al. |
| 2004/0031072 | A1 | 2/2004 | La Rosa |
| 2006/0107345 | A1 | 5/2006 | Alexandrov et al. |
| 2007/0044171 | A1 | 2/2007 | Kovalic et al. |
| 2012/0011615 | A1 | 1/2012 | Han |
| 2012/0084885 | A1* | 4/2012 | Alexandrov ....... C12N 15/8216 800/298 |
| 2015/0267220 | A1* | 9/2015 | Brugiere ............. C07K 14/415 800/287 |

(Continued)

FOREIGN PATENT DOCUMENTS

WO   WO-2004031349 A2   4/2004
WO   WO-2004076638 A2   9/2004

(Continued)

OTHER PUBLICATIONS

GenBank: CP002685.1. *Arabidopsis thaliana* chromosome 2 sequence. Published Jun. 13, 2011. pp. 1. Available at https://www.ncbi.nlm.nih.gov/nuccore/330250293?sat=17&satkey=23262953.*

(Continued)

*Primary Examiner* — Ashley K Buran
(74) *Attorney, Agent, or Firm* — Schwegman Lundberg & Woessner, P.A.

(57) ABSTRACT

Drought-inducible plant promoters are described herein that are useful for expressing drought tolerance factors in plants.

22 Claims, 15 Drawing Sheets
(7 of 15 Drawing Sheet(s) Filed in Color)

Specification includes a Sequence Listing.

(56) References Cited

U.S. PATENT DOCUMENTS

2016/0348128 A1 12/2016 Han et al.

FOREIGN PATENT DOCUMENTS

| WO | WO-2008/008396 A2 | 1/2008 |
|---|---|---|
| WO | WO-2008008396 A3 | 1/2008 |
| WO | WO-2013056000 A1 | 4/2013 |

OTHER PUBLICATIONS

Roychoudhury et al. The promoter-elements of some abiotic stress-inducible genes from cereals interact with a nuclear protein from tobacco. Biologia Plantarum. 2009. 53(3): 583-587.*
Hou et al. Construction of Stress Responsive Synthetic Promoters and Analysis of Their Activity in Transgenic *Arabidopsis thaliana*. Plant Molecular Biology Reporter. 2012. 30(6): 1496-1506.*
Rushton et al. Synthetic plant promoters containing defined regulatory elements provide novel insights into pathogen- and wound-induced signaling. The Plant Cell. 2002. 14: 749-762.*
"Application Serial No. 2,658,391, Voluntary Amendment filed Dec. 6, 2016", 8 pgs.
"Application Serial No. 2,658,391, Voluntary Amendment filed Dec. 16, 2016", 7 pgs.
"European Application Serial No. 13181042.6, Office Action dated Dec. 5, 2016", 16 pgs.
"Indian Application Serial No. 731/CHENP/2009, Office Action dated Nov. 16, 2016".
"Indian Application Serial No. 731/CHENP/2009, Written Submissions Filed Jan. 13, 2017", 13 pgs.
"SubName: Full=Putative uncharacterized protein AT4g27030; SubName: Full=Putative uncharacterized protein F10M23.370", Database UniProt, (May 1, 2000), 2 pgs.
"U.S. Appl. No. 11/484,947, Examiner Interview Summary dated Feb. 8, 2011", 3 pgs.
"U.S. Appl. No. 11/484,947, Final Office Action dated Jan. 19, 2011", 6 pgs.
"U.S. Appl. No. 11/484,947, Final Office Action dated Jun. 1, 2009", 11 pgs.
"U.S. Appl. No. 11/484,947, Non Final Office Action dated May 26, 2010", 8 pgs.
"U.S. Appl. No. 11/484,947, Non Final Office Action dated Aug. 6, 2008", 14 pgs.
"U.S. Appl. No. 11/484,947, Notice of Allowance dated Mar. 2, 2011", 5 pgs.
"U.S. Appl. No. 11/484,947, Notice of Non-Compliant Amendment dated Jan. 15, 2009", 4 pgs.
"U.S. Appl. No. 11/484,947, Notice of Non-Compliant Amendment dated Jan. 21, 2010", 3 pgs.
"U.S. Appl. No. 11/484,947, Preliminary Amendment filed Apr. 26, 2007", 3 pgs.
"U.S. Appl. No. 11/484,947, Preliminary Amendment filed Dec. 6, 2006", 4 pgs.
"U.S. Appl. No. 11/484,947, Response filed Feb. 11, 2009 to Notice of Non-Compliant Amendment dated Jan. 15, 2009", 9 pgs.
"U.S. Appl. No. 11/484,947, Response filed Feb. 14, 2011 to Final Office Action dated Jan. 19, 2011", 8 pgs.
"U.S. Appl. No. 11/484,947, Response Filed Feb. 16, 2010 to Notice of Non-Compliant Amendment dated Jan. 21, 2010", 16 pgs.
"U.S. Appl. No. 11/484,947, Response filed Apr. 2, 2008 to Restriction Requirement dated Mar. 5, 2008", 3 pgs.
"U.S. Appl. No. 11/484,947, Response filed Aug. 24, 2010 to Non Final Office Action dated May 26, 2010", 9 pgs.
"U.S. Appl. No. 11/484,947, Response filed Nov. 2, 2009 to Final Office Action dated Jun. 1, 2009", 16 pgs.
"U.S. Appl. No. 11/484,947, Response filed Nov. 6, 2008 to Non Final Office Action dated Aug. 6, 2008", 15 pgs.
"U.S. Appl. No. 11/484,947, Restriction Requirement dated Mar. 5, 2008", 9 pgs.
"U.S. Appl. No. 13/180,953, Advisory Action dated Apr. 17, 2014", 3 pgs.
"U.S. Appl. No. 13/180,953, Advisory Action dated Apr. 26, 2013", 3 pgs.
"U.S. Appl. No. 13/180,953, Final Office Action dated Jan. 28, 2013", 15 pgs.
"U.S. Appl. No. 13/180,953, Final Office Action dated Feb. 3, 2014", 14 pgs.
"U.S. Appl. No. 13/180,953, Non Final Office Action dated Jun. 1, 2015", 17 pgs.
"U.S. Appl. No. 13/180,953, Non Final Office Action dated Jul. 6, 2012", 19 pgs.
"U.S. Appl. No. 13/180,953, Non Final Office Action dated Jul. 31, 2013", 14 pgs.
"U.S. Appl. No. 13/180,953, Response filed Feb. 1, 2012 to Restriction Requirement dated Dec. 1, 2011", 7 pgs.
"U.S. Appl. No. 13/180,953, Response filed Mar. 27, 2013 to Final Office Action dated Jan. 28, 2013", 11 pgs.
"U.S. Appl. No. 13/180,953, Response filed Apr. 3, 2014 to Final Office Action dated Feb. 3, 2014", 12 pgs.
"U.S. Appl. No. 13/180,953, Response filed Oct. 4, 2012 to Non Final Office Action dated Jul. 6, 2012", 17 pgs.
"U.S. Appl. No. 13/180,953, Response filed Oct. 29, 2013 to Non Final Office Action dated Jul. 31, 2013", 15 pgs.
"U.S. Appl. No. 13/180,953, Restriction Requirement dated Dec. 1, 2011", 8 pgs.
"Australian Application Serial No. 2007272993, Response filed Nov. 11, 2011", 7 pgs.
"Australian Application Serial No. 2007272993, Response filed Oct. 26, 2011", 17 pgs.
"Australian Application Serial No. 2007272993, Examiner's First Report dated Oct. 27, 2010", 4 pgs.
"Australian Application Serial No. 2007272993, Response filed Oct. 28, 2011 to Examiner's First Report dated Oct. 27, 2010", 17 pgs.
"Basic Local Alignment Search Tool", SEQ ID No. 1 aligned with SEQ ID No. 144, (2015), 2 pgs.
"Canadian Application Serial No. 2,658,391, Amendment filed Apr. 14, 2009", 5 pgs.
"Canadian Application Serial No. 2,658,391, Office Action dated Jan. 9, 2015", 5 pgs.
"Canadian Application Serial No. 2,658,391, Office Action dated Oct. 6, 2010", 5 pgs.
"Canadian Application Serial No. 2,658,391, Office Action dated Dec. 10, 2013", 4 pgs.
"Canadian Application Serial No. 2,658,391, Response filed May 21, 2013 to Office Action dated Nov. 22, 2012", 7 pgs.
"Canadian Application Serial No. 2,658,391, Response filed Jun. 10, 2014", 18 pgs.
"Canadian Application Serial No. 2,658,391, Voluntary Amendment filed Jul. 18, 2014", 9 pgs.
"Canadian Application Serial No. 2658391, Office Action dated Nov. 22, 2012", 4 pgs.
"Database UniProt", "SubName: Full=Putative RING zinc finger protein; SubName: Full=T23015.13;", XP002591597, retrieved from EBI accession No. UNIPROT:Q9SI09 Database accession No. Q9SI09, (2000), 5 pgs.
"European Application Serial No. 07810352.0, Examination Notification Art. 94(3) dated Mar. 11, 2013", 5 pgs.
"European Application Serial No. 07810352.0, Examination Notification Art. 94(3) dated Oct. 18, 2013", 8 pgs.
"European Application Serial No. 07810352.0, Extended European Search Report dated Aug. 4, 2010", 10 pgs.
"European Application Serial No. 07810352.0, Office Action dated Jun. 9, 2009", 3 pgs.
"European Application Serial No. 07810352.0, Office Action dated Aug. 22, 2011", 4 pgs.
"European Application Serial No. 07810352.0, Office Action dated Aug. 23, 2010", 1 pg.

(56) References Cited

OTHER PUBLICATIONS

"European Application Serial No. 07810352.0, Response filed Feb. 13, 2014 to Examination Notification Art. 94(3) dated Oct. 18, 2013", 13 pgs.
"European Application Serial No. 07810352.0, Response filed Mar. 2, 2011 to Office Action dated Aug. 23, 2010", 10 pgs.
"European Application Serial No. 07810352.0, Response filed Jun. 21, 2013 to Examination Notification Art. 94(3) dated Mar. 11, 2013".
"European Application Serial No. 07810352.0, Response filed Jun. 25, 2009 to Office Action dated Jun. 9, 2009", 1 pg.
"European Application Serial No. 07810352.0, Response filed Jul. 11, 2013", 18 pgs.
"European Application Serial No. 07810352.0, Response filed Nov. 29, 2011 to Office Action dated Aug. 22, 2011", 8 pgs.
"European Application Serial No. 07810352.0, Summons to Attend Oral Proceedings mailed Jul. 9, 2015", 8 pgs.
"European Application Serial No. 13181042.6, Examination Notification Art. 94(3) dated Jul. 1, 2015", 9 pgs.
"European Application Serial No. 13181042.6, Extended European Search Report dated Oct. 18, 2013", 10 pgs.
"European Application Serial No. 13181042.6, Response filed May 7, 2014 to Extended European Search Report dated Oct. 18, 2013", 24 pgs.
"Indian Application Serial No. 731/CHENP/2009, First Examiner Report dated Dec. 19, 2013", 2 pgs.
"Indian Application Serial No. 731/CHENP/2009, Response filed May 30, 2014 to First Examiner Report dated Dec. 19, 2013", 37 pgs.
"Indian Application Serial No. 731/CHENP/2009, Response filed Dec. 16, 2014", 19 pgs.
"Indian Application Serial No. 731/CHENP/2009, Second Examiner Report dated Nov. 13, 2014", 2 pgs.
"International Application Serial No. PCT/US2007/015823, International Preliminary Report on Patentability dated Jan. 13, 2009", 6 pgs.
"International Application Serial No. PCT/US2007/015823, International Search Report dated Sep. 29, 2008", 4 pgs.
"International Application Serial No. PCT/US2007/015823, Written Opinion dated Sep. 29, 2008", 5 pgs.
"Putative RING zinc Finger protein-like protein, Thellungiella halophila", Genbank Accession No. Q8S2S3, (2002), 4 pgs.
"RING H-s finger protein, Poncirus trifoliata", Genbank Accession No. Q20D22, [Online]. Retrieved from the Internet: <URL: https://www.lens.org/lens/patent/AU_2007_272993_B2/fulltext>, 56 pgs.
"SubName:Full=Putative RING zinc finger protein; SubName: Full=T23015.13.", retrieved from EBI accession No. UNIPROT:Q9SI09 Database accession No. Q9SI09, Database UniProt [Online], (May 1, 2000, Last modified Mar. 6, 2013), 4 pgs.
Borden, K. L. B., et al., "The RING finger domain: a recent example of a sequence-structure family", Current Opinion in Structural Biology, 6(3), (1996), 395-401.
Harb, Amal, et al., "Molecular and Physiological Analysis of Drought Stress in *Arabidopsis* Reveals Early Responses Leading to Acclimation in Plant Growth", Plant Physiology 154(3), (2010), 1254-1271.
Hill, M. A, et al., "Functional Analysis of Conserved Histidines in ADP-Glucose Pyrophosphorylase from *Escherichia coli*", Biochem Biophys Res Commun., 244(2), (Mar. 17, 1998), 573-577.
Jiang, C., et al., "GenBank Accession EAI06997, Sequence 375 from patent U.S. Pat. No. 7,196,245", (Apr. 11, 2007), 2 pgs.
Ko, et al., "Ectopic expression of MYB46 identifies transcriptional regulatory genes involved in secondary wall biosynthesis in *Arabidopsis*", The Plant Journal, vol. 60, No. 4, (Nov. 1, 2009), 649-665.
Ko, J-H, et al., "Upregulation of an *Arabidopsis* RING-H2 Gene, XERICO, confers drought tolerance through increased abscisic acid biosynthesis", Plant Journal, 47(3), (2006), 343-355.

Matzke, Antonius J.M., et al., "Position effects and epigenetic silencing of plant transgenes", Current Opinion in Plant Biology, 1(2), (1998), 142-148.
Matzke, Marjori A., et al., "How and Why Do Plants Inactivate Homologous (Trans)genes?", Plant Physiol. 107, (1995), 679-685.
Pobjecky, N., et al., "Expression of the beta-glucuronidase gene under the control of the CaMV 35s promoter in Schizosaccharomyces pombe.",Mol Gen Genet. Jan. 1990;220(2):314-316., (1990), 314-316.
Rhoads, David M, et al., "Regulation of the Cyanide-resistant Alternative Oxidase of Plant Mitochondria", Identification of the cysteine residue involved in alpha-keto acid stimulation and intersubunit disulfide bond formation. J. Biol. Chem., 273(46), (Nov. 13, 1998), 30750-30756.
Sahin-Cevik, M., et al., "Isolation and characterization of a novel RING-H2 finger gene induced in response to cold and drought in the interfertile Citrus relative Poncirus trifoliata", Physiologia Plantarum,126(1), (2006), 153-161.
Verslues, Paul, et al., "Methods and concepts in quantifying resistance to drought, salt and freezing, abiotic stresses that affect plant water status", The Plant Journal 45(4), (2006), 523-539.
Whisstock, J C, et al., "Prediction of protein function from protein sequence and structure", Q Rev Biophys. 36(3), (2003), 307-340.
Yamada, K., et al., "GenBank Accession AF339689,*Arabidopsis thaliana* putative RING zinc finger protein (At2g04240) mRNA, complete cds.", (Sep. 18, 2002), 2 pgs.
Zeng, De-Er, et al., "Overexpression of *Arabidopsis* XERICO gene confers enhanced drought and salt stress tolerance in rice (*Oryza ativa* L.)", J. Plant Biochem. Biotechnol. 24(1):, (Aug. 23, 2013), 56-64.
Zhang, James, et al., "Overexpression Analysis of Plant Transcription Factors", Curr Opin Plant Biol 6, (2003), 430-440.
"U.S. Appl. No. 13/180,953, Final Office Action dated Nov. 4, 2015", 20 pgs.
"U.S. Appl. No. 13/180,953, Notice of Allowability dated Mar. 18, 2016", 7 pgs.
"U.S. Appl. No. 13/180,953, Notice of Allowance dated Feb. 23, 2016", 11 pgs.
"U.S. Appl. No. 13/180,953, PTO Response to Rule 312 Communication dated May 13, 2016", 2 pgs.
"U.S. Appl. No. 13/180,953, Response filed Sep. 1, 2015 to Non Final Office Action dated Jun. 1, 2015", 15 pgs.
"U.S. Appl. No. 13/180,953, Response filed Jan. 20. 2016 to Final Office Action dated Nov. 4, 2015", 18 pgs.
"U.S. Appl. No. 15/163,033, Preliminary Amendment filed May 25, 2015", 7 pgs.
"Canadian Application Serial No. 2,658,391, Office Action dated Jan. 29, 2016", 5 pgs.
"Canadian Application Serial No. 2,658,391, Response filed Jul. 9, 2015 to Office Action dated Jan. 9, 2015", 15 pgs.
"Canadian Application Serial No. 2,658,391, Response filed Jul. 27, 2016 to Office Action dated Jan. 29, 2016", 18 pgs.
"European Application Serial No. 07810352.0, Written Decision to Refuse dated Mar. 11, 2016", 14 pgs.
"European Application Serial No. 07810352.0, Written Submission filed Dec. 15, 2015", 24 pgs.
"European Application Serial No. 13181042.6, Response filed Oct. 29, 2015 to Examination Notification Art. 94(3) dated Jul. 1, 2015", 22 pgs.
"European Application Serial No. 13181042.6, Summons to Attend Oral Proceedings mailed Jun. 14, 2016", 9 pgs.
"European Application Serial No. 13181042.6, Written Submissions filed on Oct. 14, 2016 in preparation for Oral Proceedings", 15 pgs.
Ko, Jae-Heung, et al., "Upregulation of an *Arabidopsis* RING-H2 gene XERICO, confers drought tolerance through increased abscisic add biosynthesis", *The Plant Journal*, 47, (2006), 343-355.
"U.S. Appl. No. 15/163,033, Supplemental Preliminary Amendment filed Jun. 12, 2017", 7 pgs.
"European Application Serial No. 07810352.0, Summons to oral proceedings pursuant to Rule 115(1) EPC mailed on Aug. 29, 2017", 1 pg.

* cited by examiner

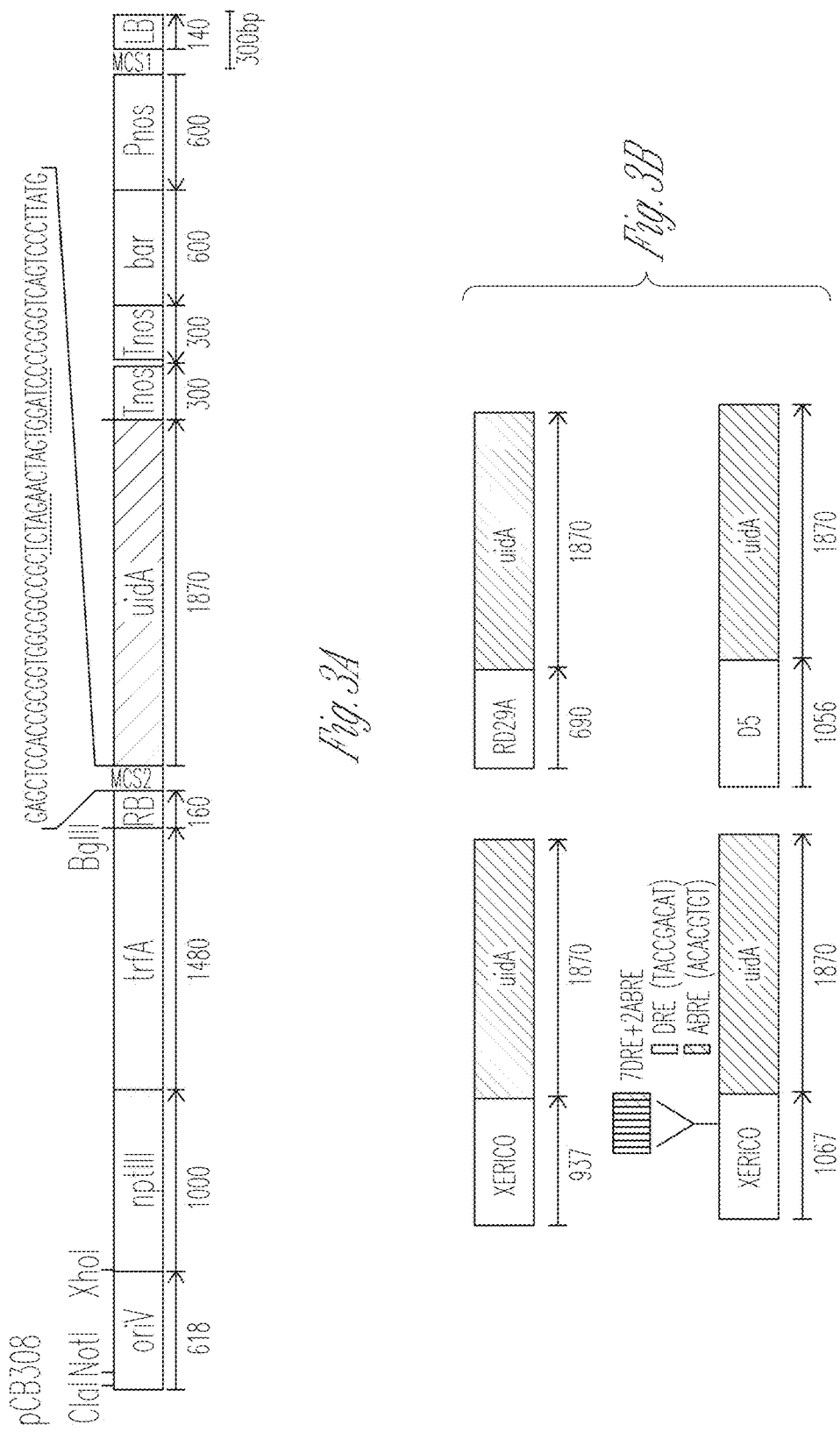

>ProA: CaMV 35S promoter
AAGCTTGCATGCCTGCAGGTCCCGGATTAGCCTTTTCAATTTCAGAAAGAGGACCTATCCAGATGGTT
AGAGAGGCTTACGCAGCAGGTCTCATCAAGACGATCATTTCCAGATGGCATATTCCAGATACC
TCCCAGAAGATGAAAGATGCAGTCAAAAGATTCAGGACTAACTCAAGGACACAGAGAATATAT
TTCCAAGATCCAGAAGTTCATATTCAGATGGACGATTCAAGGCCTTGCTACAACCCAAGGCAAGTAAA
GAGATTGGAGTCTCAAAAGGTAGTGTCCCACTGAATCTGAATCAAGATTCAATAGAGGGA
CCTAACAGACTCGGCGTAAGACTGGGCGACAAGGTCCATAGAGTTCCTTCGATCATTGACAAGAAGA
TAATCCTTGGTCATGCTGGTAGGATCCCATCTCCTCTGAATCAAATCTCTCTCTCAGGI
TATTCTGTCTCTTAATTGTGAAGACACTTTCAACAACCGATAATGTGGAAAATCCTTGGTCATGCCAGC
GAAAGCCATGGTTGAGATGGCACCAGCTGGAGGTGGCCCAAAGATGGGTCCTTCAAATGCCACTGGTAAAG
GTGGAAAAAGAAGACGTTCCAACCTCAACAGTCTTCAAGGACGTTCCAGAAGCAGCCACTGCGCTGAAG
GGATGACGCAATCCACATCTCAACAGATGTTGAGCAGCCTCGCAGAGCATCTCCACTGAGGTAAG
GAACACGCGGGGGACTCTAGAGGATCC >XERICO(At2G04240)
ACAACATCATCTACCGACAAGATTGGAATCAACAAGTAGATCAACAAGTAGTGAAGATGGGTCATCAAGTCTTC
CTGGTCCATCGGATGGATTCCTTATTGTATTGTGTTATTAGTGTTATACGCCTTATACGCTTATCGTGTCAAGC
ATTGTAAGATCATTCTTGCCATGTAGAATCAGTCGCCGTCTGGCCGATTCGATCCTTTGCTGCGC
GTATTCAGAGAATTCAGCAACTCAGAGTCATTGATTTGCCGGTCCGACAGAGAAGTACTTG
AGGAGTCAGGAACCGGATTGTGTTTGACGATTCAGAATTCAAGGGATTCAGAGATCATCGCCGTCAGGAN
CAGTGTTCAGTGTTGTGGAAGAATTGTGTGGGATTCAGAATTGGATCATCGACTGTCAAGTCAGGGCATTGTT
CACAGATCATGCCGAGAAGACCATCAGCTTCTTCTAATGTTGGTGACACTGGACTTGGGACTGCCTCGAAA
TTGTTGTGCAGTGTGTTTGTGTGTACGCTA
ATTGAAGTGTCGTGTTGTGTGTACGCTA

SEQUENCE LISTING

```
<160> NUMBER OF SEQ ID NOS: 21

<210> SEQ ID NO 1
<211> LENGTH: 1072
<212> TYPE: DNA
<213> ORGANISM: Arabidopsis thaliana

<400> SEQUENCE: 1
tgttggggca aaattgatat gtaagttcgt ctatgggagg gaattaagtt tccgctgagt      60
aataaacaaa caagtgcaaa cctaggaatt caacaccaat gtaattttt ataattttgt     120 aggactcttt aatagtcaag tcagtattta aaccacaaga gtcggtcaga aaccagaaaa     180
actagaaaca agttatgtca gttctaagaa gagagatgtg caatgtattc ggcaatcggg     240
tatatcatct aacattttag ccagtgaaaa aagagaaaga tatgaggatt tttccattgt     300
tcagtaagct aagagaagac agtttcatta aagagtcgaa tagaatggat attctcatga     360
aactgagaag gttaagtttt tttggggaat actttgcatg cctttatata ggtgaagagt     420
catgttgcat agctccgagg catttcagct tataagtatc catgtctcga ctcatatgat     480
gaatggactt gatgaaggga ctaggcaatc gatcgtcagt gcgggtgaat tttgacgtct     540
tgagtccatc cgaccattca aaagaaagta ttcttcttac cacgtagcat gtgactttac     600
ctagagttcg tggagcacaa gtagaacaaa taggattatg cctaaacacc tttagaacta     660
```

| | |
|---|---|
| gaccaaaggt caaaaactat caaaacaagt tttttacgct acatggttta cataaaaaaa | 720 |
| ttaagtgata cactcaatga tgaataacaa tattaaccca aacaaatttg atatcaaaac | 780 |
| acagtataac caaatcaaa accgtagtgg aactaaacta gattatataa tatgcctcca | 840 |
| taaatactcg gattttccac gtgaattgga ctaatcatta attaggaaga acggaatcag | 900 |
| aataaatatg tctactcaac tttcggtatg gtggtggtag aaaagagaat aagattcaaa | 960 |
| gcatattacg aattattgcc atatgggatc atatctaaca caaatttaaa agaacactct | 1020 |
| actactacag tacaaaattg tatatatata aacacctgaa agattttaat ta | 1072 |

<210> SEQ ID NO 2
<211> LENGTH: 1085
<212> TYPE: DNA
<213> ORGANISM: Arabidopsis thaliana

<400> SEQUENCE: 2

| | |
|---|---|
| caccttgaaa cattaactcc gtaattaatt tagtcttgca atttttcata aattgtttat | 60 |
| atatgtcgta acacaaaatt tgcgaacggt taataacttt actagataaa acctctctaa | 120 |
| ataggtagat gtgaaaaata aataaatttt tgttttaata aattttttcaa atgataatct | 180 |
| atatatattt tatttaatat atattttcta aaaccaaatt tcaatcttac cttttctaaa | 240 |
| accatattgt taaaaactaa agaaaaagtt ggaccaagca aagcctctcg gtaaatgtgg | 300 |
| taaataaata gaacgatata actgagaaga agaaaataaa acaaaattaa gaaaataaaa | 360 |
| agataaacat atttaagtta caatatttaa aaatattaaa acacttcttt ttaagaacaa | 420 |
| aatggggaat tttatttatg ttttgaatag atcaacaatt attaatagaa tgagtttagt | 480 |
| ttaatatatt aaatataaaa aattgaatat ataacaatt gttttatgta tatattttt | 540 |
| ttttgatagg gttaaggatt tttttctatt tttgttttta aatgtaataa aatttgaaac | 600 |
| acatgtaaat atcgtattag taaataccga ccaaaaaaaa tattgtatta gtaaatttga | 660 |
| cacatatcgc aattttgtg agctaacaat tttaaaaatc aaataagatg acgaacaaag | 720 |
| ctctggttta aacttctctcc catcaatttt ttcattaaac caaatttaac caattatttg | 780 |
| gcctaataac tgcgtctacg ttattaagaa taagaactta ttttgtgttt cagtagaaaa | 840 |
| cacactcgtt cacaaaatgc ctagtaagag taaaggacga tcaccgccac caagtgtgtt | 900 |
| tctcggataa acacatggaa tccagccatt acttaaacga cacgtgtacg ctcatgattt | 960 |
| attaatgcac acgtaatcga tcctctgaca aaaaccataa cgaatacaga aaacacacga | 1020 |
| atacacttcc ctgcgctata ataagctag cacgaaaaaa tttaacagat agagacaaga | 1080 |
| caagc | 1085 |

<210> SEQ ID NO 3
<211> LENGTH: 979
<212> TYPE: DNA
<213> ORGANISM: Arabidopsis thaliana

<400> SEQUENCE: 3

| | |
|---|---|
| attctatttg ccagactcta cggcggtata ttcgctttta gaaaaaaaac aattttgtcg | 60 |
| aaacttttt tttttgtaa atattgtaga ttccacacac aagactgtct aagattcttt | 120 |
| gataagacac gacaaatgcg atttaagatt tttcaaagaa atgaggttcg ttgattgttc | 180 |
| cactaggttt ggtatatta taatttgaat tttttttttt aaagatattt ataagaaaac | 240 |
| gaaggagtgt gctcgcgtca agtgtgtact aatagtcgat gacactagtg atacgacgat | 300 |
| actggaaagg gacatcaata ttcattagta agccatctta gcaaaaacgt tgttatcaga | 360 |

```
taagaaaagt tctcagactg acgtggctgt caatctccac aacgtgttta tctcccattt    420
gggtagttac ggacaaagac gttgaaaaga caacaatatg gtctaaaaga ttgacatgga    480
aagaaaattg tttatccgac aaagacctct tggtccaacg tggcttttcac atcactagtt   540 tactatttca catctcatgg aaaattactg aaattagtac ttgtctgtat tttgttttt     600 cgtcaagtat ttgtttgtat actttaggta attgcgtgcc gaagaaacat tgctaaattg    660
atatttatac caacttacaa tagtttacag ttcaaaaata gaaatctcca ttttgaagat    720
acaccactaa ttttcttcat ttatttaccc cataagagaa cgagaaaaga acaatagtcc    780
gttgatttcg ttaaaatcta gtttcagaaa gacacgtcta gatctgtctg atcagggcag    840
atagacacaa gtgacgaagc aaaagaaaca caaaataag ataagaactc ttaccactaa     900
aagataaaaa taagaaaaaa aataaaacaa attcaacgat ttgccaagat aaaagcagac    960
actgtacata agctccgca                                                 979

<210> SEQ ID NO 4
<211> LENGTH: 1067
<212> TYPE: DNA
<213> ORGANISM: Arabidopsis thaliana

<400> SEQUENCE: 4
gttgtttata ttgttactag gcctttgtat aaataccaaa tactttgatt attttttac     60 tgatttcatg tcaaacaaaa ttccaaacaa cttaaaggaa aaagcttact cgattggaat    120
aaaaattgta cgtttaacaa atgatatta gtgaaataaa taaaccagct caacatttaa     180
ggatttctac gtgtatatac agtaatcgtg tttagtatta attagctata gtttagcctc    240
aaaaaacaaa gatccaaaac aacatgacga aattgacttc cacatcgtgt cctttctcgt    300
cgacataaaa actttaatat atagatgcat gtataagtat actcactatt tgtgtcatta    360
gtattttctt ttttgatact tggagctaat gacaaaaatt ccgctagaaa tatcttctcc    420
aacgatagct acaaacaaat actaccattg cgtcatcatc acttatttat attcgatatt    480
tcagtcaaca acactaatct ctttccaccaa atctttgga ctattattac aaatgaatta    540
aaaacttgga cccttaataa catatttgtt tcattaaatc tatacaactc ttattaaaaa    600
tgatattttc ttaaatcaaa aattaatcaa aattaaggta ggctctagag gattgcatca    660
tttgcccacc cacattagcc tgccattatt attggacggt aacaaatttc cttacaccaa    720
taaatggtaa gttacaatta ttattaacat ttctatataa aatagtttgg ttatttacat    780 taattttttat ttaatactat aaacttaaaa attcaatgct gaaaagtgta acggaaagag   840
ggacattaaa tatatgttaa tataataagt atatttacta tttaaaaaag acttatgtaa    900
atacatattg tatagagaga aaaataaccc atagtataaa aacttgcatc tctaaaaccg    960
cagcattgat aataagagtc tctttcttct taagtatctc ttaattaacc cacataatat    1020
atttacaagt ggccgcctca tacatcccct ctcaagtcct ttgcttc                  1067

<210> SEQ ID NO 5
<211> LENGTH: 1056
<212> TYPE: DNA
<213> ORGANISM: Arabidopsis thaliana

<400> SEQUENCE: 5
atcttaactt ctgcaacgaa tcaatgtatt aatttatagg agatccggat aaaattatgg    60
atatatgcac gctacttctt tcattttaa ttaggtaaat ggttataact ttatttata      120 tatcaattaa atgattttgg tatgagatta ctagtacact ttctttgcaa atgttttaaa   180
```

```
cacgacaaga caaaaatatt acaagcatat tttggtaaaa aatatcataa gctttcatat    240
caaaatcatt agttatgatg ttagattttt tttttttttt tttaacacta caaaaagctc    300
tggtcttaat atgttagaaa ttttagtcca aaccagccta cagaggattt agctaaacaa    360
ttcccaagca ccttttaagt gttaaccgaa ataacgtaat atgatgttaa aggttacata    420
aaaacaaaac taagaatttt tcatatgaaa agttaacgta cgtgtcttag tgtaacctaa    480
ttttagttca cagtatataa attcttttaat gagatgatcg caaaatcgct gtatacaatt    540
tcgtacttaa ttcgttagtc ttgaaaagtt gacctaattt agatcaaatt aaggttaact    600
acaataaaaa tttaactaac gtaatgggat tctttaaaat taaaaaatcg ttgattagat    660
agatatttta tctttaaggg agacacagag acaatttgga caaaaaggt cttcctgaga     720 aagaagtgga ccacaatcgt ggcgcgaaag gaacttcctc ctcccctctg ttgccttgtc    780
attgggccac gtatatctcc acctgatcgt gatgcttacg tggtccattt ctagatacta    840
tagtgaccag atcaacggtc aagattgatt ctaatttaga cgaaagacca acacgtcacg    900
tcgctagagt aaaagatttt ttgaaggcgg agggagaaaa atcaaaagtt aaaagtaatt    960
tgaaaacgag gaagagaaaa aggaatttta aaatgtttaa tgaagcggta ggccgcatgg   1020
gtatataaat gggcacgctt tgtaacgtgt aacgat                             1056

<210> SEQ ID NO 6
<211> LENGTH: 1057
<212> TYPE: DNA
<213> ORGANISM: Arabidopsis thaliana

<400> SEQUENCE: 6
ggtgaattaa aggtagtgaa cgccacttgc ggatgcatgg tacatcgcgg caaattttat     60
aaaaatgtag aatgggggact ttttcattta tttaataaat aatccattta tttggcttta   120
agaaacctat caattaccaa aaaaagaaga aaactagaag aaaaaaaaat aaaactcgag    180
atgtgagtaa tttcatagac ttgattggtt tccgaaaaat ttaaaagtat aattgataaa    240
atgttagatt aaaagttaat ttaatagcta taaaaaatac aaattgagag gaactacaca    300
catttttttt tttttatgga acctaacaca aattttttt tttgttgaat gcagataagt    360
aatacctact tgacagaaac aaactaaaat aaaataaaaa taaaaataac gaaacataac    420
cttatgagtt tttgagtcat gcaattaaaa aatatatatg attttaacgt ccacatatgc    480
cgtaaatagt cggtcggtca tcggtcagac aaactaccat aggaaagaaa tttaaacatg    540
gaaaatagac caaacgggaa atgggcccaa caagactttt ccttgtccac gtgtatcatc    600
accgcctact acgttccacg tagacacgtg tccacataat aaccaatcag aaaatcccac    660
actaatatag tgtattaaat accccatacg acgtcgtata tctgaagtgg aacccattga   720
taaacacata aaaatgaccg atcaaccacc acgagctcga tttaaaaacc ttgatgagtc    780
gaacagtcta gatactgaca cgtgtcgtta tgtaacgccg tggcagcacc tggattatac    840
tgggacccac tgtaaatagt taattcaaaa cgaagcttcg cgcgcgtatc ctaaaccgtt    900
agattccacc atattgttga atagccgttg gatcaaaatc tttctctgga aacgtttagt    960
agtcggtcgt atttaattat ccaaagtaat tagcgattaa tcttttaatt aattaagaca   1020
aaatcttata taaagcacca ttaagcatca cccacat                            1057

<210> SEQ ID NO 7
<211> LENGTH: 1055
<212> TYPE: DNA
<213> ORGANISM: Arabidopsis thaliana
```

```
<400> SEQUENCE: 7
taatctaaaa gctaccaaat aacctaatat tagtgttttt gaataattgc ctttgtattt      60
tacaagtatt gatttagttg attttcgacg aaaagctttc ctcaaatttt ttaatattat     120
cacctatatt ctcattacgt aaaggatcat atcaaggatg ataagaaatt ataataagaa     180
aaataaatga ttctaggtgt ttattaaatg actccctctt tctacacttg ttaaatgaaa     240
acgtagttgc ttttcctgg aataacacta ataattccga gcaagcaacc tccactacta      300
ctatctttta tcattttat ccctagaaag ggactttaaa cttgtaactt gtataacaca      360
tcacatcatc ttctttttt cttcctttcg ttttgtggtt aatttggtaa tttactttcg      420
atgcaataaa caagccgaaa atatgaaaaa cgttcatctg ttaattagta ccaagtttat     480
acttgaagct tgaatatagt tatctacacc ataatttttt gtattatttt acaagaaatt     540
taaatacccg cttaggtaga cgtcttaatc cataacttat agaaacttaa aaaacttggt     600
acgaaagatt cttcttaatc atcagctaac taaatcttgt ttttatcact aaatatttta     660
ttagcaatca aatattgtgg aaaatgaatt agcgtgttaa ccaatgggtt tggttatagg     720
aaatataaaa tatcaaagga gagaagggac cttgtcaaag aagacaatcg atacttctta     780
acgtgggtcc taaaatggca acatcttttt tttgtcattt catgtgtgta gataagctct     840
aatttcttac ctcaccaatg gttatatgaa tataaaaatg atttctgtaa acaattctgt     900
tgaaattatg taattatcat tatatattaa atcactaatc aacactttat actttttaac     960
agtgacaaca ctaaatgcgt ccatttaaga gtttcgcttt tccgtctctt cttcttcttt    1020
gatcatctat ttaaggatct agagaaacca cttcg                              1055

<210> SEQ ID NO 8
<211> LENGTH: 1023
<212> TYPE: DNA
<213> ORGANISM: Arabidopsis thaliana

<400> SEQUENCE: 8
atgagaagta acatagtat tttgaaaaat agcaagaaag gaaatctgaa attttagact       60
aatagcaaaa agattttgag ttaagttgac aaaattgaat tttagtaact tgggacctt      120 tttacatctt ttttatataa aaaaagtcga cacatgagat attacttata aaattaaaaa     180
tacattattt tcatgaatat ttaatagagt ttatgaattt ctcacatatg ttaattatta     240
agtgctgaaa atgttaaat tgtttttctg tataaatgtt aagtactgaa aaatgcttgg      300
aatgtttttc tatatttata tctctgctat ttatatgtgt gatttagtgt tatttagggc     360
attaaatata agatataaaa atattaaatt tttctataat ttaaaaataa gtaaataaac     420
atgttgtaga ccgtaattgc cagattattt gtgctgtttc ctaaatactt ttacattctt     480
tgatggtcac caaattaact ataagaaaaa ttaggactca gtctcattaa tttttcggaa     540
gagaaaaaga atcagtctca tggtagttgt taggaaatat ttgaatattg tttcgccatt     600
agaaactttt tatgtggatt ttttttcctga aaacgatggt tactattaat taaacggacc    660
gacaagaacc ttgttgacgt ggtaacaagt gatgacacat gctaattggc catcattgtc    720
aaataatttg ttcgcaaggc gtgatacgtg tacgttgtta ttcagacgta gcaaacagat     780
tcacgacttt tgttcaattt gtcttttgtat ggagtatgga cctaacatct ccaacggacc    840
aatgctattg ggtcaagtcc atcttttcta ggttaagttc attctttggg ctttagttaa     900
gtatagagaa agaacatatt ggaagaaaaa tttagatgtg gtttgtattg catgcgcata    960
```

```
tgaaatgtaa taatttgagg atacatatat agtaagaaaa aatgagtgac ccaagtaaga    1020
atg                                                                  1023
```

<210> SEQ ID NO 9
<211> LENGTH: 1176
<212> TYPE: DNA
<213> ORGANISM: Arabidopsis thaliana

<400> SEQUENCE: 9

```
ctattatatg ccatttctat ttagttttttt tttctaaaaa tatatataaa tatggtgttg     60
ttaacataaa aacagaaaaa aagaaaaatt tagaaaattt tctcaagaat cattatatct    120
gtgatttatc atataagttc aaatatgata ttagaaacaa atagtttacg agtataatag    180
tattgtcaat ttttcaatct gaagtaaata tcttttttgta aggaagggggg caacaaatga    240 tcacaacaga gttggcaaaa agttatcaaa tcgcatgcac ggaagtttta cgtgtggtga    300
aggtaaactt gtattacact tatctataaa aattagttta ggctttgatt ctaaatcaaa    360
tctccgatta gaaaaaattg cgtaagcaaa tagctggaaa aaattgtatc ccatcatact    420
taagtcacaa tgttttgttt ttgagatttg tgatgtaatc aatatatgtt ttacaatgca    480
agtataataa tattaaagtc acattctaag aaaattatga tttgtgtcat acgtatacaa    540
aaacacccgt cacacatcct gacttctgaa cgttaaatct gtcgcacaca atcataaaaa    600
tttaaaaatt caccagagat gtactgaaaa gaatataatt aatcacatga tgatatatgc    660
ataggagatg aggattattc attttctgaa attccctata tgaaccatta taattgttta    720
gtaatcagtt cagaaatgct aatcattata tgaaccatta taattcccttc cattttatt    780 taagatccac ttaacaggat tgttaatat gcacccacat cactaaatac attggtacgc    840
aaccgttgtt ccatttccat tttcacatcg accagaatgt ttactatgcg gtaaattgtg    900
tagtatgcag atttttttgt atcatttaat tttctaacac ttgttaagtc gaaactaatt    960
ttgtcacaag taaagaaat aaaaaaggtg gaaattatta atcagtagtt agatgattag   1020
tttcgagttg aaatgaaact cgacttaaca agtgatagcg acgactctag aaacagccaa   1080
aatccgccct attgctacct gtcgacccac aaatcgttta ctcaaaaatg aataaaaaat   1140
ttacgataaa gcaaacccaa agttatatct tattat                             1176
```

<210> SEQ ID NO 10
<211> LENGTH: 686
<212> TYPE: DNA
<213> ORGANISM: Arabidopsis thaliana

<400> SEQUENCE: 10

```
gaggagagag gaggtaaaca ttttcttcta ttttttcata ttttcaggat aaattattgt     60
aaaagtttac aagatttcca tttgactagt gtaaatgagg aatattctct agtaagatca    120
ttatttcatc tacttctttt atcttctacc agtagaggaa taaacaatat tcagctcctt    180
tgtaaataca aattaatttt cgttcttgac atcattcaat tttaattta cgtataaaat    240 aaaagatcat acctattaga acgattaagg agaaatacaa ttcgaatgag aaggatgtgc    300 cgttttgttat aataaacagc cacacgacgt aaacgtaaaa tgaccacatg atgggccaat    360
agacatggac cgactactaa taatagtaag ttacatttta ggatggaata aatatcatac    420
cgacatcagt ttgaaagaaa agggaaaaaa agaaaaaata aataaaagat atactaccga    480
catgagttcc aaaaagcaaa aaaaaagatc aagccgacac agacacgcgt agagagcaaa    540
atgactttga cgtcacacca cgaaaacaga cgcttcatac gtgtcccttt atctctctca    600
```

| | |
|---|---|
| gtctctctat aaacttagtg agaccctcct ctgttttact cacaaatatg caaactagaa | 660 |
| aacaatcatc aggaataaag ggtttg | 686 |

```
<210> SEQ ID NO 11
<211> LENGTH: 1061
<212> TYPE: DNA
<213> ORGANISM: Artificial Sequence
<220> FEATURE:
<223> OTHER INFORMATION: A synthetic oligonucleotide

<400> SEQUENCE: 11
```

| | |
|---|---|
| cctgaagcca accatatgct aagaatattt acataaaata ccttaaatcg aatataatct | 60 |
| atatgggtaa ttatatccaa aaatatcacg aaatattatt tcgttgatga tagactttaa | 120 |
| aaattgcata ttatgtacag aaatacaatt accgaacagg ataattttt tgattacatt | 180 |
| gaccacataa tataacaaaa cactaatatt gttttgataa atatttgatg ttttaggaac | 240 |
| aaaatacatg atgttttcaa ctttcaatat aaaattaatt aatatacttt tttgggttta | 300 |
| gaggtttcta ttctgtaaat tgtattttt tttcctgtag attgtattac tattggtcga | 360 |
| ttaaatggat aataaattaa ttttagtttg gaaataaaaa caaataaatg aatccttaaa | 420 |
| catcaactat aaaaagacag aggagtatct ttaaagaaac ttggattgtg atattgcact | 480 |
| gtaaatagaa cataaaatgt tgcagtgtaa ctttattta atcaaataaa caaatgttag | 540 |
| taaaaaaaaa tatatatgtt gcaaacaagg attaaattca ctagtaccga catactaata | 600 |
| ccgacatcag tttaccgaca tgagtttacc gacatagaca taccgacata ctaataccga | 660 |
| catcagtttta ccgacataga caacacgtgt cccttcacg tgtactagta aattctcatt | 720 |
| aacaaacaaa caaaaacaaa aacaaaaaca aagatagtgc caagcattac atatataaac | 780 |
| aataaaaaga ccctacttat taatatcttt ccttaaagaa acatggatta ttatcatttt | 840 |
| ggcagtgtat gaagtaataa atataaacaa aatgaaataa gaaaatgcaa gcaagtacaa | 900 |
| ttgatgatat aaagtaacca tggttaatca aaaaaacctg aaagactgaa atagagttaa | 960 |
| ccatagttaa gcttctctgg ttaaaagata attgctttgc tatatattaa acaacaattg | 1020 |
| gaacctcctc ttttatcaaa accaactctc tctacacact t | 1061 |

```
<210> SEQ ID NO 12
<211> LENGTH: 937
<212> TYPE: DNA
<213> ORGANISM: Artificial Sequence
<220> FEATURE:
<223> OTHER INFORMATION: A synthetic oligonucleotide

<400> SEQUENCE: 12
```

| | |
|---|---|
| cctgaagcca accatatgct aagaatattt acataaaata ccttaaatcg aatataatct | 60 |
| atatgggtaa ttatatccaa aaatatcacg aaatattatt tcgttgatga tagactttaa | 120 |
| aaattgcata ttatgtacag aaatacaatt accgaacagg ataattttt tgattacatt | 180 |
| gaccacataa tataacaaaa cactaatatt gttttgataa atatttgatg ttttaggaac | 240 |
| aaaatacatg atgttttcaa ctttcaatat aaaattaatt aatatacttt tttgggttta | 300 |
| gaggtttcta ttctgtaaat tgtattttt tttcctgtag attgtattac tattggtcga | 360 |
| ttaaatggat aataaattaa ttttagtttg gaaataaaaa caaataaatg aatccttaaa | 420 |
| catcaactat aaaaagacag aggagtatct ttaaagaaac ttggattgtg atattgcact | 480 |
| gtaaatagaa cataaaatgt tgcagtgtaa ctttattta atcaaataaa caaatgttag | 540 |
| taaaaaaaaa tatatatgtt gcaaacaagg attaaattca ctagtaaatt ctcattaaca | 600 |

```
aacaaacaaa aacaaaaaca aaaacaaaga tagtgccaag cattacatat ataaacaata      660
aaaagaccct acttattaat atctttcctt aaagaaacat ggattattat cattttggca      720
gtgtatgaag taataaatat aaacaaaatg aaataagaaa atgcaagcaa gtacaattga      780
tgatataaag taaccatggt taatcaaaaa aacctgaaag actgaaatag agttaaccat      840
agttaagctt ctctggttaa aagataattg ctttgctata tattaaacaa caattggaac      900
ctcctctttt atcaaaacca actctctcta cacactt                              937

<210> SEQ ID NO 13
<211> LENGTH: 141
<212> TYPE: DNA
<213> ORGANISM: Artificial Sequence
<220> FEATURE:
<223> OTHER INFORMATION: A synthetic oligonucleotide

<400> SEQUENCE: 13
gagtgttctg tgtgtttgtc gaaattccaa ggggattcag agatcaacaa gctcaagtgc       60
ggccatttgt ttcacaaaac atgcttggag aaatggatag actattggaa catcacttgc      120
ccattgtgta ggactcctct t                                                141

<210> SEQ ID NO 14
<211> LENGTH: 47
<212> TYPE: PRT
<213> ORGANISM: Artificial Sequence
<220> FEATURE:
<223> OTHER INFORMATION: A synthetic polypeptide

<400> SEQUENCE: 14

Glu Cys Ser Val Cys Leu Ser Lys Phe Gln Gly Asp Ser Glu Ile Asn
 1               5                  10                  15

Lys Leu Lys Cys Gly His Leu Phe His Lys Thr Cys Leu Glu Lys Trp
             20                  25                  30

Ile Asp Tyr Trp Asn Ile Thr Cys Pro Leu Cys Arg Thr Pro Leu
         35                  40                  45

<210> SEQ ID NO 15
<211> LENGTH: 849
<212> TYPE: DNA
<213> ORGANISM: Artificial Sequence
<220> FEATURE:
<223> OTHER INFORMATION: A synthetic oligonucleotide

<400> SEQUENCE: 15
aaaaccaact ctctctacac acttttttcag attccatcat cacttgttct tttcacaccc      60
aataaaaact tgcatctttc ttctaaattg ttgatgatcg cttctcatat ttgaccctag      120
agacaacatc atttctaccg acaaagattt gatatcgaat ccaacaagtg aaagatgggt      180
ctatcaagtc ttcctggtcc atcagaagga atgttatgtg tgatattagt aatacagca      240 ttatcgatct ccattgtcaa aggcattgta agatcattcc ttggcatagt aggaatcagt      300
ctctcgccgt cttcatcctc gccttcttcg gtgacggtat cttcagagaa ttcatcaact      360
tcagagtcat ttgatttccg ggtctgccaa ccagagagtt accttgagga gttcaggaac      420
cggactccga cactgaggtt tgagagcttg tgcaggtgca agaaacaggc agacaatgag      480
tgttctgtgt gtttgtcgaa attccaaggg gattcagaga tcaacaagct caagtgcggc      540
catttgtttc acaaaacatg cttggagaaa tggatagact attggaacat cacttgccca      600
ttgtgtagga ctcctcttgt tgttgtgcca gaagaccatc agctttcttc taatgtttgg      660
```

```
tgactgcttt tcactgtata ggttttttgt ttgagtgtgt ttgttgtgta cagctacttt      720
tactatgaat taggttgcat cgcggttgat tctcgagcag atttaaaccg gggatgggat      780
aatctgatgt acatatatat atataccccat gtgtatggag ctcttgtttg aacacagttt    840
tcttgaatc                                                              849
```

<210> SEQ ID NO 16
<211> LENGTH: 162
<212> TYPE: PRT
<213> ORGANISM: Artificial Sequence
<220> FEATURE:
<223> OTHER INFORMATION: A synthetic polypeptide

<400> SEQUENCE: 16

```
Met Gly Leu Ser Ser Leu Pro Gly Pro Ser Glu Gly Met Leu Cys Val
1               5                   10                  15

Ile Leu Val Asn Thr Ala Leu Ser Ile Ser Ile Val Lys Gly Ile Val
            20                  25                  30

Arg Ser Phe Leu Gly Ile Val Gly Ile Ser Leu Ser Pro Ser Ser Ser
        35                  40                  45

Ser Pro Ser Ser Val Thr Val Ser Ser Glu Asn Ser Ser Thr Ser Glu
50                  55                  60

Ser Phe Asp Phe Arg Val Cys Gln Pro Glu Ser Tyr Leu Glu Glu Phe
65                  70                  75                  80

Arg Asn Arg Thr Pro Thr Leu Arg Phe Glu Ser Leu Cys Arg Cys Lys
                85                  90                  95

Lys Gln Ala Asp Asn Glu Cys Ser Val Cys Leu Ser Lys Phe Gln Gly
            100                 105                 110

Asp Ser Glu Ile Asn Lys Leu Lys Cys Gly His Leu Phe His Lys Thr
        115                 120                 125

Cys Leu Glu Lys Trp Ile Asp Tyr Trp Asn Ile Thr Cys Pro Leu Cys
130                 135                 140

Arg Thr Pro Leu Val Val Val Pro Glu Asp His Gln Leu Ser Ser Asn
145                 150                 155                 160

Val Trp
```

<210> SEQ ID NO 17
<211> LENGTH: 1194
<212> TYPE: DNA
<213> ORGANISM: Solanum lycopersicum

<400> SEQUENCE: 17

```
atgattgata acgttaaagg tatgccgccg gcaaccgaga aggttgccg gttaacggcg        60 ttgatagatt ccggtggact agcagaagta gatctgagtg agaaggagca aaattctact      120
cgacgtaggc gattggatga acgtttgttg aaatcgacga ctgagctacc ggaaaatttc      180
gatgtcttcg cagatgatta caggcattgt aagaggaaaa aaagtactgt aactgatact      240
gatgatcatc gagttcaact agcgttatct agtgaagtga aaaagtaag ggagagcttg       300 gtgacgtgct gttcacatgg atcgatatcg ttgatcggcc ggagaaggga atggaagat       360 gcggtggcga tttatccgtg tttttttcagt gaaggcggcg gcggcggcag caggaggtat    420
gattattttg gtgtttacga cgggcatgga gggtcacgtg tagcgaacgt gtgccgtgac    480
tttttgcacc gtttagtgat acagcaagtt tcggaaggag aagattacga tgggaagagt   540
attaactggg agaaagttat gacgagagt ttccgtaaaa tggacgaaaa ggtgaacaag     600
gaaggggcgg agatggcgac gataggatca acggcggtgg tagcggtggt gggagtggag   660
```

```
gaatttgttg ttgcgaattg tggagattca agagctgtgc tttcacgtgc tggagttgcc    720
gtacctttgt ctattgatca taagcctgac agacctgatg agctggatag aattgaaaat    780
tcaggtggga aagtcataaa ttggaatgga caaagagtct taggagttct tgctacttca    840
agatccatag gtgatatgta cctcaaaccg tacgtgatac cagatcctga agtgatagtt    900
agcaaaagaa gcgatgaaga tgagttctta atacttgcaa gtgatggtct atgggatgtc    960
attccaaatg atgttgcgtg tgacgttaca agaagatgct tgaatggtca aacgttcaga   1020
aggtgcgatc aacaaaccaa atcctataag agagatgaag gcgtcaaaga aagtctcgca   1080
gcacgggcag cttccttcct tgcagagtta gcaattgctc ggggtagtag ggataacatc   1140
agcgtaattg tcgtcaattt gaatagatct gtacgttcat ccattgatag ttaa         1194
```

<210> SEQ ID NO 18
<211> LENGTH: 397
<212> TYPE: PRT
<213> ORGANISM: Solanum lycopersicum

<400> SEQUENCE: 18

```
Met Ile Asp Asn Val Lys Gly Met Pro Pro Ala Thr Glu Lys Gly Cys
 1               5                  10                  15

Arg Leu Thr Ala Leu Ile Asp Ser Gly Gly Leu Ala Glu Val Asp Leu
            20                  25                  30

Ser Glu Lys Glu Gln Asn Ser Thr Arg Arg Arg Leu Asp Glu Arg
        35                  40                  45

Leu Leu Lys Ser Thr Thr Glu Leu Pro Glu Asn Phe Asp Val Phe Ala
 50                  55                  60

Asp Asp Tyr Arg His Cys Lys Arg Lys Ser Thr Val Thr Asp Thr
 65              70                  75                  80

Asp Asp His Arg Val Gln Leu Ala Leu Ser Ser Glu Val Lys Lys Val
                85                  90                  95

Arg Glu Ser Leu Val Thr Cys Cys Ser His Gly Ser Ile Ser Leu Ile
            100                 105                 110

Gly Arg Arg Arg Glu Met Glu Asp Ala Val Ala Ile Tyr Pro Cys Phe
        115                 120                 125

Phe Ser Glu Gly Gly Gly Gly Ser Arg Arg Tyr Asp Tyr Phe Gly
 130                 135                 140

Val Tyr Asp Gly His Gly Gly Ser Arg Val Ala Asn Val Cys Arg Asp
145                 150                 155                 160

Phe Leu His Arg Leu Val Ile Gln Gln Val Ser Glu Gly Glu Asp Tyr
                165                 170                 175

Asp Gly Lys Ser Ile Asn Trp Glu Lys Val Met Thr Glu Ser Phe Arg
            180                 185                 190

Lys Met Asp Glu Lys Val Asn Lys Glu Gly Ala Glu Met Ala Thr Ile
        195                 200                 205

Gly Ser Thr Ala Val Val Ala Val Val Gly Val Glu Glu Phe Val Val
    210                 215                 220

Ala Asn Cys Gly Asp Ser Arg Ala Val Leu Ser Arg Ala Gly Val Ala
225                 230                 235                 240

Val Pro Leu Ser Ile Asp His Lys Pro Asp Arg Pro Asp Glu Leu Asp
                245                 250                 255

Arg Ile Glu Asn Ser Gly Gly Lys Val Ile Asn Trp Asn Gly Gln Arg
            260                 265                 270

Val Leu Gly Val Leu Ala Thr Ser Arg Ser Ile Gly Asp Met Tyr Leu
        275                 280                 285
```

```
Lys Pro Tyr Val Ile Pro Asp Pro Glu Val Ile Val Ser Lys Arg Ser
    290                 295                 300

Asp Glu Asp Glu Phe Leu Ile Leu Ala Ser Asp Gly Leu Trp Asp Val
305                 310                 315                 320

Ile Pro Asn Asp Val Ala Cys Asp Val Thr Arg Arg Cys Leu Asn Gly
                325                 330                 335

Gln Thr Phe Arg Arg Cys Asp Gln Gln Thr Lys Ser Tyr Lys Arg Asp
            340                 345                 350

Glu Gly Val Lys Glu Ser Leu Ala Ala Arg Ala Ala Ser Phe Leu Ala
        355                 360                 365

Glu Leu Ala Ile Ala Arg Gly Ser Arg Asp Asn Ile Ser Val Ile Val
    370                 375                 380

Val Asn Leu Asn Arg Ser Val Arg Ser Ser Ile Asp Ser
385                 390                 395

<210> SEQ ID NO 19
<211> LENGTH: 63
<212> TYPE: DNA
<213> ORGANISM: Artificial Sequence
<220> FEATURE:
<223> OTHER INFORMATION: A synthetic oligonucleotide

<400> SEQUENCE: 19
gagctccacc gcggtggcgg ccgctctagt actagtggat ccccgggtgg tcagtccctt    60
atg                                                                  63

<210> SEQ ID NO 20
<211> LENGTH: 877
<212> TYPE: DNA
<213> ORGANISM: Cauliflower Mosaic Virus

<400> SEQUENCE: 20
aagcttgcat gcctgcaggt ccccagatta gccttttcaa tttcagaaag aatgctaacc    60
cacagatggt tagagaggct tacgcagcag gtctcatcaa gacgatctac ccgagcaata   120
atctccagga aatcaaatac cttcccaaga aggttaaaga tgcagtcaaa agattcagga   180
ctaactgcat caagaacaca gagaaagata tatttctcaa gatcagaagt actattccag   240
tatggacgat tcaaggcttg cttcacaaac caaggcaagt aatagagatt ggagtctcta   300
aaaaggtagt tcccactgaa tcaaaggcca tggagtcaaa gattcaaata gaggacctaa   360
cagaactcgc cgtaaagact ggcgaacagt tcatacagag tctcttacga ctcaatgaca   420
agaagaaaat cttcgtcaac atggtggagc acgacacact tgtctactcc aaaaatatca   480
aagatacagt ctcagaagac caaagggcaa ttgagacttt tcaacaaagg gtaatatccg   540
gaaacctcct cggattccat tgcccagcta tctgtcactt tattgtgaag atagtggaaa   600
aggaaggtgg ctcctacaaa tgccatcatt gcgataaagg aaaggccatc gttgaagatg   660
cctctgccga cagtggtccc aaagatggac ccccacccac gaggagcatc gtggaaaaag   720
aagacgttcc aaccacgtct tcaaagcaag tggattgatg tgatatctcc actgacgtaa   780
gggatgacgc acaatcccac tatccttcgc aagacccttc ctctatataa ggaagttcat   840
ttcatttgga gagaacacgg gggactctag aggatcc                            877

<210> SEQ ID NO 21
<211> LENGTH: 594
<212> TYPE: DNA
<213> ORGANISM: Artificial Sequence
```

```
<220> FEATURE:
<223> OTHER INFORMATION: A synthetic oligonucleotide

<400> SEQUENCE: 21
acaacatcat ttctaccgac aaagatttga tatcgaatcc aacaagtgaa agatgggtct      60
atcaagtctt cctggtccat cagaaggaat gttatgtgtg atattagtta atacagcatt     120
atcgatctcc attgtcaaag gcattgtaag atcattcctt ggcatagtag gaatcagtct     180
ctcgccgtct tcatcctcgc cttcttcggt gacggtatct tcagagaatt catcaacttc     240
agagtcattt gatttccggg tctgccaacc agagagttac cttgaggagt tcaggaaccg     300
gactccgaca ctgaggtttg agagcttgtg caggtgcaag aaacaggcag acaatgagtg     360
ttctgtgtgt ttgtcgaaat tccaagggga ttcagagatc aacaagctca agtgcggcca     420
tttgtttcac aaaacatgct tggagaaatg gatagactat tggaacatca cttgcccatt     480
gtgtaggact cctcttgttg ttgtgccaga agaccatcag ctttcttcta atgtttggtg     540
actgcttttc actgtatagg tttttgttt gagtgtgttt gttgtgtaca gcta            594
```

DROUGHT-TOLERANCE IN PLANTS

This application claims benefit of priority to the filing date of U.S. Provisional Application Ser. No. 61/937,865, filed Feb. 10, 2014, the contents of which are specifically incorporated herein by reference in their entity.

GOVERNMENT FUNDING

This invention was made with government support under DE-FG36-02GO12026 awarded by the U.S. Department of Energy. The government has certain rights in the invention.

BACKGROUND

Drought is one of the major limiting factors for plant productivity and spatial distribution. The annual loss in yield of major cereal crops due to drought is estimated to exceed ten billion dollars globally. Desertification, defined as "Land degradation in arid, semi-arid and dry sub-humid areas," is happening in about 70% of the total of the world's dry lands (3.6 billion hectares) and has become a very distinctive global issue with major environmental consequences. It affects about 25% of the total land area of the world and about 17% of the world population. Conventional crop improvement for enhanced drought tolerance has been ineffective, mainly due to limited germplasm resources and incompatibility in crosses between distantly related plant species.

Development of drought-tolerant plant species through biotechnology is both economically and environmentally important. Recent advances in plant gene discovery and genetic transformation have begun provide the tools for generating stress-tolerant crops using transgenic approaches. Despite the enormous economic and environmental significance, development of transgenic crops that confer drought tolerance in a highly controlled manner remains a challenge.

SUMMARY

Controlled strong drought-inducible promoters are described herein that can enhance the expression of operably linked coding regions. Examples of coding regions that can be operably linked to the promoter segments described herein include drought-tolerance factors. The constructs and methods described herein help protect plants from drought stress, and improve plant productivity.

Constructs containing promoter segments linked to heterologous nucleic acids are described herein.

Plants that include a promoter nucleic acid segment are also described herein, where the promoter nucleic acid segment includes one or more nucleotide sequences with at least 50% sequence identity to any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a combination thereof. Such promoter nucleic acid segments are particularly useful when removed from their natural chromosomal location, and covalently linked to a heterologous nucleic acid. For example, such drought-inducible promoter segments can be operably linked to a heterologous nucleic acid that includes a coding region that encodes a drought tolerance factor.

Plant parts, plant tissues, and plant seeds that include one or more promoter nucleic acid segment operably linked to a heterologous nucleic acid that includes a coding region are also described herein.

Methods for producing drought tolerant plants are also described herein. Such methods can include expressing a drought tolerance factor from a promoter nucleic acid segment that includes one or more of nucleotide sequences with at least 50% sequence identity to any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a combination thereof, which nucleic acid segment is covalently linked to a heterologous nucleic acid encoding the drought tolerance factor.

DESCRIPTION OF THE FIGURES

The patent or application file contains at least one drawing executed in color. Copies of this patent or patent application publication with color drawing(s) will be provided by the Patent and Trademark Office upon request and payment of the necessary fee.

FIG. 2A is a schematic diagram of the GUS reporter construct in the pCB308 backbone. Promoter segments were inserted into the underlined sites of the MCS2 (multi-cloning site) upstream of the uidA coding region (encoding GUS) by use of appropriate restriction enzymes. The sequence of the multi-cloning site that terminates in the ATG for the uidA coding region is as follows (SEQ ID NO:19):

```
1    GAGCTCCACC GCGGTGGCGG CCGCTCTAGT ACTAGTGGAT
41   CCCCGGGTGG TCAGTCCCTT ATG.
```

Figure 2A:
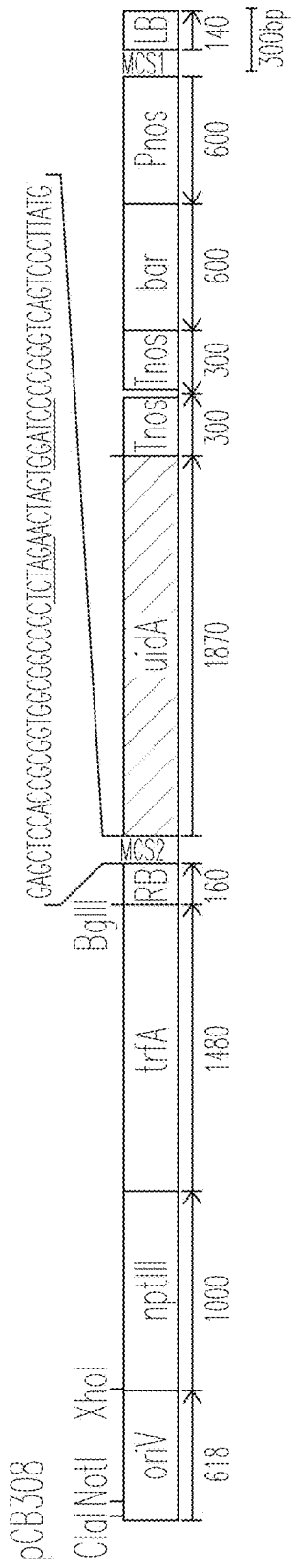
FIG. 2A-2B illustrate the structures of GUS reporter constructs used for identifying drought-inducible promoters.
Figure 2B:
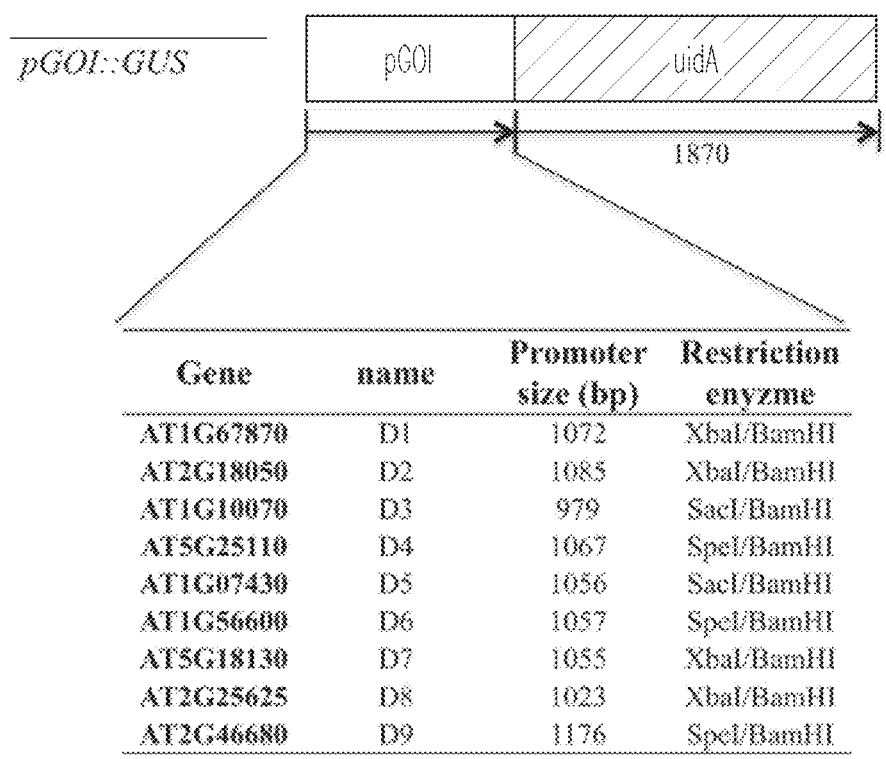

The numbers under each DNA region in the FIG. 2A diagram indicate the approximate size of the region in base pairs and the arrows show the orientation of transcription. FIG. 2B is a schematic diagram showing the juxtaposition of selected GOI promoter segments to an uidA coding region. The selected promoters are from the indicated GOI function genes, which are identified by accession numbers in FIG. 2B, and whish have the sequences described herein. GOI, Gene of Interesting Function; bar, gene for phosphinothricin acetyltransferase; LB, left border of the T-DNA; MCS, multiple cloning site (from pBluescript II); nptIII, gene for neomycin phosphotransferase for kanamycin resistance (from pBIN19); oriV, part of RK2 origin of replication (from pBIN19); Pnos, promoter of nopaline synthase gene; RB, right border of T-DNA; Tnos, terminator of nopaline synthase gene; trfA, part ofRK2 origin of replication; and uidA, gene for P-glucuronidase (GUS).

Figure 3C:
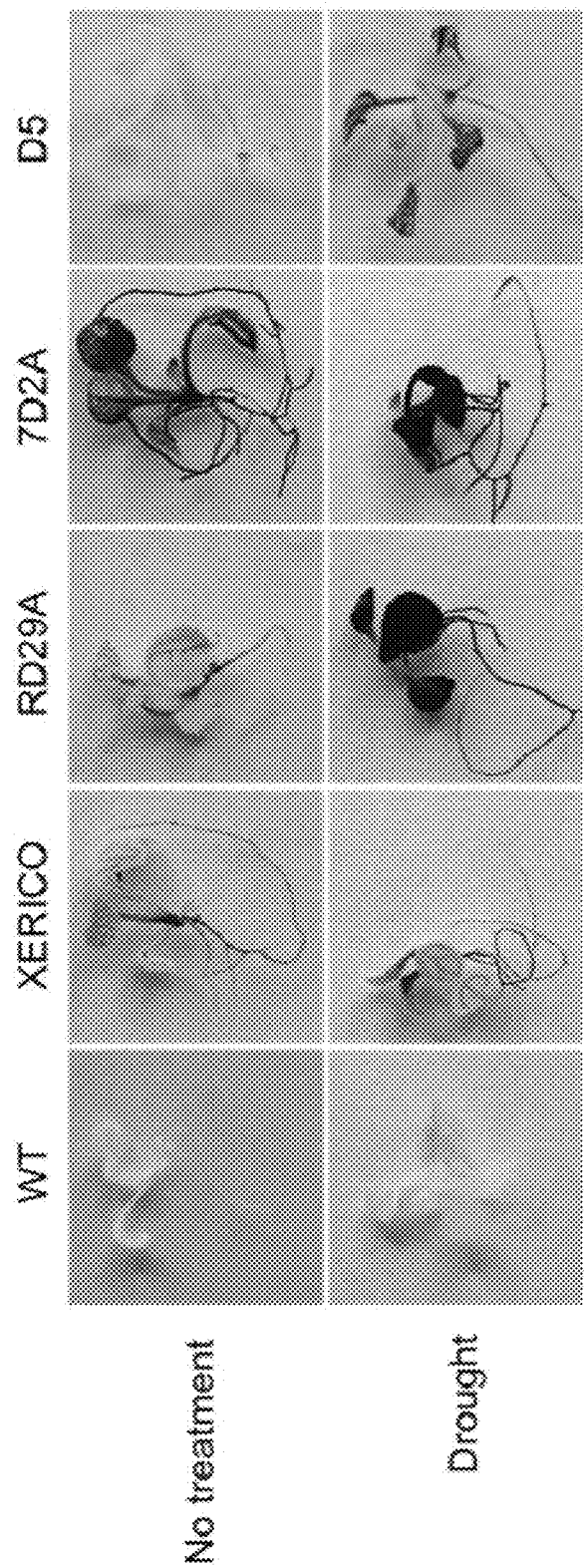

FIG. 3A-3C illustrate the structures of GUS reporter constructs, and how GUS expression correlates with drought stress conditions for some constructs. FIG. 3A is a schematic diagram of the GUS reporter construct in the pCB308 backbone. Promoter segments were inserted into the multi-cloning site (SEQ ID NO:19) upstream of the uidA coding region (encoding GUS) by use of appropriate restriction enzymes. FIG. 3B shows schematic diagrams of four types of constructs that were made and tested: a pXERICO::uidA construct, a pRD29A::uidA construct, a pXERICO+7D2A::

uidA construct, and a pD5::uidA construct. The pXERICO+ 7D2A promoter is a chimeric promoter containing seven DREs (drought response elements, TACCGACAT) and two ABREs (ABA response elements, ACACGTGT) in the native XERICO promoter (937 bp). FIG. 3C illustrates drought-inducible expression of the GUS reporter gene (dark regions) by four drought-inducible promoters: XERICO, RD29A, 7D2A, and D5 in seedlings. Histochemical staining was performed using 8-day-old, agar plate-grown T3 transgenic seedlings expressing GUS driven by the three promoters under no stress or drought stress conditions. Drought stress was induced by keeping the lid off the dishes for 20 hours on a clean bench before GUS analysis.

Figure 4A:
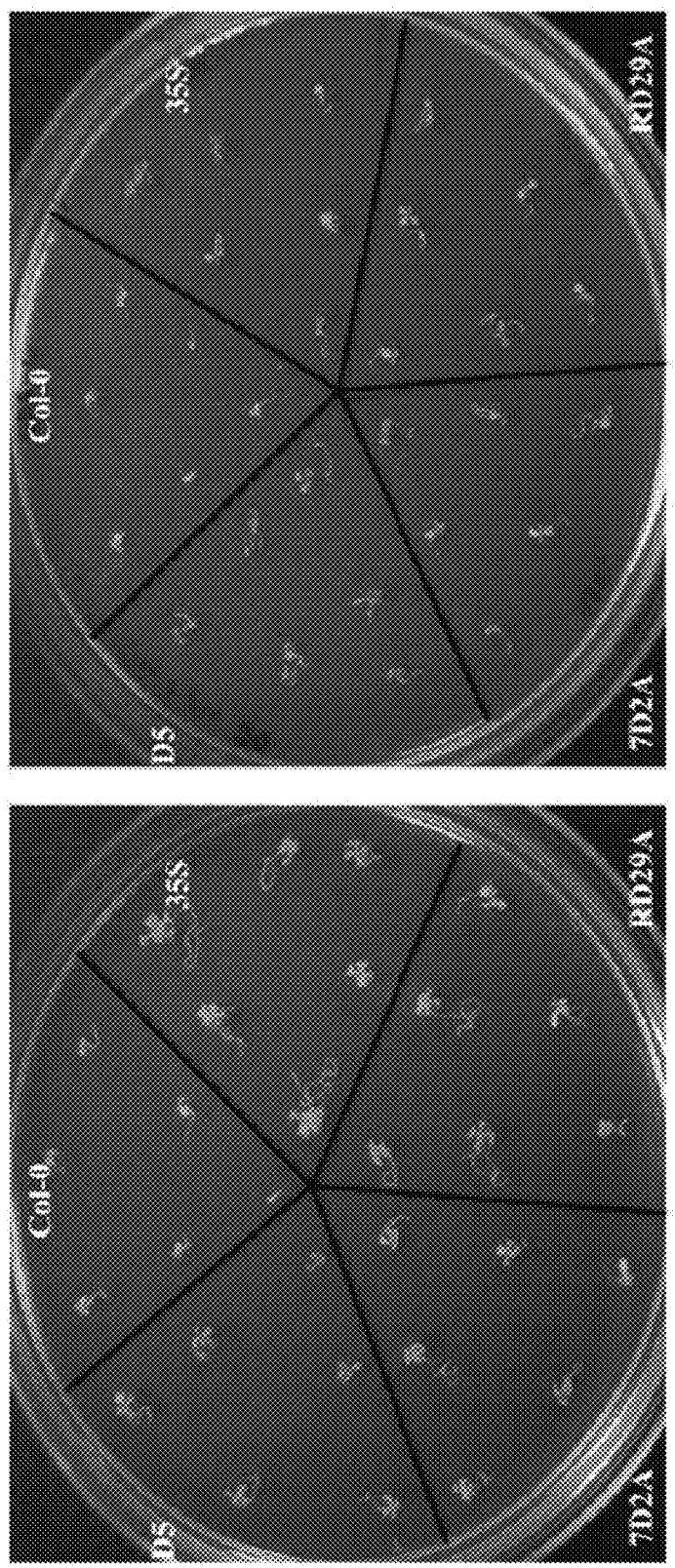
Figure 4B:
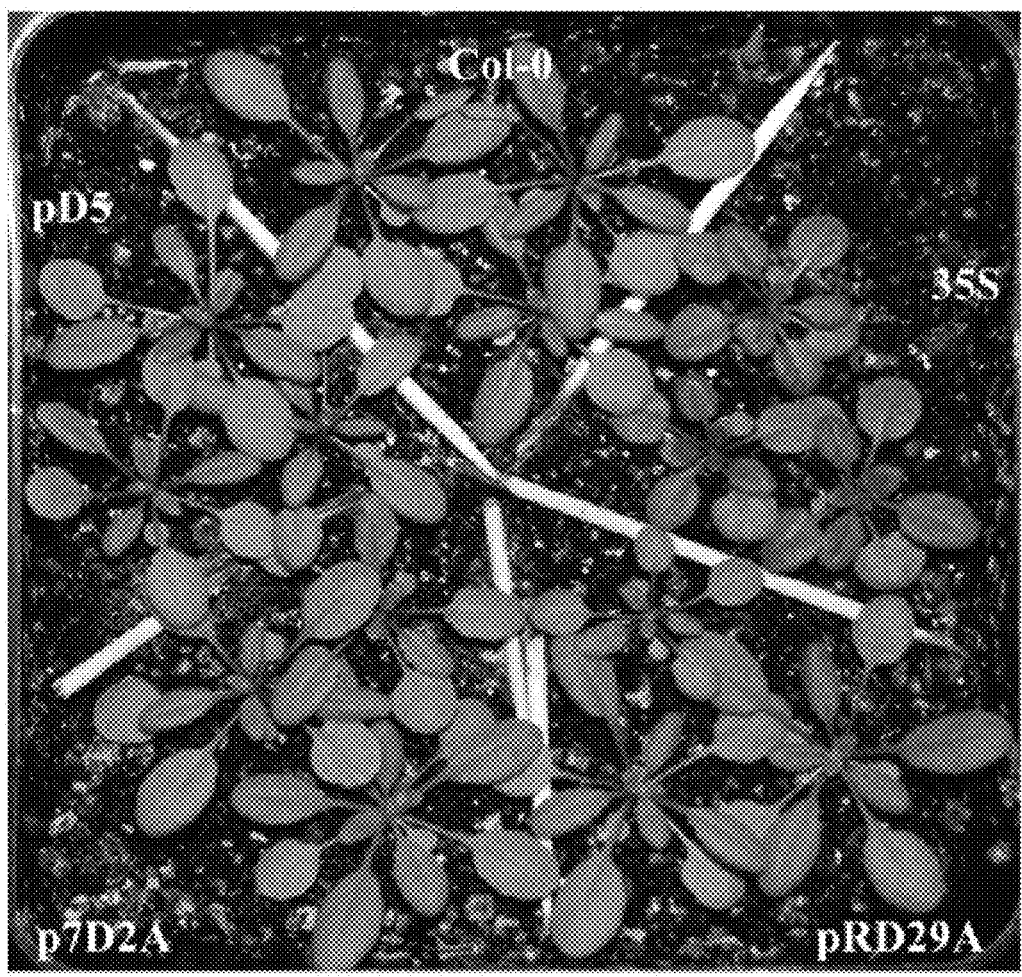

FIG. 4A-4B illustrates growth of transgenic plants that express XERICO driven by drought-inducible promoters. FIG. 4A shows seedlings subjected to drought stress treatment by growing the seedlings on a media supplemented with PEG at −0.7 and −1.2 Mpa. FIG. 4B illustrates growth of 21-day old wild-type and transgenic *Arabidopsis* plants grown under no-drought stress conditions. The Col-0 plants are wild-type control plants. The 35S plants are transgenic plants that constitutively overexpress XERICO from the CaMV 35S promoter. The pD5 plants are transgenic plants expressing XERICO driven by drought-inducible promoter D5. The p7D2A plants are transgenic plants with XERICO driven by the 7D2A promoter. The pRD29A plants are transgenic plants with XERICO driven by the RD29A promoter obtained from AT5G52310 (RD29A refers to RESPONSIVE TO DESSICATION 29A). The transgenic plants with constitutive overexpression of XERICO (35S) were small compared to control or other plants with drought-inducible XERICO expression.

Figure 5:
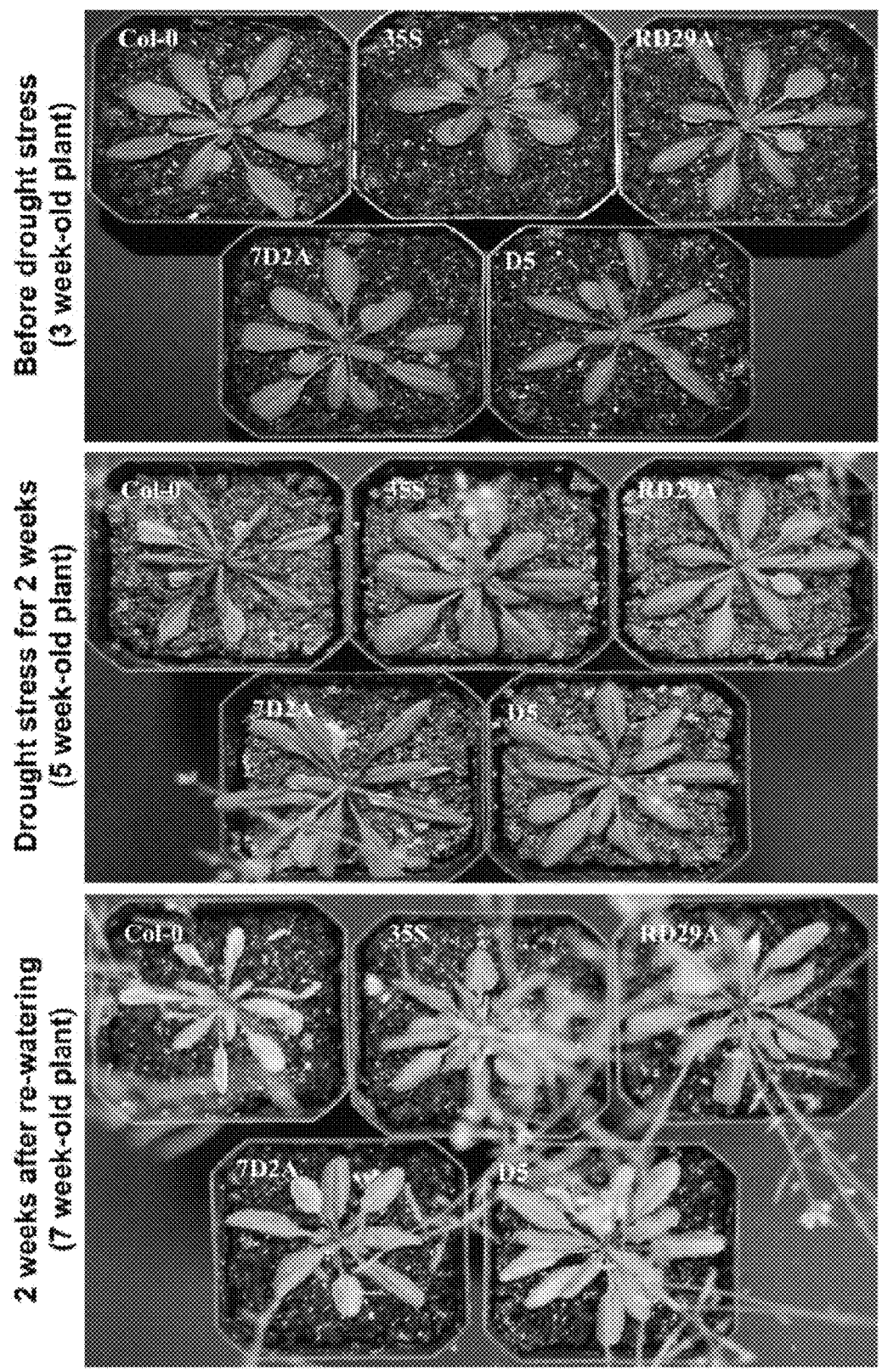

FIG. 5 illustrates drought tolerance of transgenic plants over time where the plants express XERICO driven by drought-inducible promoters, but the control (Col-0) does not have any of drought tolerance constructs described herein. The top panel shows 3-week old seedlings with watering (before drought stress). The middle panel shows the plants after withholding water for 2 weeks. The bottom panel shows the plants after re-watering for 2 weeks. The plants transgenically express XERICO driven by the 35S, RD29A, 7D2A, and D5 promoters, and their growth is compared to that of wild type (Col-0) plants.

Figure 6:
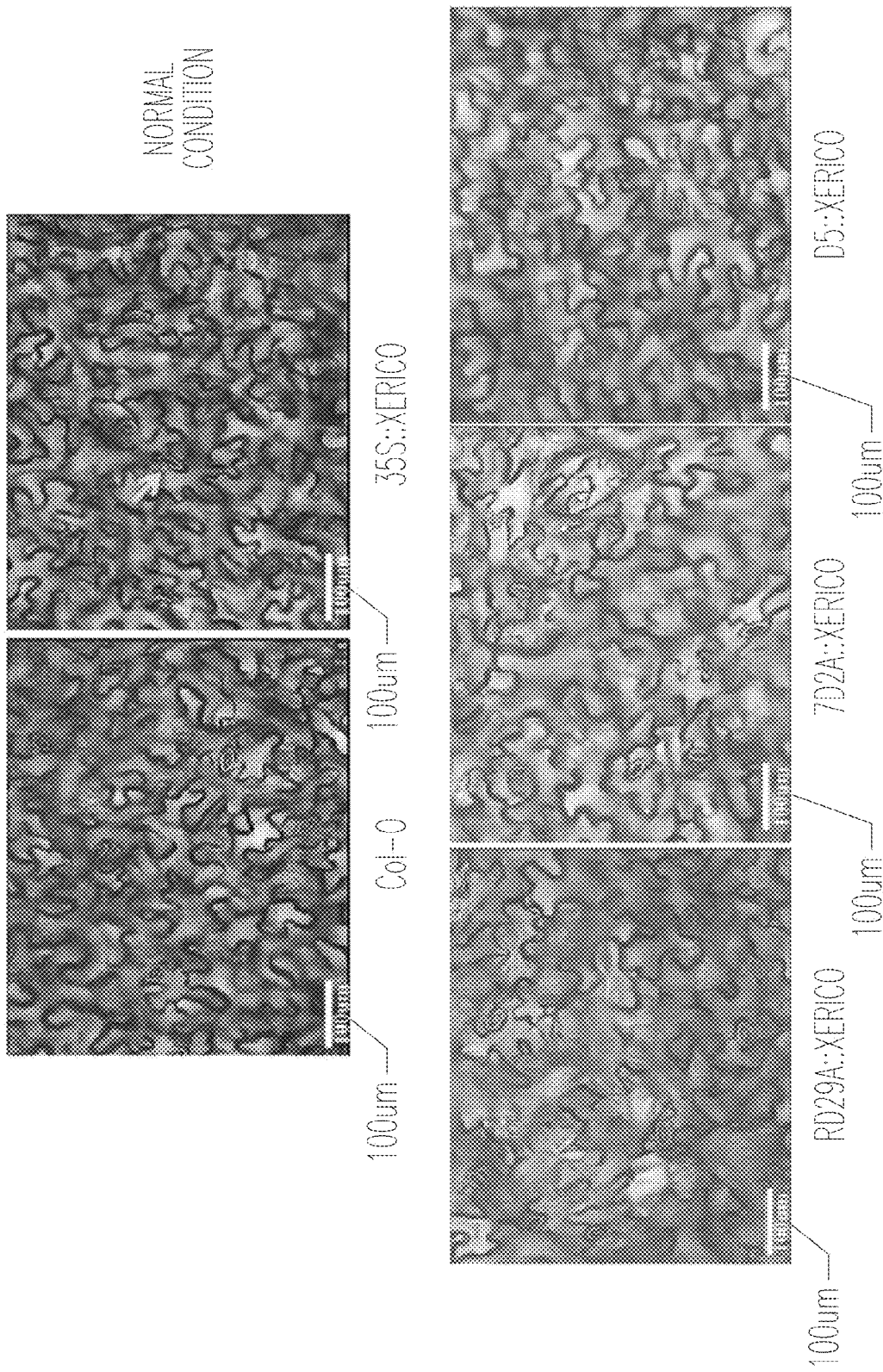

FIG. 6 shows photomicrographs illustrating open and closed stomata under normal (i.e., no drought stress) growth conditions. Stomata are closed in transgenic *Arabidopsis* plants with constitutive overexpression of XERICO (35S:: XERICO; arrows), while those of wild-type control (Col-0) or the transgenic plants with the three drought-inducible expression (RD29A::XERICO, 7D2A::XERICO, and D5:: XERICO) remain open under these normal, non-drought conditions.

Figure 7:
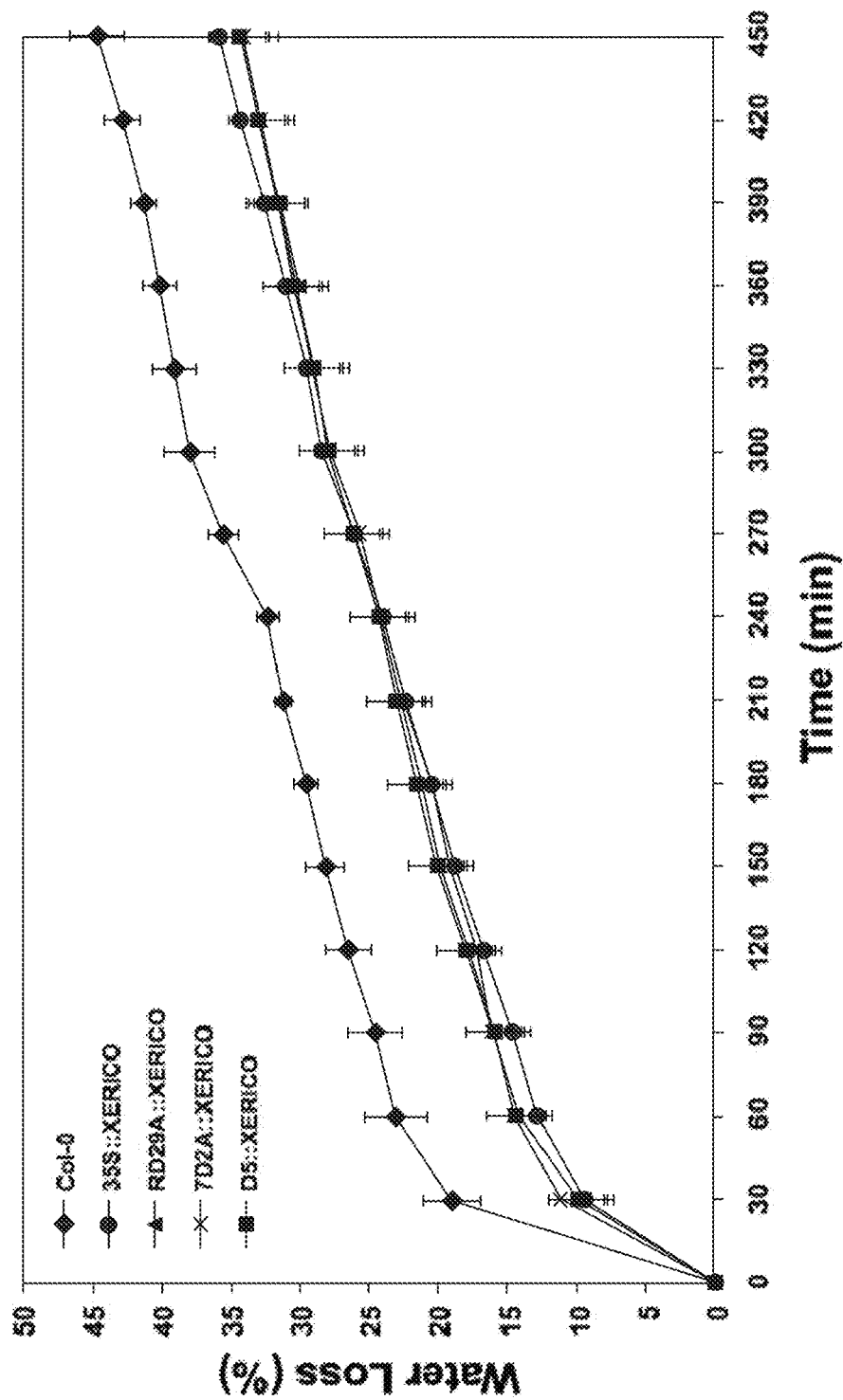

FIG. 7 graphically illustrates the percent water loss of control plants (Col-0. Diamond symbols) compared to transgenic plants that express XERICO driven by different promoters (35S::XERICO, circles; RD29A::XERICO, triangles; 7D2A::XERICO, X-symbols; and D5::XERICO, squares). As shown, plants expressing XERICO from drought-inducible promoters exhibit reduced transpirational water loss compared to wild-type control. To measure the transpiration rate, detached fresh leaves were placed abaxial side up on an open petri dish and weighed at different time intervals at room temperature. Leaves of similar developmental stages (fifth true rosette leaves) from 4-week-old soil-grown plants were used.

Figure 8:
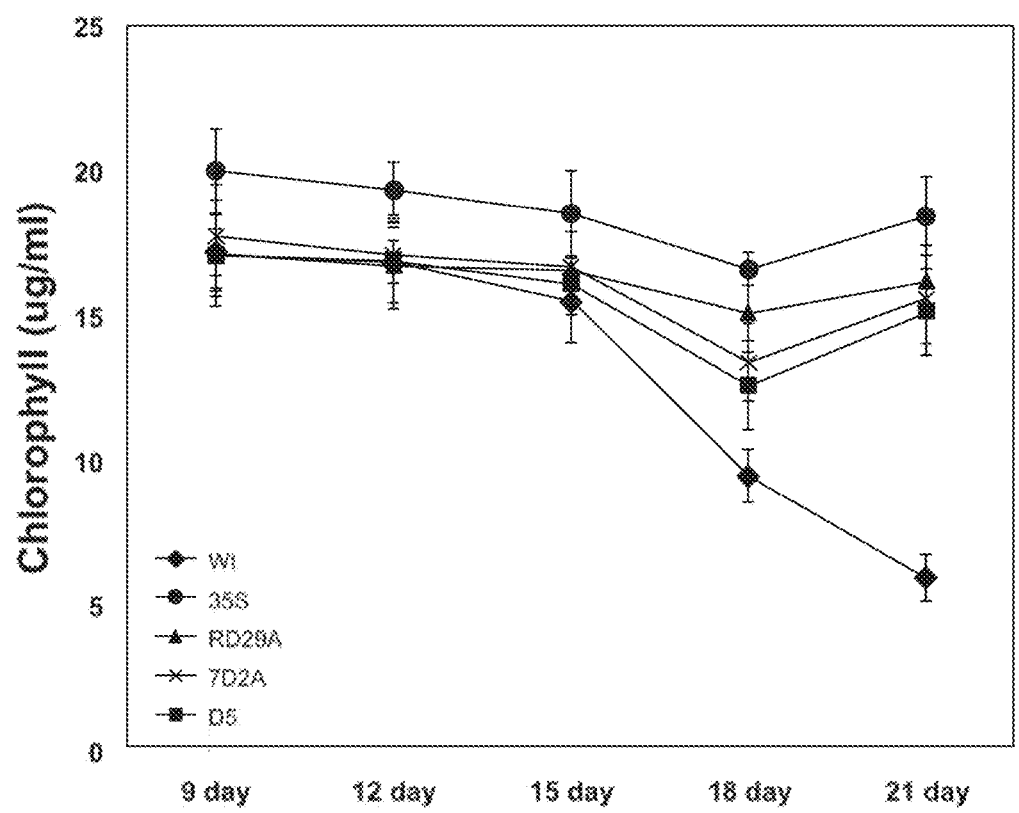

FIG. 8 graphically illustrates the chlorophyll content over time of control (Col-0) and transgenic plants that express XERICO driven by drought-inducible promoters (35S::XERICO, RD29A::XERICO, 7D2A::XERICO, and D5::XERICO). As shown, the transgenic plants with drought inducible promoter-XERICO constructs exhibit reduced loss of chlorophyll over time compared to the wild-type control. To measure the chlorophyll contents of plants, fresh leaves were collected from different drought treatment condition. The leaves were sampled every three days after growth of the plants at nonlethal soil moisture levels that were above the wilting point (9-day-old plant).

Figure 9A:
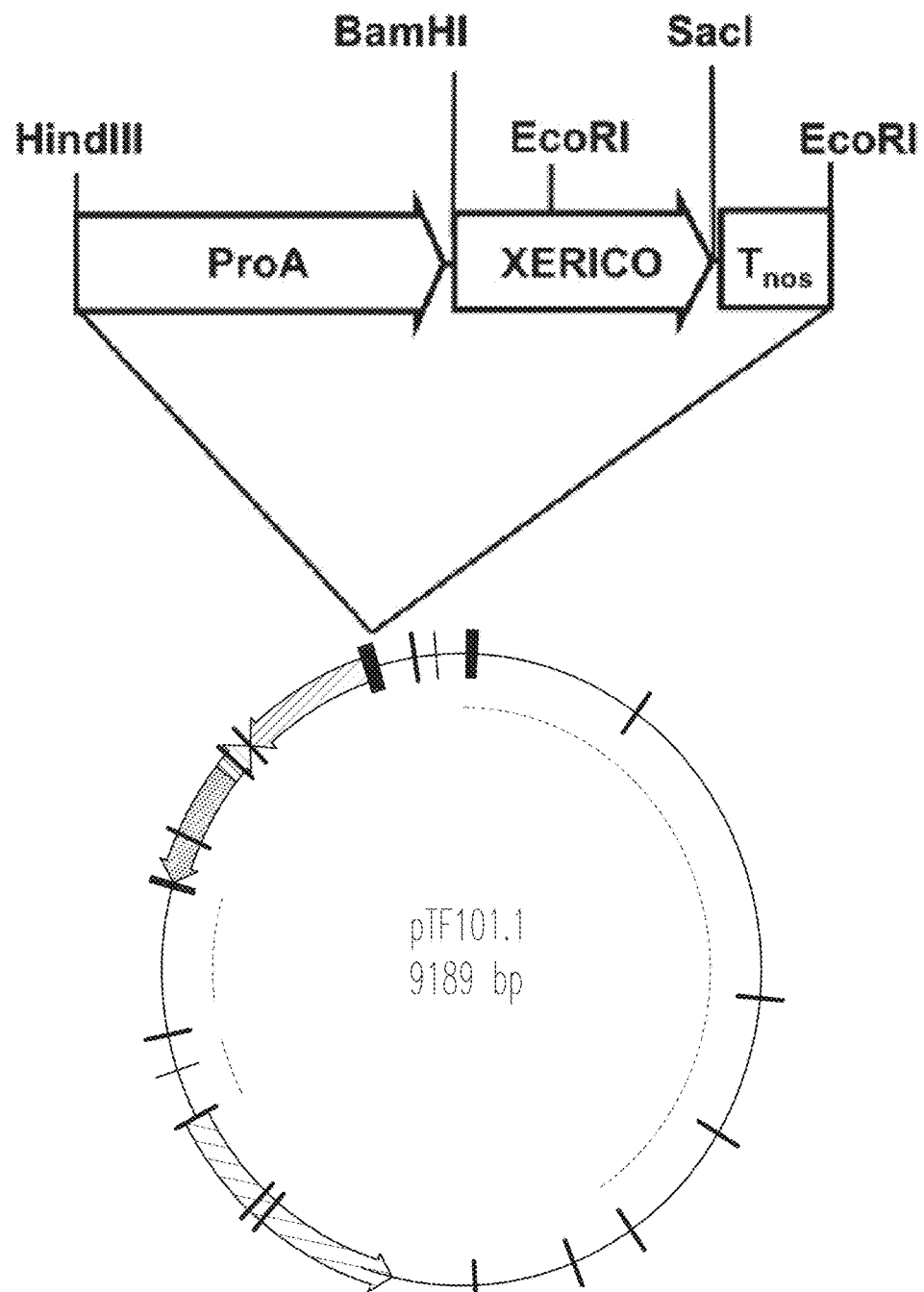
Figure 9D:
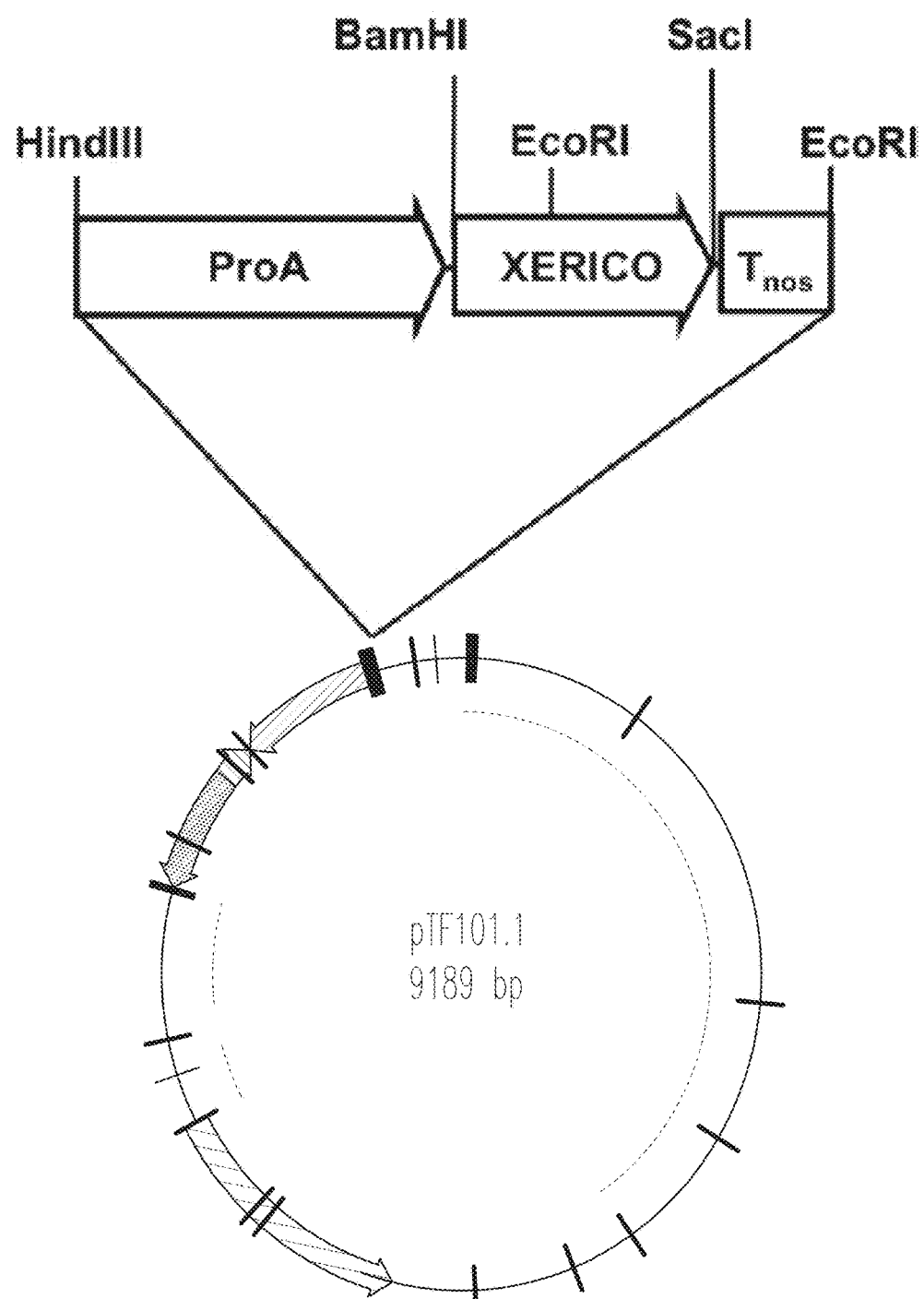
Figures 9E, 9F:
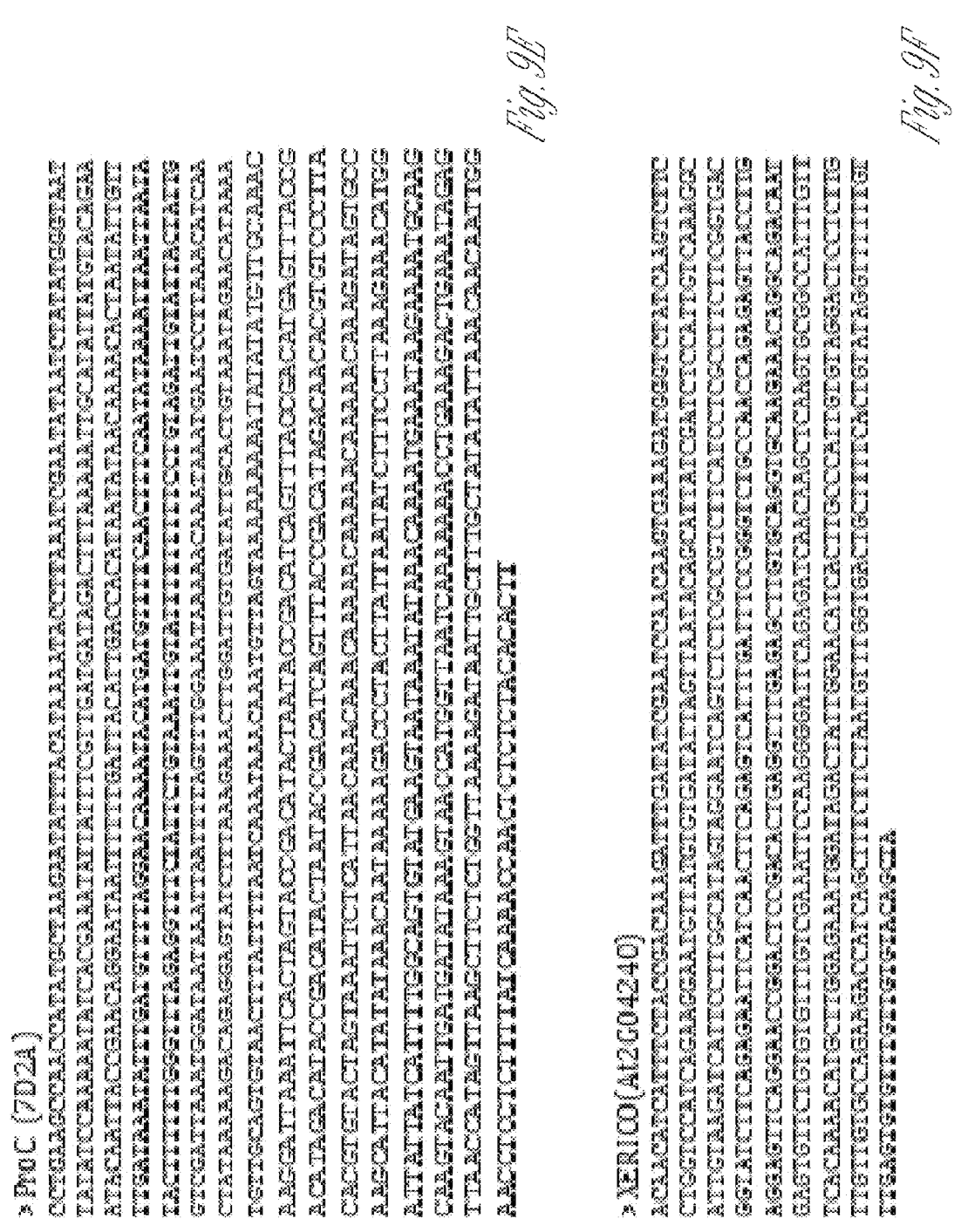

FIG. 9A-9F illustrates types of XERICO constructs that have been generated for use in plants such as corn. FIG. 9A is a schematic diagram of an expression cassette and a pTF101.1 expression vector that expresses XERICO. FIG. 9B shows the nucleotide sequence of the CaMV 35S promoter (SEQ ID NO:20), which can be replaced by any of the promoters described herein). FIG. 9C shows the nucleotide sequence of the XERICO coding region (SEQ ID NO:21). FIG. 9D is a schematic diagram of an expression cassette and a pTF101.1 expression vector that expresses XERICO from a 7D2A promoter. FIG. 9E shows the nucleotide sequence of the 7D2A promoter (SEQ ID NO:11). FIG. 9F shows the nucleotide sequence of the XERICO coding region (SEQ ID NO:21).

DETAILED DESCRIPTION

Drought-inducible promoters are described herein that induce expression of factors that provide drought tolerance to plants. The promoters described herein are induced to promote expression of gene products in plants during environmentally stressful conditions such as drought. Although workers have identified some gene products that can help plants survive under such conditions, constitutive expression of such gene products is often not beneficial to the plant. For example, although plants expressing XERICO and related RING-H2 type zinc finger encoding proteins exhibit a marked increase in their tolerance to drought stress, constitutive overexpression of XERICO throughout development results in smaller growth of the plants. As illustrated herein, plants expressing XERICO driven by the drought-inducible promoters described herein grew normally. Hence, the methods and constructs described herein can be used to generate healthy, productive, drought-tolerant plants and crops.

Drought Inducible Promoters

The drought inducible promoters are provided in nucleic acid segments that can be linked to heterologous nucleic acids segments that, for example, encode polypeptides that minimize or counteract the effects of drought upon plants.

Promoter regions are typically found in the flanking DNA upstream from a coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Promoter sequences can provide for gene expression of heterologous DNAs, that is a DNA different from the native or homologous DNA.

Promoter sequences can be strong or weak, or inducible. A strong promoter provides for a high level of gene expression, whereas a weak promoter provides for a very low level of gene expression. An inducible promoter is a promoter that provides for the turning on and off of gene expression in response to an environmental, developmental, or externally supplied stimulus.

The promoters described herein are environmentally inducible. In particular, expression of operably linked sequences occurs when a plant with one or more of the promoters is subjected to drought conditions (drought stress).

Drought stress occurs when soil water potential is too low to support normal plant functions. Drought conditions and drought stress conditions are affected by the electrolyte concentration in the soil. Soils with high electrolyte concentrations require more water than low electrolyte soils to support normal growth, which is why salt and polyethylene glycol (PEGP in the soil can create drought stress even when soil water content would otherwise be adequate. The water potential for a given plant species (and even for a given individual) that is adequate to maintain normal function varies. Some plants, like sorghum or pearl millet, tolerate fairly low soil water potentials that would damage other crops like corn or soybeans. Drought can affect plants more severely at certain stages of development than others. For example, small seedlings can be more sensitive to drought than more mature plants.

Drought conditions include a soil moisture level that was nonlethal but where wilting of the plant can occur. The permanent wilting occurs when the volumetric water content is too low for the plant to remove water from the soil. About half of the water in the soil at field capacity is held too tightly to be accessible to plants. The soil is considered to be at a permanent wilting point when the water potential in the soil is at or below −1.5 MPa, so the permanent wilting point is the water content of the soil at −1.5 MPa water potential. See website at decagon.com/support/datatrac-3-online-help-files/how-do-i-graph-plant-available-water/plant-available-water-how-do-i-determine-field-capacity-and-permanent-wilting-point/.

"Field capacity" is the amount of water that fully saturates a soil at equilibrium. In the USA and some other countries, the soil is considered to be at field capacity when the water potential in the soil is at about −33 kPa. Field capacity is not the same as saturation. When the soil is saturated, all the spaces between the soil particles are filled with water. When the soil is at field capacity, the spaces between the soil particles contain both air and water. The structure and texture, of the soil determines how much water can be held in the soil. Field capacity can be easier to measure than water potential because water potential also depends on air humidity, so researchers often substitute field capacity for water potential. Water potential is maximized when the soil is at field capacity and the humidity is 0%. Field capacity is measured, and the plants are observed for drought phenotypes under a given field capacity and humidity. See website at icrisat.org/what-we-do/learning-opportunities/lsu-pdfs/Soil %20Moisture %20-Calculation.pdf. For example, drought conditions can occur at 10% field capacity, at 20% field capacity, at 30% field capacity, at 40% field capacity, at 50% field capacity.

Drought conditions can be maintained by sustained low soil moisture levels (e.g., while replenishing the evaporated/transpired water for an extended period of time such as 1-10 days). Drought conditions can include lack of watering for at least 1 day, or 2 days, or 3 days, or 4 days, or 5 days, or 6 days, or 7 days, or 8 days, or 9 days, or 10 days, two weeks, or three weeks. Drought conditions can also include exposure to dehydrating substances such as salt or polyethylene glycol (e.g., soil or medium supplemented with polyethylene glycol (PEG) at −0.5 to −1.2 Mpa (or at −0.7 Mpa to −1.2 Mpa).

The promoters can have any of the following nucleic acid sequences.

The D1 promoter associated with the *Arabidopsis thaliana* AT1g67870 gene has the following sequence (SEQ ID NO:1).

```
TGTTGGGGCAAAATTGATATGTAAGTTCGTCTATGGGAGGGAATTAAGTT
TCCGCTGAGTAATAAACAAACAAGTGCAAACCTAGGAATTCAACACCAAT
GTAATTTTTTATAATTTTGTAGGACTCTTTAATAGTCAAGTCAGTATTTA
AACCACAAGAGTCGGTCAGAAACCAGAAAAACTAGAAACAAGTTATGTCA
GTTCTAAGAAGAGAGATGTGCAATGTATTCGGCAATCGGGTATATCATCT
AACATTTTAGCCAGTGAAAAAAGAGAAAGATATGAGGATTTTTCCATTGT
TCAGTAAGCTAAGAGAAGACAGTTTCATTAAAGAGTCGAATAGAATGGAT
ATTCTCATGAAACTGAGAAGGTTAAGTTTTTTTGGGGAATACTTTGCATG
CCTTTATATAGGTGAAGAGTCATGTTGCATAGCTCCGAGGCATTTCAGCT
TATAAGTATCCATGTCTCGACTCATATGATGAATGGACTTGATGAAGGGA
CTAGGCAATCGATCGTCAGTGCGGGTGAATTTTGACGTCTTGAGTCCATC
CGACCATTCAAAAGAAAGTATTCTTCTTACCACGTAGCATGTGACTTTAC
CTAGAGTTCGTGGAGCACAAGTAGAACAAATAGGATTATGCCTAAACACC
TTTAGAACTAGACCAAAGGTCAAAAACTATCAAAACAAGTTTTTTACGCT
ACATGGTTTACATAAAAAAATTAAGTGATACACTCAATGATGAATAACAA
TATTAACCCAAACAAATTTGATATCAAAACACAGTATAACCAAAATCAAA
ACCGTAGTGGAACTAAACTAGATTATATAATATGCCTCCATAAATACTCG
GATTTTCCACGTGAATTGGACTAATCATTAATTAGGAAGAACGGAATCAG
AATAAATATGTCTACTCAACTTTCGGTATGGTGGTGGTAGAAAAGAGAAT
AAGATTCAAAGCATATTACGAATTATTGCCATATGGGATCATATCTAACA
CAAATTTAAAAGAACACTCTACTACTACAGTACAAAATTGTATATATATA
AACACCTGAAAGATTTTAATTA
```

The D2 promoter associated with the *Arabidopsis thaliana* At2g18050 gene has the following sequence (SEQ ID NO:2).

```
caccttgaaacattaactccgtaattaatttagtcttgcaattttcata
aattgtttatatatgtcgtaacacaaaatttgcgaacggttaataacttt
actagataaaacctctctaaataggtagatgtgaaaaataaataaatttt
tgttttaataaattttcaaatgataatctatatatattttatttaatat
atattttctaaaaccaaatttcaatcttacctttctaaaaccatattgt
taaaaactaaagaaaaagttggaccaagcaaagcctctcggtaaatgtgg
taaataaatagaacgatataactgagaagaagaaaataaaacaaaattaa
gaaaataaaaagataaacatatttaagttacaatatttaaaaatattaaa
acacttcttttaagaacaaaatggggaattttatttatgtttgaatag
atcaacaattattaatagaatgagtttagtttaatatatattaaatataaaa
``` aattgaatatataaacaattgttttatgtatatattttttttttgatagg gttaaggatttttttctattttttgttttttaaatgtaataaaatttgaaac acatgtaaatatcgtattagtaaataccgaccaaaaaaaatattgtatta gtaaatttgacacatatcgcaattttttgtgagctaacaattttaaaaatc aaataagatgacgaacaaagctctggtttaaactttctcccatcaatttt ttcattaaaccaaatttaaccaattatttggcctaataactgcgtctacg ttattaagaataagaacttattttgtgtttcagtagaaaacacactcgtt cacaaaatgcctagtaagagtaaaggacgatcaccgccaccaagtgtgtt tctcggataaacacatggaatccagccattacttaaacgacacgtgtacg ctcatgatttattaatgcacacgtaatcgatcctctgacaaaaaccataa cgaatacagaaaacacacgaatacacttccctgcgctataaataagctag cacgaaaaaatttaacagatagagacaagacaagc The D3 promoter associated with the *Arabidopsis thaliana* At1g10070 gene has the following sequence (SEQ ID NO:3).

attctatttgccagactctacggcggtatattcgcttttagaaaaaaaac aattttgtcgaaactttttttttttttgtaaatattgtagattccacacac aagactgtctaagattctttgataagacacgacaaatgcgatttaagatt tttcaaagaaatgaggttcgttgattgttccactaggtttggtatattta taatttgaattttttttttttaaagatatttataagaaaacgaaggagtgt gctcgcgtcaagtgtgtactaatagtcgatgacactagtgatacgacgat actggaaagggacatcaatattcattagtaagccatcttagcaaaaacgt tgttatcagataagaaaagttctcagactgacgtggctgtcaatctccac aacgtgtttatctcccatttgggtagttacggacaaagacgttgaaaaga caacaatatggtctaaaagattgacatggaaagaaaattgtttatccgac aaagacctcttggtccaacgtggctttcacatcactagtttactatttca catctcatggaaaattactgaaattagtacttgtctgtattttgtttttt cgtcaagtatttgtttgtatactttaggtaattgcgtgccgaagaaacat tgctaaattgatatttataccaacttacaatagtttacagttcaaaaata gaaatctccattttgaagatacaccactaattttcttcatttatttaccc cataagagaacgagaaaagaacaatagtccgttgatttcgttaaaatcta gtttcagaaagacacgtctagatctgtctgatcagggcagatagacacaa gtgacgaagcaaaagaaacacaaaaataagataagaactcttaccactaa aagataaaaataagaaaaaaataaaacaaattcaacgatttgccaagat aaaagcagacactgtacataagctccgca The D4 promoter associated with the *Arabidopsis thaliana* At5g25110 gene has the following sequence (SEQ ID NO:4).

gttgtttatattgttactaggcctttgtataaataccaaatactttgatt atttttttactgatttcatgtcaaacaaaattccaaacaacttaaaggaa aaagcttactcgattggaataaaaaattgtacgtttaacaaaatgatatta gtgaaataaataaaccagctcaacatttaaggatttctacgtgtatatac agtaatcgtgtttagtattaattagctatagtttagcctcaaaaaacaaa gatccaaaacaacatgacgaaattgacttccacatcgtgtcctttctcgt cgacataaaaactttaatatatagatgcatgtataagtatactcactatt tgtgtcattagtattttcttttttgatacttggagctaatgacaaaaatt ccgctagaaatatcttctccaacgatagctacaaacaaatactaccattg cgtcatcatcacttatttatattcgatatttcagtcaacaacactaatct cttttcaccaaaatcttttggactattattacaaatgaattaaaaacttgga cccttaataacatatttgtttcattaaatctatacaactcttattaaaaa tgatattttcttaaatcaaaaattaatcaaaattaaggtaggctctagag gattgcatcatttgcccacccacattagcctgccattattattggacggt aacaaatttccttacaccaatttaaatggtaagttacaattattattaacat ttctatataaaatagtttggttatttacattaatttttatttaatactat aaacttaaaaattcaatgctgaaaagtgtaacggaaagagggacattaaa tatatgttaatataataagtatatttactatttaaaaaagacttatgtaa atacatattgtatagagagaaaaataacccatagtataaaaacttgcatc tctaaaaccgcagcattgataataagagtctctttcttcttaagtatctc ttaattaacccacataatatatttacaagtggccgcctcatacatcccct ctcaagtcctttgcttc The D5 promoter associated with the *Arabidopsis thaliana* AT1G07430 gene has the following sequence (SEQ ID NO:5).

atcttaacttctgcaacgaatcaatgtattaatttataggagatccggat aaaattatggatatatgcacgctacttctttcatttttaattaggtaaat ggttataactttattttatatatcaattaaatgattttggtatgagatta ctagtacactttctttgcaaatgttttaaacacgacaagacaaaaatatt acaagcatattttggtaaaaaatatcataagctttcatatcaaaatcatt agttatgatgttagatttttttttttttttttttaacactacaaaaagctc tggtcttaatatgttagaaattttagtccaaaccagcctacagaggattt agctaaacaattcccaagcacctttaagtgttaaccgaaataacgtaat atgatgttaaaggttacataaaaacaaaactaaagaattttcatatgaaa agttaacgtacgtgtcttagtgtaacctaattttagttcacagtatataa attctttaatgagatgatcgcaaaatcgctgtatacaatttcgtacttaa ttcgttagtcttgaaaagttgacctaatttgatcaaattaaggttaact acaataaaaatttaactaacgtaatgggattctttaaaattaaaaaatcg ttgattagatagatattttatcttaagggagacacagagacaatttgga caaaaaaggtcttcctgagaaagaagtggaccacaatcgtggcgcgaaag gaacttcctcctccctctgttgccttgtcattgggccacgtatatctcc acctgatcgtgatgcttacgtggtccatttctagatactatagtgaccag atcaacggtcaagattgattctaatttagacgaaagaccaacacgtcacg tcgctagagtaaaagatttttttgaaggcggagggagaaaaatcaaaagtt -continued aaaagtaatttgaaaacgaggaagagaaaaaggaattttaaaatgtttaa tgaagcggtaggccgcatgggtatataaatgggcacgctttgtaacgtgt aacgat The D6 promoter associated with the *Arabidopsis thaliana* AT1G56600 gene has the following sequence (SEQ ID NO:6).

ggtgaattaaaggtagtgaacgccacttgcggatgcatggtacatcgcgg caaattttataaaaatgtagaatggggacttttttcatttatttaataaat aatccatttatttggctttaagaaacctatcaattaccaaaaaagaaga aaactagaagaaaaaaaataaaactcgagatgtgagtaatttcatagac ttgattggtttccgaaaaatttaaaagtataattgataaaatgttagatt aaaagttaatttaatagctataaaaaatacaaattgagaggaactacaca catttttttttttttatggaacctaacacaaattttttttttttgttgaat gcagataagtaatacctacttgacagaaacaaactaaaataaaataaaaa taaaaataacgaaacataaccttatgagtttttgagtcatgcaattaaaa aatatatgattttaacgtccacatatgccgtaaatagtcggtcggtca tcggtcagacaaactaccataggaaagaaatttaaacatggaaatagac caaacgggaaatgggcccaacaagacttttccttgtccacgtgtatcatc accgcctactacgttccacgtagacacgtgtccacataataaccaatcag aaaatcccacactaatatagtgtattaaatacccccatacgacgtcgtata tctgaagtggaacccattgataaacacataaaaatgaccgatcaaccacc acgagctcgatttaaaaaccttgatgagtcgaacagtctagatactgaca cgtgtcgttatgtaacgccgtggcagcacctggattatactgggacccac tgtaaatagttaattcaaaacgaagcttcgcgcgcgtatcctaaaccgtt agattccaccatattgttgaatagccgttggatcaaaatctttctctgga aacgtttagtagtcggtcgtatttaattatccaaagtaattagcgattaa tcttttaattaattaagacaaaatcttatataaagcaccattaagcatca cccacat The D7 promoter associated with the *Arabidopsis thaliana* AT5G18130 gene has the following sequence (SEQ ID NO:7).

taatctaaaagctaccaaataacctaatattagtgtttttgaataattgc ctttgtattttacaagtattgatttagttgattttcgacgaaaagctttc ctcaaattttttaatattatcacctatattctcattacgtaaaggatcat atcaaggatgataagaaattataataagaaaaataaatgattctaggtgt ttattaaatgactccctcttctacacttgttaaatgaaaacgtagttgc tttttcctggaataacactaataattccgagcaagcaacctccactacta ctatcttttatcattttatccctagaaagggacttaaacttgtaactt gtataacacatcacatcatcttcttttttttcttcctttcgttttgtggtt aatttggtaatttactttcgatgcaataaacaagccgaaaatatgaaaaa cgttcatctgttaattagtaccaagtttatacttgaagcttgaatatagt -continued tatctacaccaataattttgtattattttacaagaaatttaaatacccg cttaggtagacgtcttaatccataacttatagaaacttaaaaaaacttggt acgaaagattcttcttaatcatcagctaactaaatcttgtttttatcact aaatattttattagcaatcaaatattgtggaaaatgaattagcgtgttaa ccaatgggtttggttataggaaatataaaatatcaaaggagagaagggac cttgtcaaagaagacaatcgatacttcttaacgtgggtcctaaaatggca acatcttttttttgtcatttcatgtgtgtagataagctctaatttcttac ctcaccaatggttatatgaatataaaaatgatttctgtaaacaattctgt tgaaattatgtaattatcattatatattaaatcactaatcaacactttat acttttttaacagtgacaacactaaatgcgtccatttaagagtttcgcttt tccgtctcttcttcttctttgatcatctatttaaggatctagagaaacca cttcg The D8 promoter associated with the *Arabidopsis thaliana* AT2G25625 gene has the following sequence (SEQ ID NO:8).

atgagaagtaaacatagtattttgaaaaatagcaagaaaggaaatctgaa attttagactaatagcaaaaagattttgagttaagttgacaaaattgaat tttagtaacttgggaccttttttacatctttttttatataaaaaaagtcga cacatgagatattacttataaaattaaaaatacattattttcatgaatat ttaatagagtttatgaatttctcacatatgttaattattaagtgctgaaa aatgtttaattgttttctgtataaatgttaagtactgaaaaatgcttgg aatgttttttctatatttatatctctgctatttatatgtgtgatttagtgt tatttagggcattaaatataagatattaaaatattaaatttttctataat ttaaaaataagtaaataaacatgttgtagaccgtaattgccagattattt gtgctgtttcctaaatacttttacattctttgatggtcaccaaattaact ataagaaaaattaggactcagtctcattaattttcggaagagaaaaga atcagtctcatggtagttgttaggaaatatttgaatattgtttcgccatt agaaacttttatgtggatttttttcctgaaaacgatggttactattaat taaacggaccgacaagaaccttgttgacgtggtaacaagtgatgacacat gctaattggccatcattgtcaaataatttgttcgcaaggcgtgatacgtg tacgttgttattcagacgtagcaaacagattcacgacttttgttcaattt gtctttgtatggagtatggacctaacatctccaacggaccaatgctattg ggtcaagtccatcttttctaggttaagttcattcttggtctttagttaa gtatagagaaagaacatattggaagaaaaatttagatgtggtttgtattg catgcgcatatgaaatgtaataatttgaggatacatatatagtaagaaaa aatgagtgacccaagtaagaatg The D9 promoter associated with the *Arabidopsis thaliana* AT2G46680 gene has the following sequence (SEQ ID NO:9).

ctattatatgccatttctatttagttttttttctaaaaatatatataaa tatggtgttgttaacataaaaacagaaaaaaagaaaaatttagaaaattt -continued
```
tctcaagaatcattatatctgtgatttatcatataagttcaaatatgata
ttagaaacaaatagtttacgagtataatagtattgtcaattttttcaatct
gaagtaaatatcttttttgtaaggaaggggtcaacaaatgatcacaacaga
gttggcaaaaagttatcaaatcgcatgcacggaagttttacgtgtggtga
aggtaaacttgtattacacttatctataaaaattagtttaggctttgatt
ctaaatcaaatctccgattagaaaaaattgcgtaagcaaatagctggaaa
aaattgtatcccatcatacttaagtcacaatgttttgttttttgagatttg
tgatgtaatcaatatatgttttacaatgcaagtataataatattaaagtc
acattctaagaaaattatgatttgtgtcatacgtatacaaaaacacccgt
cacacatcctgacttctgaacgttaaatctgtcgcacacaatcataaaaa
tttaaaaattcaccagagatgtactgaaaagaatataattaatcacatga
tgatatatgcataggagatgaggattattcattttctgaaattccctata
tgaaccattataattgtttagtaatcagttcagaaatgctaatcattata
tgaaccattataattcccttcattttatttaagatccacttaacaggat
ttgttaatatgcacccacatcactaaatacattggtacgcaaccgttgtt
ccatttccattttcacatcgaccagaatgtttactatgcggtaaattgtg
tagtatgcagattttttttgtatcatttaattttctaacacttgttaagtc
gaaactaattttgtcacaagtaaaagaaataaaaaaggtggaaattatta
atcagtagttagatgattagtttcgagttgaaatgaaactcgacttaaca
agtgatagcgacgactctagaaacagccaaaatccgccctattgctacct
gtcgacccacaaatcgtttactcaaaaatgaataaaaaatttacgataaa
gcaaacccaaagttatatcttattat
```

The RD29A promoter associated with the *Arabidopsis thaliana* AT5G52310 has the following sequence (SEQ ID NO:10).

```
GAGGAGAGAGGAGGTAAACATTTTCTTCTATTTTTTCATATTTTCAGGAT
AAATTATTGTAAAAGTTTACAAGATTTCCATTTGACTAGTGTAAATGAGG
AATATTCTCTAGTAAGATCATTATTTCATCTACTTCTTTTATCTTCTACC
AGTAGAGGAATAAACAATATTCAGCTCCTTTGTAAATACAAATTAATTTT
CGTTCTTGACATCATTCAATTTTAATTTTACGTATAAAATAAAAGATCAT
ACCTATTAGAACGATTAAGGAGAAATACAATTCGAATGAGAAGGATGTGC
CGTTTGTTATAATAAACAGCCACACGACGTAAACGTAAAATGACCACATG
ATGGGCCAATAGACATGGACCGACTACTAATAATAGTAAGTTACATTTTA
GGATGGAATAAATATCATACCGACATCAGTTTGAAAGAAAAGGGAAAAAA
AGAAAAAATAAATAAAAGATATACTACCGACATGAGTTCCAAAAAGCAAA
AAAAAAGATCAAGCCGACACAGACACGCGTAGAGAGCAAAATGACTTTGA
CGTCACACCACGAAAACAGACGCTTCATACGTGTCCCTTTATCTCTCTCA
GTCTCTCTATAAACTTAGTGAGACCCTCCTCTGTTTTACTCACAAATATG
CAAACTAGAAAACAATCATCAGGAATAAAGGGTTTG
```

The 7D2A promoter is a synthetic promoter that was generated by inserting two types of abiotic cis regulatory elements into the native XERICO promoter. These two types of abiotic cis regulatory elements are the DREs (drought response elements, TACCGACAT, bold in the SEQ ID NO:11 sequence shown below) and ABREs (ABA response elements, ACACGTGT, in bold following DREs in the SEQ ID NO:11 sequence shown below). The 7D2A promoter has the following sequence (SEQ ID NO:11), where the two underlined sequences (ACTAGT) are SpeI restriction enzyme sites flanking the DRE and ABRE drought response elements.

```
CCTGAAGCCAACCATATGCTAAGAATATTTACATAAAATACCTTAAATCG
AATATAATCTATATGGGTAATTATATCCAAAAATATCACGAAATATTATT
TCGTTGATGATAGACTTTAAAAATTGCATATTATGTACAGAAATACAATT
ACCGAACAGGAATAATTTTTTGATTACATTGACCACATAATATAACAAAA
CACTAATATTGTTTTGATAAATATTTGATGTTTTAGGAACAAAATACATG
ATGTTTTCAACTTTCAATATAAAATTAATTAATATACTTTTTTGGGTTTA
GAGGTTTCTATTCTGTAAATTGTATTTTTTTTCCTGTAGATTGTATTAC
TATTGGTCGATTAAATGGATAATAAATTAATTTTAGTTTGGAAATAAAAA
CAAATAAATGAATCCTTAAACATCAACTATAAAAGACAGAGGAGTATCT
TTAAAGAAACTTGGATTGTGATATTGCACTGTAAATAGAACATAAAATGT
TGCAGTGTAACTTTATTTTAATCAAATAAACAAATGTTAGTAAAAAAAA
TATATATGTTGCAAACAAGGATTAAATTC<u>ACTAG</u>TACCGACATACTAATA
CCGACATCAGTTTACCGACATGAGTTTACCGACATAGACATACCGACATA
CTAATACCGACATCAGTTTACCGACATAGACAACACGTGTCCCTTACACG
TGTACTAGTAAATTCTCATTAACAAACAAACAAAAACAAAAACAAAAACA
AAGATAGTGCCAAGCATTACATATATAAACAATAAAAAGACCCTACTTAT
TAATATCTTTCCTTAAAGAAACATGGATTATTATCATTTTGGCAGTGTAT
GAAGTAATAAATATAAACAAAATGAAATAAGAAAATGCAAGCAAGTACAA
TTGATGATATAAAGTAACCATGGTTAATCAAAAAAACCTGAAAGACTGAA
ATAGAGTTAACCATAGTTAAGCTTCTCTGGTTAAAAGATAATTGCTTTGC
TATATATTAAACAACAATTGGAACCTCCTCTTTTATCAAAACCAACTCTC
TCTACACACTT
```

The XERICO promoter has the following sequence (SEQ ID NO:12), with the SpeI restriction site indicated by underlining.

```
CCTGAAGCCAACCATATGCTAAGAATATTTACATAAAATACCTTAAATCG
AATATAATCTATATGGGTAATTATATCCAAAAATATCACGAAATATTATT
TCGTTGATGATAGACTTTAAAAATTGCATATTATGTACAGAAATACAATT
ACCGAACAGGAATAATTTTTTGATTACATTGACCACATAATATAACAAAA
CACTAATATTGTTTTGATAAATATTTGATGTTTTAGGAACAAAATACATG
ATGTTTTCAACTTTCAATATAAAATTAATTAATATACTTTTTTGGGTTTA
GAGGTTTCTATTCTGTAAATTGTATTTTTTTTCCTGTAGATTGTATTAC
TATTGGTCGATTAAATGGATAATAAATTAATTTTAGTTTGGAAATAAAAA
CAAATAAATGAATCCTTAAACATCAACTATAAAAGACAGAGGAGTATCT
TTAAAGAAACTTGGATTGTGATATTGCACTGTAAATAGAACATAAAATGT
```

-continued
```
TGCAGTGTAACTTTATTTTAATCAAATAAACAAATGTTAGTAAAAAAAA

TATATATGTTGCAAACAAGGATTAAATTCACTAGTAAATTCTCATTAACA

AACAAACAAAAACAAAAACAAAAACAAAGATAGTGCCAAGCATTACATAT

ATAAACAATAAAAAGACCCTACTTATTAATATCTTTCCTTAAAGAAACAT

GGATTATTATCATTTTGGCAGTGTATGAAGTAATAAATATAAACAAAATG

AAATAAGAAAATGCAAGCAAGTACAATTGATGATATAAAGTAACCATGGT

TAATCAAAAAAACCTGAAAGACTGAAATAGAGTTAACCATAGTTAAGCTT

CTCTGGTTAAAAGATAATTGCTTTGCTATATATTAAACAACAATTGGAAC

CTCCTCTTTTATCAAAACCAACTCTCTCTACACACTT
```

The promoters can provide drought-inducible expression with some variation in sequence. For example, the promoters with any of SEQ ID NO:1-12 can have substitutions, deletions, insertions and rearrangements but still provide drought-inducible expression of the product(s) encoded within the coding region. The drought-inducible promoters have at least 50%, or at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of the promoters with any of SEQ ID NO:1-12.

Nucleotides can also be absent from the ends of the promoters described herein. For example, about 1 to about 100 nucleotides can be absent from the 3' and/or 5' ends of the promoters with any of SEQ ID NO:1-12. Any number of nucleotides between 1 to 100 nucleotides can be absent from the 3' and/or 5' ends of the promoters with any of SEQ ID NO:1-12. For example, 2 nucleotides, 3 nucleotides, 4 nucleotides, 5 nucleotides, 6 nucleotides, 7 nucleotides, 8 nucleotides, or any integer between 1 to 100 nucleotides can be absent from the 3' and/or 5' ends of the promoters with any of SEQ ID NO:1-12. In some instances, 10 nucleotides, or 20 nucleotides, or 25 nucleotides, or any other integer between 1 to 100 nucleotides can be absent from the 3' and/or 5' ends of the promoters with any of SEQ ID NO:1-12.

In some instances, the promoter has less than 100% sequence identity to any of SEQ ID NO:1-12. For example, the promoter can have less than 99.9%, or less than 99.5%, or less than 99% sequence identity to any of SEQ ID NO:1-12. For example, promoters with less than 100% sequence identity to any of SEQ ID NO:1-12, can be of the same length as the corresponding promoter but have one or more nucleotide substitutions.

Construct with at Least One Drought-Inducible Promoter

The promoters described herein can drive expression of various coding regions of interest, for example, by genetically modifying a plant or plant tissue to contain a construct that includes a nucleic acid segment that has one or more promoter segments upstream of a nucleic acid segment with the coding region of interest. Any of the promoters described herein can be employed, including one or more promoter segments with any of SEQ ID NO:1-12, or any segment with at least 50% sequence identity to any of SEQ ID NO:1-12 (see description above). Such a promoter that is operably linked to a coding region of interest can be part of an expression cassette or vector for expressing any coding region of interest. The promoter segments employed are functional in plants.

A plant with a construct containing one or more of the drought-inducible promoters can provide expression of an operably linked coding region at higher levels under drought conditions than when the same plant is not under drought conditions. For example, when a plant is subjected to drought conditions a construct containing one or more of the drought-inducible promoters can provide expression of an operably linked coding region at levels that are at least about 5%, or at least about 10%, or at least about 20%, or at least about 50%, or at least about 75%, or at least about 100% higher than when the same plant is not under drought conditions. In some instances, when a plant is subjected to drought conditions a construct containing one or more of the drought-inducible promoters can provide expression of an operably linked coding region at levels that are at least about 2-fold, or at least about 3-fold, or at least about 5-fold, or at least about 10-fold higher than when the same plant is not under drought conditions. Hence, the promoters described herein are drought inducible.

Moreover, when subjected to drought conditions a plant with one or more of the constructs described herein (containing one or more of the drought-inducible promoters) loses less water over eight hours than a plant that does not have such a construct. For example, a plant with one or more of the constructs described herein loses at least about 1%, or at least about 2%, or at least about 3%, or at least about 4%, or at least about 5%, or at least about 6%, or at least about 7%, or at least about 8%, or at least about 9%, or at least about 10%, or at least about 12%, or at least about 15%, or at least about 20% less water over eight hours than a plant that does not have such a construct.

The genetic modifications involved can be accomplished by procedures available in the art. For example, one of skill in the art can prepare an expression cassette or expression vector that can express one or more promoter segments operably linked to a coding region of interest. In general, a promoter segment encoding can be operably linked to a selected coding region of interest, for example, by inserting the promoter nucleic acid segment upstream of a selected coding region nucleic acid.

Plant cells can be transformed by the promoter-coding region constructs (e.g., expression cassettes or expression vectors), and whole plants (and their seeds) can be generated from the plant cells that were successfully transformed with the promoter-coding region nucleic acids. Some procedures for making such genetically modified plants and their seeds are described in more detail below.

Coding Regions:

A selected coding region can be operably linked to one or more of the promoter segments described herein. Such promoter segment(s) can provide for expression of RNA encoding, for example, a protein that provides drought tolerance or resistance to the plant. The coding region is generally heterologous to the promoter segment(s).

For example, novel promoter sequences may be employed for the expression of a SlPP2C1 gene product or a RING-H2 type zinc finger encoding protein such as any of those described herein (and/or any with at least 50% sequence identity thereto). cDNAs encoding a SlPP2C1 or a RING-H2 type zinc finger gene product can be isolated from plant tissues and those cDNA can be operably linked to one or more of the promoters described herein. The structure of any such promoter-coding region can be confirmed by sequencing, restriction analysis, and/or other procedures available to those of skill in the art.

Expression of an RNA or protein expressed by any of the promoter-coding region constructs described herein can be confirmed or evaluated by available procedures such as Northern blotting, polymerase chain reaction (PCR), quantitative PCR and other available methods.

A nucleic acid segment encoding a coding region of interest (e.g., a SlPP2C1 or a RING-H2 type zinc finger cDNA) can be combined with a selected promoter by available methods to yield a construct of interest such as an expression cassette, For example, procedures that can be employed to make such constructs are described in Sambrook et al. (MOLECULAR CLONING: A LABORATORY MANUAL. Second Edition (Cold Spring Harbor, N.Y.: Cold Spring Harbor Press (1989); MOLECULAR CLONING: A LABORATORY MANUAL. Third Edition (Cold Spring Harbor, N.Y.: Cold Spring Harbor Press (2000)). Briefly, a plasmid containing one or more of the promoter segments described herein can be constructed as described in Jefferson (Plant Molecular Biology Reporter 5:387 405 (1987)). Commercially available vectors can be adapted to include any of the promoter segments described herein. Examples of vectors that can be employed include those available from Clontech Lab in Palo Alto, Calif. (e.g., pBI121 or pBI221). Another example of a vector that can be employed is the pCB301 vector described by Xiang et al. (Plant Mol Biol 40: 711-717 (1999)), or modifications thereof such as the pCB308.

Such vectors can have multiple cloning sites downstream from the promoter segment(s), where the cloning sites that can be cleaved by various restriction enzymes. The coding region nucleic acid segments can be subcloned downstream from the promoter using restriction enzymes and positioned to ensure that the coding region nucleic acid is inserted in proper orientation with respect to the promoter so that the coding region can be expressed. Once the coding region is operably linked to a promoter, a construct (e.g., an expression cassette) is formed. The construct can be within a vector to form an expression vector. The construct can also be subcloned into a plasmid or other vector to generate an expression vector.

Targeting Sequences:

Additionally, expression cassettes can be constructed and employed to target the encoded polypeptides of interest into intracellular compartments within plant cells, or to target the polypeptides of interest for extracellular secretion. Although, most drought-tolerance factors appear to act intracellularly there may be instances where is it desirable to secrete or sequester drought-tolerance factors within organelles or storage vesicles (e.g., to facilitate isolation and/or purification of the drought-tolerance factors). Similarly, it may be desirable to target such factors and others of interest to various intracellular compartments or to the extracellular environment. Therefore, the invention contemplates targeting the factors expressed by the expression cassettes and vectors to various intracellular and extracellular locations.

A nuclear localization signal or sequence is an amino acid sequences that 'tags' a protein for import into the cell nucleus by nuclear transport. Some products of the expression cassette may naturally have such a nuclear localization signal or sequence. Alternatively, a nuclear localization signal or sequence can be operably linked to the factor(s) encoded within the expression cassettes and constructs described herein. Transit peptides act by facilitating the transport of proteins through intracellular membranes, e.g., vacuole, vesicle, plastid and mitochondrial membranes, whereas signal peptides direct proteins through the extracellular membrane. Factor(s) encoded within the expression cassettes and constructs described herein can be operably linked to nuclear localization signals/sequences, to transit peptides or to signal peptides.

Targeting to selected intracellular regions can generally be achieved by joining a DNA sequence encoding a nuclear localization sequence, or a transit peptide or a signal peptide sequence to the coding sequence of the factor of interest. The resultant nuclear localization sequence (or transit, or signal, peptide) will transport the factor to a particular intracellular (or extracellular) destination. Such sequences (nuclear localization sequences, transit peptides or signal peptides) may be post-translationally removed by cellular enzymes. By facilitating transport of the factor into compartments inside or outside the cell, these sequences can increase the accumulation of a particular gene product (factor) in a particular location.

3' Sequences:

The expression cassettes can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of Agrobacterium tumefaciens (Bevan et al., Nucleic Acid Research. 11:369 385 (1983)), or the terminator sequences for the T7 transcript from the octopine synthase gene of Agrobacterium tumefaciens, and/or the 3' end of the protease inhibitor I or II genes from potato or tomato. Other 3' elements known to those of skill in the art can also be employed. These 3' nontranslated regulatory sequences can be obtained as described in An (Methods in Enzymology. 153:292 (1987)). Many such 3' nontranslated regulatory sequences are already present in plasmids available from commercial sources such as Clontech, Palo Alto, Calif. The 3' nontranslated regulatory sequences can be operably linked by available procedures to the 3' terminus of the nucleic acid encoding a factor such as a drought-tolerant factor.

Selectable and Screenable Marker Sequences:

In order to improve identification of transformants, a selectable or screenable marker gene can be employed with the factor or other polypeptide nucleic acids that are operably linked to any of the promoters described herein.

"Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for the marker by chemical means, i.e., through the use of a selective agent (e.g., a herbicide, antibiotic, or the like), or whether marker is simply a trait that one can identify through observation or testing, i.e., by 'screening' (e.g., the R-locus trait). Many examples of suitable marker genes are available and can be employed in the practice of the invention.

Included within the terms selectable or screenable marker genes are also genes which encode a secretable marker whose secretion can be detected as a means of identifying or selecting for transformed cells. Examples include markers which encode a secretable antigen that can be identified by antibody interaction, or secretable enzymes that can be detected by their catalytic activity. Secretable proteins fall into a number of classes, including small, diffusible proteins detectable, e.g., by ELISA; and proteins that are inserted or trapped in the cell wall (e.g., proteins that include a leader sequence such as that found in the expression unit of extensin or tobacco PR-S).

With regard to selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of marker proteins suitable for modification in this manner include extensin or hydroxyproline rich glycoprotein (HPRG). For example, the maize HPRG (Stiefel et al., The Plant Cell. 2:785 793 (1990)) is well characterized in terms of molecular biology, expression, and protein structure and therefore can readily be employed. However, any one of a variety of extensins and/or glycine rich wall proteins (Keller et al., EMBO J. 8:1309 1314 (1989)) could be modified by the addition of an antigenic site to create a screenable marker.

Numerous other possible selectable and/or screenable marker genes will be apparent to those of skill in the art in addition to the one set forth herein. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with expression cassettes include, but are not limited to, a neo gene (Potrykus et al., Mol. Gen. Genet. 199:183 188 (1985)) which codes for kanamycin resistance and can be selected for using kanamycin, G418, and the like; a bar gene which codes for bialaphos resistance; a gene which encodes an altered EPSP synthase protein (Hinchee et al., Bio/Technology. 6:915 922 (1988)) thus conferring glyphosate resistance; a nitrilase gene such as bxn from *Klebsiella ozaenae* which confers resistance to bromoxynil (Stalker et al., Science. 242:419 423 (1988)); a mutant acetolactate synthase gene (ALS) which confers resistance to imidazolinone, sulfonylurea or other ALS-inhibiting chemicals (European Patent Application 154,204 (1985)); a methotrexate resistant DHFR gene (Thillet et al., J. Biol. Chem. 263:12500 12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

Another selectable marker gene capable of being used in for selection of transformants is the gene that encodes the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., Mol. Gen. Genet. 205:42 50 (1986); Twell et al., Plant Physiol. 91:1270 1274 (1989)) causing rapid accumulation of ammonia and cell death. The success in using this selective system in conjunction with monocots was surprising because of the major difficulties that have been reported in transformation of cereals (Potrykus, Trends Biotech. 7:269 273 (1989)). Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: CHROMOSOME STRUCTURE AND FUNCTION: IMPACT OF NEW CONCEPTS, 18th Stadler Genetics Symposium, J. P. Gustafson and R. Appels, eds. (New York: Plenum Press) pp. 263 282 (1988)); a β-lactamase gene (Sutcliffe, Proc. Natl. Acad. Sci. USA. 75:3737 3741 (1978)), which encodes an enzyme for which various chromogenic substrates are known (e.g., PADAC, a chromogenic cephalosporin); a xylE gene (Zukowsky et al., Proc. Natl. Acad. Sci. USA. 80:1101 (1983)) which encodes a catechol dioxygenase that can convert chromogenic catechols; an α-amylase gene (Ikuta et al., Bio/technology 8:241 242 (1990)); a tyrosinase gene (Katz et al., J. Gen. Microbiol. 129:2703 2714 (1983)) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., Science. 234:856 859.1986), which allows for bioluminescence detection; or an aequorin gene (Prasher et al., Biochem. Biophys. Res. Comm. 126:1259 1268 (1985)), which may be employed in calcium sensitive bioluminescence detection, or a green or yellow fluorescent protein gene (Niedz et al., Plant Cell Reports. 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions can be employed in chimeric constructs in order to provide mechanisms for controlling the expression of chimeric genes. More diversity of phenotypic expression is known at the R locus than at any other locus (Coe et al., in Corn and Corn Improvement, eds. Sprague, G. F. & Dudley, J. W. (Am. Soc. Agron., Madison, Wis.), pp. 81 258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the constructs is firefly luciferase, encoded by the lux gene. The presence of the lux gene in transformed cells may be detected using, for example, X-ray film, scintillation counting, fluorescent spectrophotometry, low light video cameras, photon counting cameras or multiwell luminometry. It is also envisioned that this system may be developed for population screening for bioluminescence, such as on tissue culture plates, or even for whole plant screening.

Other Optional Sequences:

An expression cassette can be placed in a plasmid or vector. Plasmid vectors include additional DNA sequences that provide for selection, amplification, and transformation of the expression cassette in prokaryotic and eukaryotic cells, e.g., pUC derived vectors such as pUC8, pUC9, pUC18, pUC19, pUC23, pUC119, and pUC120, pSK derived vectors, pGEM derived vectors, pSP derived vectors, or pBS derived vectors. The additional DNA sequences include origins of replication to provide for autonomous replication of the vector, a selectable marker genes (e.g., antibiotic or herbicide resistance), unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (Methods in Enzymology. 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette described herein can be used to transform both prokaryotic and eukaryotic cells, but in some cases is used to transform dicot plant cells.

In Vitro Screening of Expression Cassettes:

Once the expression cassette is constructed and subcloned into a suitable plasmid, it can be screened for the ability to express a drought tolerance factor or the polypeptide of interest. For example, an expression cassette having one of the promoters described herein can be screened to ascertain whether it can promote expression of a drought tolerance factor or other polypeptide of interest by methods described herein or other available methods. An expression cassette having one of the promoters described herein can be screened to ascertain whether it can promote expression of a drought tolerance factor or the polypeptide of interest, for example, by immunological detection of the encoded product, by detection of the activity of the polypeptide, be detection of its function (e.g., drought tolerance), by hybridization, or PCR detection of transcripts encoding the drought tolerance factor or the polypeptide of interest, or by other procedures available to those of skill in the art.

DNA Delivery of the DNA Molecules into Host Cells:

Constructs and/or expression vectors can be introduced into host cells by a variety of methods. For example, a construct or vector encoding a selected a drought tolerance factor or polypeptide of interest can be introduced into a recipient cell to create a transformed cell by available procedures. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells can be regenerated into transgenic plants, through the application of the techniques disclosed herein.

Another aspect of the invention is an isolated plant or plant cell that has one of the promoters introduced into the cell, e.g., as a nucleic acid segment operably linked to a drought tolerance factor or other polypeptide of interest. The plant can be a monocotyledon or a dicotyledon.

Another aspect of the invention includes plant cells (e.g., embryonic cells or other cell lines) that can regenerate fertile transgenic plants and/or seeds and that include one or more of the promoters described herein (e.g., in a construct or expression vector). The cells can be derived from either monocotyledons or dicotyledons. Suitable examples of plant species include wheat, rice, oats, *Arabidopsis*, tobacco, maize, soybean, corn, grasses (e.g., *miscanthus*, switchgrass, and the like), as well as trees such as poplar, aspen, willow, and the like. In some embodiments, the plant or cell is a monocotyledon plant or cell. For example, the plant or cell can be a maize plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. No. 5,384,253 and U.S. Pat. No. 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988); Gordon Kamm et al., The Plant Cell. 2:603 618 (1990); U.S. Pat. No. 5,489,520; U.S. Pat. No. 5,538,877; and U.S. Pat. No. 5,538,880) and DNA transfer to plant cells via infection with *Agrobacterium*. Methods such as microprojectile bombardment or electroporation can be carried out with "naked" DNA where the expression cassette may be simply carried on any *E. coli* derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf disk protocol (Horsch et al., Science 227:1229 1231 (1985). Monocots such as *Zea mays* can be transformed via microprojectile bombardment of embryogenic callus tissue or immature embryos, or by electroporation following partial enzymatic degradation of the cell wall with a pectinase containing enzyme (U.S. Pat. No. 5,384,253; and U.S. Pat. No. 5,472,869). For example, embryogenic cell lines derived from immature *Zea mays* embryos can be transformed by accelerated particle treatment as described by Gordon Kamm et al. (The Plant Cell. 2:603 618 (1990)) or U.S. Pat. No. 5,489,520; U.S. Pat. No. 5,538,877 and U.S. Pat. No. 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation are carried out with "naked" DNA where the expression cassette may be simply carried on any *E. coli* derived plasmid cloning vector. In the case of viral vectors, it is desirable that the system retain replication functions, but eliminate functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the promoter and operably linked coding region nucleic acids for an effective period of time. This may range from a less than one second pulse of electricity for electroporation to a 2-3 day co cultivation in the presence of plasmid bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation:

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment:

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. For example, non-embryogenic Black Mexican Sweet maize cells can be bombarded with intact cells of the bacteria *E. coli* or *Agrobacterium tumefaciens* containing plasmids with either the β-glucuronidase or bar gene engineered for expression in maize. Bacteria can be inactivated by ethanol dehydration prior to bombardment. A low level of transient expression of the 0-glucuronidase gene may be observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. The particles may increase the level of DNA delivery but may not be, in and of themselves, necessary to introduce DNA into plant cells.

An advantage of microprojectile bombardment, in addition to it being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. For example, one method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of such techniques one may obtain up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize:

After effecting delivery of one or more of the promoters described herein operably linked to a drought tolerance factor or the polypeptide of interest to recipient cells by any of the methods discussed above, the transformed cells can be identified for further culturing and plant regeneration. As mentioned above, in order to improve the ability to identify transformants, one may employ a selectable or screenable marker gene in addition to the promoter-linked nucleic acids. In this case, one would then generally assay the potentially transformed cell population by exposing the cells to a selective agent or agents, or one would screen the cells for the desired marker gene trait.

Selection:

An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

Examples of screenable marker traits include GUS encoded by the uidA gene, or the red pigment produced under the control of the R-locus in maize. Expression of GUS or red pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production:

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soil-less plant growth mix, and hardened, e.g., in an environmentally controlled chamber at about 85% relative humidity, about 600 ppm $CO_2$, and at about 25-250 microeinsteins/sec·$m^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C.

After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the promoter-coding region nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced promoter-coding region nucleic acids, the plant is self-pollinated at least once in order to produce a homozygous backcross converted inbred containing the promoter-coding region nucleic acids. Progeny of these plants are true breeding. Alternatively, seed from transformed monocot plants regenerated from transformed tissue cultures is grown in the field and self-pollinated to generate true breeding plants.

Seed from the fertile transgenic plants can then be evaluated for the presence and/or expression of the factor expressed from any of the promoters described herein. Transgenic plant and/or seed tissue can be analyzed for product expressed from any of the promoters described herein using standard methods such as SDS polyacrylamide gel electrophoresis, liquid chromatography (e.g., HPLC) or other means of detecting such a product.

Once a transgenic plant line is identified that expresses a factor or product from any of the promoters described herein, the seed from the plant line can be used to develop true breeding plants. The true breeding plants are used to develop a line of plants that have any of the promoters described herein and/or contain a nucleic acid encoding such a promoter linked to a polypeptide of interest, while still maintaining other desirable functional agronomic traits. Adding the trait of a drought tolerance factor or polypeptide of interest expression to the plant can be accomplished by back crossing with this trait with plants that do not exhibit this trait and by studying the pattern of inheritance in segregating generations. Those plants expressing the target trait in a dominant fashion are preferably selected. Back crossing is carried out by crossing the original fertile transgenic plants with a plant from an inbred line exhibiting desirable functional agronomic characteristics while not necessarily expressing the trait of a desired polypeptide or factor that would be expressed from one of the promoters described herein in the plant. The resulting progeny are then crossed back to the parent that expresses the trait from one of the promoters described herein. The progeny from this cross will also segregate so that some of the progeny carry the trait and some do not. This back crossing is repeated until an inbred line with the desirable functional agronomic traits, and with expression of the desired trait within the plant. Such expression of the desirable factors or other products in plant can be increased under drought conditions but reduced under non-drought conditions to provide healthy, well-grown, and productive plants that survive under drought conditions when others may not.

Subsequent to back crossing, the new transgenic plants can be evaluated for expression of a drought tolerance factor or the polypeptide of interest. For example, when a plant expresses a drought tolerance factor from any of the promoters described herein the growth and survival of plants under drought stress conditions is significantly better than in plants that do not express such a factor under the control of one the promoters. Moreover, plants grow larger when expressing a drought tolerance factor from any of the promoters described herein than if that same drought tolerance factor is constitutively expressed. See, e.g., FIGS. 4-5. In addition, plants that express drought tolerance factors from any of the promoters described herein loose less water than plants that do not express such a factor under the control of one the promoters (FIG. 6-7).

The new transgenic plants can be evaluated for a battery of other agronomic characteristics such as lodging, kernel hardness, yield, resistance to disease, resistance to insect pests, drought resistance, and/or herbicide resistance. Methods for such evaluation are available to those of skill in the art.

Plants that may be improved by these methods (incorporation of expression cassettes under the control of any of the drought-inducible promoters) include but are not limited to food crops (e.g., sugar beets, beets, tomatoes, lettuce, spinach, carrots, peppers, broccoli, beans, asparagus), fiber-containing plants, trees, flax, grains (e.g., maize, wheat, barley, oats, rice, sorghum, millet, and rye), grasses (switchgrass, prairie grass, wheat grass, sudangrass, sorghum, straw-producing plants), woody plants (e.g., those used for paper production such as poplar species, pine species, and *eucalyptus*), softwood, hardwood, oil and/or starch plants (canola, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, *Radiata* pine, spruce, Douglas fir and others. Hardwoods that can be modified as described herein include aspen, poplar, *eucalyptus*, and others. Plants useful for making biofuels and ethanol include corn, grasses (e.g., *miscanthus*, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues:

To confirm the presence of the promoter, expression cassette, and associated coding regions in the regenerating plants, or seeds or progeny derived from the regenerated plant, a variety of assays may be performed. Such assays include, for example, molecular biological assays available to those of skill in the art, such as nucleic acid amplification: polymerase chain reaction; Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced via the promoter and the operably linked coding region. PCR also be used to reverse transcribe RNA into DNA, using enzymes such as reverse transcriptase, and then this DNA can be amplified through the use of conventional PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the promoter and associated nucleic acids, they may not provide sufficient information as to the integrity and the amount of factor expressed from a coding region associated with one of the present promoters. Expression may be evaluated by specifically identifying the protein products of the coding region or evaluating the phenotypic changes brought about by their expression.

Assays for the production and identification of specific proteins may make use of physical chemical, structural, functional, or other properties of the proteins. Unique physical chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the factor or other polypeptide expressed by the promoter, such as evaluation by amino acid sequencing following purification. The Examples of this application also provide assay procedures for detecting and quantifying drought tolerance factors. Other procedures available to those of skill can also be used.

The expression of a gene product can also be determined by evaluating the phenotypic results of its expression. These assays also may take many forms including but not limited to analyzing changes in the chemical composition, morphology, or physiological properties of the plant.

Drought Tolerance Factors

A variety of drought tolerance factors can be expressed by operably linking nucleic acids encoding such factors to one or more of the promoters described herein.

For example, one type of drought tolerance factor that can be expressed from any of the promoters described herein can be a RING-H2 zinc finger protein such as any of those disclosed in U.S. Pat. No. 7,977,535. The following is an example of a nucleic acid (SEQ ID NO:13) that encodes a RING-H2 zinc finger domain, which can be present in RING-H2 zinc finger drought tolerance factors.

```
  1    GAGTGTTCTG TGTGTTTGTC GAAATTCCAA GGGGATTCAG
 41    AGATCAACAA GCTCAAGTGC GGCCATTTGT TCACAAAAC
 81    ATGCTTGGAG AAATGGATAG ACTATTGGAA CATCACTTGC
121    CCATTGTGTA GGACTCCTCT T
```

The amino acid sequence of the RING-H2 zinc finger domain encoded by the above nucleic acid is shown below (SEQ ID NO:14)

```
  1    ECSVCLSKFQ GDSEINKLKC GHLFHKTCLE KWIDYWNITC
 41    PLCRTPL
```

One example, of a RING-H2 zinc finger protein that can confer drought tolerance to plants is XERICO (At2g04240). XERICO is a single-copy gene in the *Arabidopsis* genome and encodes a small protein (162 amino acids) with an N-terminal transmembrane (TM) domain, a RING-H2 zinc-finger motif located at the C-terminus, and a serine-rich domain in the middle. XERICO is expressed ubiquitously in the plant, but its transcript is accumulated more in actively growing tissues. An example of a cDNA sequence for XERICO is provided below as SEQ ID NO:15.

```
  1    AAAACCAACT CTCTCTACAC ACTTTTTCAG ATTCCATCAT
 41    CACTTGTTCT TTTCACACCC AATAAAAACT TGCATCTTTC
 81    TTCTAAATTG TTGATGATCG CTTCTCATAT TTGACCCTAG
121    AGACAACATC ATTTCTACCG ACAAAGATTT GATATCGAAT
161    CCAACAAGTG AAAGATGGGT CTATCAAGTC TTCCTGGTCC
201    ATCAGAAGGA ATGTTATGTG TGATATTAGT TAATACAGCA
241    TTATCGATCT CCATTGTCAA AGGCATTGTA AGATCATTCC
281    TTGGCATAGT AGGAATCAGT CTCTCGCCGT CTTCATCCTC
321    GCCTTCTTCG GTGACGGTAT CTTCAGAGAA TTCATCAACT
361    TCAGAGTCAT TTGATTTCCG GGTCTGCCAA CCAGAGAGTT
401    ACCTTGAGGA GTTCAGGAAC CGGACTCCGA CACTGAGGTT
441    TGAGAGCTTG TGCAGGTGCA AGAAACAGGC AGACAATGAG
481    TGTTCTGTGT GTTTGTCGAA ATTCCAAGGG GATTCAGAGA
521    TCAACAAGCT CAAGTGCGGC CATTTGTTTC ACAAAACATG
561    CTTGGAGAAA TGGATAGACT ATTGGAACAT CACTTGCCCA
601    TTGTGTAGGA CTCCTCTTGT TGTTGTGCCA GAAGACCATC
641    AGCTTTCTTC TAATGTTTGG TGACTGCTTT TCACTGTATA
681    GGTTTTTTGT TTGAGTGTGT TTGTTGTGTA CAGCTACTTT
721    TACTATGAAT TAGGTTGCAT CGCGGTTGAT TCTCGAGCAG
761    ATTTAAACCG GGGATGGGAT AATCTGATGT ACATATATAT
801    ATATACCCAT GTGTATGGAG CTCTTGTTTG AACACAGTTT
841    TCTTGAATC
```

The XERICO protein encoded by the above nucleic acid has SEQ ID NO:16, shown below.

```
  1    MGLSSLPGPS EGMLCVILVN TALSISIVKG IVRSFLGIVG
 41    ISLSPSSSSP SSVTVSSENS STSESFDFRV CQPESYLEEF
 81    RNRTPTLRFE SLCRCKKQAD NECSVCLSKF QGDSEINKLK
121    CGHLFHKTCL EKWIDYWNIT CPLCRTPLVV VPEDHQLSSN
161    VW
```

Another example of a drought tolerance factor is the SlPP2C1 gene product from *Solanum lycopersicum* that is described in U.S. Patent Application Publication No. 20120084881, which is specifically incorporated by reference in its entirety. An example of a nucleic acid encoding the SlPP2C1 gene product is provided below as SEQ ID NO:17.

```
  1    ATGATTGATA ACGTTAAAGG TATGCCGCCG GCAACCGAGA
 41    AAGGTTGCCG GTTAACGGCG TTGATAGATT CCGGTGGACT
 81    AGCAGAAGTA GATCTGAGTG AGAAGGAGCA AAATTCTACT
121    CGACGTAGGC GATTGGATGA ACGTTTGTTG AAATCGACGA
```

-continued

```
 161  CTGAGCTACC GGAAAATTTC GATGTCTTCG CAGATGATTA
 201  CAGGCATTGT AAGAGGAAAA AAAGTACTGT AACTGATACT
 241  GATGATCATC GAGTTCAACT AGCGTTATCT AGTGAAGTGA
 281  AAAAAGTAAG GGAGAGCTTG GTGACGTGCT GTTCACATGG
 321  ATCGATATCG TTGATCGGCC GGAGAAGGGA AATGGAAGAT
 361  GCGGTGGCGA TTTATCCGTG TTTTTTCAGT GAAGGCGGCG
 401  GCGGCGGCAG CAGGAGGTAT GATTATTTTG GTGTTTACGA
 441  CGGGCATGGA GGGTCACGTG TAGCGAACGT GTGCCGTGAC
 481  TTTTTGCACC GTTTAGTGAT ACAGCAAGTT TCGGAAGGAG
 521  AAGATTACGA TGGGAAGAGT ATTAACTGGG AGAAAGTTAT
 561  GACGGAGAGT TTCCGTAAAA TGGACGAAAA GGTGAACAAG
 601  GAAGGGGCGG AGATGGCGAC GATAGGATCA ACGGCGGTGG
 641  TAGCGGTGGT GGGAGTGGAG GAATTTGTTG TTGCGAATTG
 681  TGGAGATTCA AGAGCTGTGC TTTCACGTGC TGGAGTTGCC
 721  GTACCTTTGT CTATTGATCA TAAGCCTGAC AGACCTGATG
 761  AGCTGGATAG AATTGAAAAT TCAGGTGGGA AAGTCATAAA
 801  TTGGAATGGA CAAAGAGTCT TAGGAGTTCT TGCTACTTCA
 841  AGATCCATAG GTGATATGTA CCTCAAACCG TACGTGATAC
 881  CAGATCCTGA AGTGATAGTT AGCAAAAGAA GCGATGAAGA
 921  TGAGTTCTTA ATACTTGCAA GTGATGGTCT ATGGGATGTC
 961  ATTCCAAATG ATGTTGCGTG TGACGTTACA AGAAGATGCT
1001  TGAATGGTCA AACGTTCAGA AGGTGCGATC AACAAACCAA
1041  ATCCTATAAG AGAGATGAAG GCGTCAAAGA AAGTCTCGCA
1081  GCACGGGCAG CTTCCTTCCT TGCAGAGTTA GCAATTGCTC
1121  GGGGTAGTAG GGATAACATC AGCGTAATTG TCGTCAATTT
1161  GAATAGATCT GTACGTTCAT CCATTGATAG TTAA
```

The protein sequence encoded by this nucleic acid is shown below as SEQ ID NO:18.

```
  1  MIDNVKGMPP ATEKGCRLTA LIDSGGLAEV DLSEKEQNST
 41  RRRRLDERLL KSTTELPENF DVFADDYRHC KRKKSTVTDT
 81  DDHRVQLALS SEVKKVRESL VTCCSHGSIS LIGRRREMED
121  AVAIYPCFFS EGGGGGSRRY DYFGVYDGHG GSRVANVCRD
161  FLHRLVIQQV SEGEDYDGKS INWEKVMTES FRKMDEKVNK
201  EGAEMATIGS TAVVAVVGVE EFVVANCGDS RAVLSRAGVA
241  VPLSIDHKPD RPDELDRIEN SGGKVINWNG QRVLGVLATS
281  RSIGDMYLKP YVIPDPEVIV SKRSDEDEFL ILASDGLWDV
321  IPNDVACDVT RRCLNGQTFR RCDQQTKSYK RDEGVKESLA
361  ARAASFLAEL AIARGSRDNI SVIVVNLNRS VRSSIDS
```

The promoters described herein can also be operably linked to nucleic acid segments encoding SlPP2C1-related gene products. Such SlPP2C1-related gene products can also be drought tolerance factors. SlPP2C1-related gene products include those with the following sequence accession numbers: AT5G51760, AT3G11410, AT5G59220, AT1G07430, AT2G29380, AT1G17550, AT1G72770, AT4G26080, and/or AT5G57050.

A drought tolerance factor or a nucleic acid segment encoding such a drought tolerance factor can have at least 50% sequence identity to any of SEQ ID NO:13, 14, 15, 16, 17, and/or 18. A drought tolerance factor or a nucleic acid segment encoding such a drought tolerance factor can also have at least 55%, or at least 60%, or at least 65%, or at least 70%, or at least 75%, or at least 80%, or at least 85%, or at least 90%, or at least 95%, or at least 96%, or at least 97%, or at least 98% sequence identity to any of the group of SEQ ID NO:13, 14, 15, 16, 17, and/or 18. In some instances, the drought tolerance factor or a nucleic acid segment encoding such a drought tolerance factor has less than 100% sequence identity to any of SEQ ID NO:13, 14, 15, 16, 17, and/or 18. For example, the drought tolerance factor or a nucleic acid segment encoding such a drought tolerance factor can have less than 99.9%, or less than 99.5%, or less than 99% sequence identity to any of SEQ ID NO:13, 14, 15, 16, 17, and/of 18.

Related nucleic acid segments encoding drought tolerance factors can be isolated from selected plant species or generated by procedures available to those of skill in the art, and operably linked to one or more of the promoters described herein.

Definitions

As used herein, the terms "crop" and "crop plant" are used herein its broadest sense. The term includes, but is not limited to, any species of plant or algae edible by humans or used as a feed for animals or fish or marine animals, or consumed by humans, or used by humans, or viewed by humans (flowers) or any plant or algae used in industry or commerce or education, such as vegetable crop plants, fruit crop plants, fodder crop plants, fiber crop plants, and turf grass plants.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "expression" when used in reference to a nucleic acid sequence, such as a coding region or protein, refers to the process of converting genetic information encoded in a coding region into RNA (e.g., mRNA, rRNA, tRNA, or snRNA) through "transcription" of a coding region or a portion of an expression cassette (i.e., via the enzymatic action of an RNA polymerase), and into protein where applicable (as when a coding region encodes a protein), through "translation" of mRNA. Gene expression can be regulated at many stages in the process. "Up-regulation" or "activation" or "increased expression" refers to regulation that increases the production of gene expression products (i.e., RNA or protein), while "down-regulation" or "repression" or "decreased expression" refers to regulation that decreases production. Molecules (e.g., transcription factors) that are involved in up-regulation or down-regulation can also be called "activators" and "repressors," respectively. Expression can also be inducible by environmental conditions or factors introduced into the environment.

As used herein, the term "heterologous" when used in reference to a gene, promoter, or nucleic acid refers to a gene, promoter, or nucleic acid that has been manipulated in some way. For example, a heterologous nucleic acid, heterologous coding region, or a heterologous promoter includes a nucleic acid, coding region, or promoter that is not normally in the species to which it has been introduced or that is not normally linked to the nucleic acids to which it is linked. A heterologous nucleic acid or promoter therefore includes a nucleic acid or promoter that is native to one type of organism but that has been altered in some way (e.g., placed in a different chromosomal location, mutated, added in multiple copies, linked to a non-native coding region or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous coding regions can be distinguished from endogenous plant coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, the terms "leaf" and "leaves" refer to a usually flat, green structure of a plant where photosynthesis and transpiration take place and attached to a stem or branch.

As used herein, a "native" nucleic acid or polypeptide means a DNA, RNA or amino acid sequence or segment that has not been manipulated in vitro, i.e., has not been isolated, purified, and/or amplified.

As used herein, the term "naturally linked" or "naturally located" when used in reference to the relative positions of nucleic acid sequences means that the nucleic acid sequences exist in nature in those positions.

As used herein, the terms "operably linked" or "in operable combination" or "in operable order" refers to the linkage of nucleic acids in such a manner that a nucleic acid molecule capable of directing the transcription of a given coding region and/or the synthesis of a desired protein molecule is produced. As used herein, the term also refers to the linkage of amino acid sequences in such a manner so that a functional protein is produced.

As used herein, the term "plant" is used in its broadest sense. It includes, but is not limited to, any crop species, any species of grass (e.g. turf grass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, stomata, a seed, a tiller, a sprig, a stolon, a plug, a rhizome, a shoot, a stem, a leaf, a flower petal, a fruit, etc.

As used herein, the terms "protein," "polypeptide," "peptide," "encoded product," "amino acid sequence," and "factor" are used interchangeably to refer to compounds comprising amino acids joined via peptide bonds and. A "protein" encoded by a gene is not limited to a segment with the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence can include post-translational modifications of the encoded and deduced amino acid sequence.

As used herein, "seed" refers to a ripened ovule, consisting of the embryo and a casing.

As used herein, "stem" refers to a main ascending axis of a plant.

As used herein, the term "transfection" or "transformation" refers to the introduction of foreign DNA into cells. Transfection or transformation may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment), *Agrobacterium* infection, and the like. Methods of transfection and transformation are described herein, and are available to those of skill in the art.

As used herein, the term "transgene" refers to a foreign gene (e.g., an expression cassette) that is placed into an organism by the process of transfection.

As used herein, the term "vector" refers to nucleic acid molecules that transfer DNA segment(s). Transfer can be into a cell, cell-to-cell, etc.

As used herein, the term "wild-type" when made in reference to a nucleic acid or gene refers to a functional nucleic acid or gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples illustrate aspects of the invention.

Examples: Promoters Inducible by Drought Conditions

This Example describes methods for identifying drought-inducible promoters and the promoters so identified.

A series of promoters were tested for drought-inducible expression by fusion of test promoter sequences with the uidA gene, which expresses the GUS polypeptide that produces a blue color when exposed to 5-bromo-4-chloro-3-indolyl glucuronide (X-Gluc).

Promoter segments were fused with uidA gene by appropriate restriction enzymes at the underlined MCS (multi-cloning site) in the pCB308 backbone as illustrated by FIGS.

2 and 3. The plant transforming binary vector, pCB308, is derived from the pCB301 vector described by Xiang et al. (Plant Mol Biol 40: 711-717 (1999)). The numbers under each DNA region in the constructs shown in FIGS. 2 and 3 indicate the approximate size of the region in base pairs; arrows indicate the orientation of transcription. The following components were present in the pCB308 vector: promoter segments from a Gene of Interest (GOI) identified in the chart below; gene for phosphinothricin acetyltransferase (bar); left border of the T-DNA (LB); multiple cloning site (MCS, from pBluescript II); gene for neomycin phosphotransferase (nptIII) for kanamycin resistance (from pBIN19); part of RK2 origin of replication (oriV, from pBIN19); promoter of nopaline synthase gene (Pnos); right border of the T-DNA (RB); terminator of nopaline synthase gene (Tnos); part of the RK2 origin of replication (trfA); gene for P-glucuronidase (uidA, encoding GUS).

Figure 1:
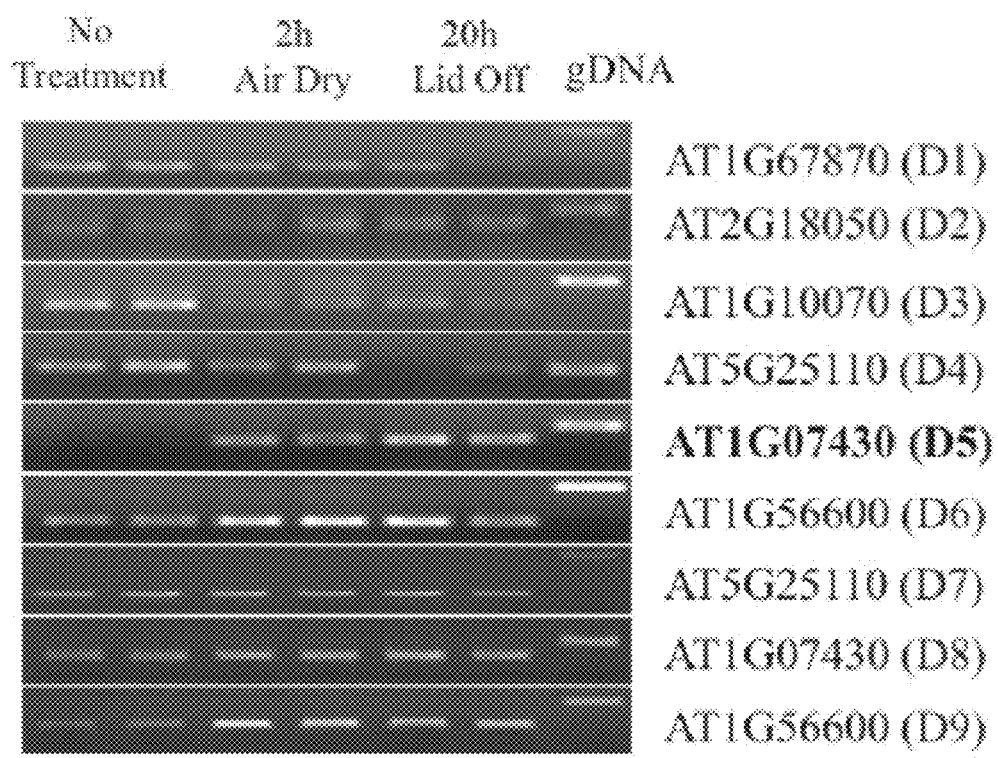
FIG. 1 illustrates drought-inducible expression of gene of interesting (GOI) functions in Arabidopsis plants by drought-inducible promoters. Drought stress was induced by keeping the plants on dry Petri dishes for 2 hours or/and 20 hours with the lid off in a Laminar flow hood before the RT-PCR analysis. The D5 lines showed the highest expression pattern. (SEQ ID NO:19)

Arabidopsis col-0 wild type was subjected to drought treatment by exposing the plants to 2 hours of dry air and 20 hours with the lids off of the culture plate. The following nine genes exhibited drought-inducible expression, with the selected promoter segment identified. D5 (AT1G07430) exhibited the strongest drought-inducible expression compared with normal condition (FIG. 1).

TABLE 1

Sources of Promoters

| Promoter Source | Gene Name | Ref | Promoter size (bp) | Restriction Enzyme |
|---|---|---|---|---|
| AT1G67870 | unknown | D1 | 1072 | XbaI/BamHI |
| AT2G18050 | His1-3: putative histone | D2 | 1085 | XbaI/BamHI |
| AT1G10070 | ATBCAT-2 (branched-chain amino acid metabolism) | D3 | 979 | SacI/BamHI |
| AT5G25110 | CBL-Interacting Protein kinase 25 | D4 | 1067 | SpeI/BamHI |
| AT1G07430 | AKT1 Interacting Protein Phosphatase 1 | D5 | 1056 | SacI/BamHI |
| AT1G56600 | GolS2 (galactinol synthase) | D6 | 1057 | SpeI/BamHI |
| AT5G18130 | unknown | D7 | 1055 | XbaI/BamHI |
| AT2G25625 | unknown | D8 | 1023 | XbaI/BamHI |
| AT2G46680 | Homeobox 7 | D9 | 1176 | SpeI/BamHI |

Sequences of these promoter segments are provided herein as SEQ ID NOs: 1-12, and shown below.

The D1 promoter associated with the *Arabidopsis thaliana* AT1g67870 gene has the following sequence (SEQ ID NO:1).

```
TGTTGGGGCAAAATTGATATGTAAGTTCGTCTATGGGAGGGAATTAAGTT
TCCGCTGAGTAATAAACAAACAAGTGCAAACCTAGGAATTCAACACCAAT
GTAATTTTTTATAATTTTGTAGGACTCTTTAATAGTCAAGTCAGTATTTA
AACCACAAGAGTCGGTCAGAAACCAGAAAAACTAGAAACAAGTTATGTCA
GTTCTAAGAAGAGAGATGTGCAATGTATTCGGCAATCGGTATATCATCT
AACATTTTAGCCAGTGAAAAAAGAGAAAGATATGAGGATTTTTCCATTGT
TCAGTAAGCTAAGAGAAGACAGTTTCATTAAAGAGTCGAATAGAATGGAT
ATTCTCATGAAACTGAGAAGGTTAAGTTTTTTGGGGAATACTTTGCATG
CCTTTATATAGGTGAAGAGTCATGTTGCATAGCTCCGAGGCATTTCAGCT
TATAAGTATCCATGTCTCGACTCATATGATGAATGGACTTGATGAAGGGA
CTAGGCAATCGATCGTCAGTGCGGGTGAATTTTGACGTCTTGAGTCCATC
CGACCATTCAAAAGAAAGTATTCTTCTTACCACGTAGCATGTGACTTTAC
CTAGAGTTCGTGGAGCACAAGTAGAACAAATAGGATTATGCCTAAACACC
TTTAGAACTAGACCAAAGGTCAAAAACTATCAAAACAAGTTTTTTACGCT
ACATGGTTTACATAAAAAAATTAAGTGATACACTCAATGATGAATAACAA
TATTAACCCAAACAAATTTGATATCAAAACACAGTATAACCAAAATCAAA
ACCGTAGTGGAACTAAACTAGATTATATAATATGCCTCCATAAATACTCG
GATTTTCCACGTGAATTGGACTAATCATTAATTAGGAAGAACGGAATCAG
AATAAATATGTCTACTCAACTTTCGGTATGGTGGTGGTAGAAAAGAGAAT
AAGATTCAAAGCATATTACGAATTATTGCCATATGGGATCATATCTAACA
CAAATTTAAAAGAACACTCTACTACTACAGTACAAAATTGTATATATATA
AACACCTGAAAGATTTTAATTA
```

The D2 promoter associated with the *Arabidopsis thaliana* At2g18050 gene has the following sequence (SEQ ID NO:2).

```
caccttgaaacattaactccgtaattaatttagtcttgcaattttcata
aattgtttatatatgtcgtaacacaaaatttgcgaacggttaataacttt
actagataaaacctctctaaataggtagatgtgaaaaataaataaatttt
tgttttaataaattttcaaatgataatctatatatattttatttaatat
atattttctaaaaccaaatttcaatcttacctttctaaaaccatattgt
taaaaactaaagaaaaagttggaccaagcaaagcctctcggtaaatgtgg
taaataaatagaacgatataactgagaagaagaaaataaaacaaaattaa
gaaaataaaaagataaacatatttaagttacaatatttaaaaatattaaa
acacttcttttaagaacaaaatggggaattttatttatgttttgaatag
atcaacaattattaatagaatgagtttagtttaatatattaaatataaaa
aattgaatatataaacaattgtttatgtatatatttttttttttgatagg
gttaaggattttttttctattttttgttttaaatgtaataaaatttgaaac
acatgtaaatatcgtattagtaaataccgaccaaaaaaaatattgtatta
gtaaatttgacacatatcgcaattttgtgagctaacaattttaaaaatc
aaataagatgacgaacaaagctctggttaaactttctcccatcaatttt
ttcattaaaccaaatttaaccaattatttggcctaataactgcgtctacg
ttattaagaataagaacttattttgtgtttcagtagaaaacacactcgtt
cacaaaatgcctagtaagagtaaaggacgatcaccgccaccaagtgtgtt
tctcggataaacacatggaatccagccattacttaaacgacacgtgtacg
ctcatgatttattaatgcacacgtaatcgatcctctgacaaaaaccataa
cgaatacagaaaacacacgaatacacttccctgcgctataaatagctag
cacgaaaaaatttaacagatagagacaagacaagc
```

The D3 promoter associated with the *Arabidopsis thaliana* At1g10070 gene has the following sequence (SEQ ID NO:3).

```
attctatttgccagactctacggcggtatattcgcttttagaaaaaaaac
aattttgtcgaaacttttttttttttgtaaatattgtagattccacacac
aagactgtctaagattctttgataagacacgacaaatgcgatttaagatt
tttcaaagaaatgaggttcgttgattgttccactaggtttggtatattta
taatttgaatttttttttttaaagatatttataagaaaacgaaggagtgt
gctcgcgtcaagtgtgtactaatagtcgatgacactagtgatacgacgat
actggaaagggacatcaatattcattagtaagccatcttagcaaaaacgt
tgttatcagataagaaaagttctcagactgacgtggctgtcaatctccac
aacgtgtttatctcccatttgggtagttacggacaaagacgttgaaaaga
caacaatatggtctaaaagattgacatggaaagaaaattgtttatccgac
aaagacctcttggtccaacgtggctttcacatcactagtttactatttca
catctcatggaaaattactgaaattagtacttgtctgtattttgttttt
cgtcaagtatttgtttgtatactttaggtaattgcgtgccgaagaaacat
tgctaaattgatatttataccaacttacaatagtttacagttcaaaaata
gaaatctccattttgaagatacaccactaattttcttcatttatttaccc
cataagagaacgagaaaagaacaatagtccgttgatttcgttaaaatcta
gtttcagaaagacacgtctagatctgtctgatcagggcagatagacacaa
gtgacgaagcaaaagaaacacaaaaataagataagaactcttaccactaa
aagataaaaataagaaaaaaataaaacaaattcaacgatttgccaagat
aaaagcagacactgtacataagctccgca
```

The D4 promoter associated with the *Arabidopsis thaliana* At5g25110 gene has the following sequence (SEQ ID NO:4).

```
gttgtttatattgttactaggcctttgtataaataccaaatactttgatt
atttttttactgatttcatgtcaaacaaaattccaaacaacttaaaggaa
aaagcttactcgattggaataaaaattgtacgtttaacaaaatgatatta
gtgaaataaataaaccagctcaacatttaaggatttctacgtgtatatac
agtaatcgtgtttagtattaattagctatagtttagcctcaaaaaacaaa
gatccaaaacaacatgacgaaattgacttccacatcgtgtcctttctcgt
cgacataaaaactttaatatatagatgcatgtataagtatactcactatt
tgtgtcattagtattttctttttgatacttggagctaatgacaaaaatt
ccgctagaaatatcttctccaacgatagctacaaacaaatactaccattg
cgtcatcatcacttatttatattcgatatttcagtcaacaacactaatct
ctttcaccaaaatctttggactattattacaaatgaattaaaaacttgga
cccttaataacatatttgtttcattaaatctatacaactcttattaaaaa
tgatattttcttaaatcaaaaattaatcaaaattaaggtaggctctagag
gattgcatcatttgcccacccacattagcctgccattattattggacggt
aacaaatttccttacaccaatgaaatggtaagttacaattattattaacat
ttctatataaaatagtttggttattacattaattttttatttaatactat
aaacttaaaaattcaatgctgaaaagtgtaacggaaagagggacattaaa
tatatgttaatataataagtatatttactatttaaaaaagacttatgtaa
atacatattgtatagagagaaaaataacccatagtataaaaacttgcatc
tctaaaaccgcagcattgataataagagtctctttcttcttaagtatctc
ttaattaacccacataatatatttacaagtggccgcctcatacatcccct
ctcaagtcctttgcttc
```

The D5 promoter associated with the *Arabidopsis thaliana* AT1G07430 gene has the following sequence (SEQ ID NO:5).

```
atcttaacttctgcaacgaatcaatgtattaatttataggagatccggat
aaaattatggatatatgcacgctacttctttcatttttaattaggtaaat
ggttataactttattttatatatcaattaaatgattttggtatgagatta
ctagtacactttctttgcaaatgttttaaacacgacaagacaaaaatatt
acaagcatattttggtaaaaaatatcataagctttcatatcaaaatcatt
agttatgatgttagattttttttttttttttaacactacaaaaagctc
tggtcttaatatgttagaaatttagtccaaaccagcctacagaggattt
agctaaacaattcccaagcaccttttaagtgttaaccgaaataacgtaat
atgatgttaaaggttacataaaaacaaaactaaagaattttcatatgaaa
agttaacgtacgtgtcttagtgtaacctaattttagttcacagtatataa
attctttaatgagatgatcgcaaaatcgctgtatacaatttcgtacttaa
ttcgttagtcttgaaaagttgacctaatttagatcaaattaaggttaact
acaataaaaatttaactaacgtaatgggattctttaaaattaaaaatcg
ttgattagatagatattttatctttaagggagacacagagacaatttgga
caaaaaaggtcttcctgagaaagaagtggaccacaatcgtggcgcgaaag
gaacttcctcctccctctgttgccttgtcattgggccacgtatatctcc
acctgatcgtgatgcttacgtggtccatttctagatactatagtgaccag
atcaacggtcaagattgattctaatttagacgaaagaccaacacgtcacg
tcgctagagtaaaagattttttgaaggcggagggagaaaaatcaaaagtt
aaaagtaatttgaaaacgaggaagagaaaaaggaattttaaaatgtttaa
tgaagcggtaggccgcatgggtatataaatgggcacgctttgtaacgtgt
aacgat
```

The D6 promoter associated with the *Arabidopsis thaliana* AT1G56600 gene has the following sequence (SEQ ID NO:6).

```
ggtgaattaaaggtagtgaacgccacttgcggatgcatggtacatcgcgg
caaattttataaaaatgtagaatggggacttttcatttatttaataaat
aatccatttatttggctttaagaaacctatcaattaccaaaaaaagaaga
aaactagaagaaaaaaaataaaactcgagatgtgagtaatttcatagac
ttgattggtttccgaaaaatttaaaagtataattgataaaatgttagatt
aaaagtaatttaatagctataaaaaatacaaattgagaggaactacaca
cattttttttttttatggaacctaacacaaattttttttttgttgaat
gcagataagtaatacctacttgacagaaacaaactaaaataaaataaaaa
taaaaataacgaaacataaccttatgagttttgagtcatgcaattaaaa
```

-continued

```
aatatatatgattttaacgtccacatatgccgtaaatagtcggtcggtca
tcggtcagacaaactaccataggaaagaaatttaaacatggaaatagac
caaacgggaaatgggcccaacaagacttttccttgtccacgtgtatcatc
accgcctactacgttccacgtagacacgtgtccacataataaccaatcag
aaaatcccacactaatatagtgtattaaatacccccatacgacgtcgtata
tctgaagtggaacccattgataaacacataaaaatgaccgatcaaccacc
acgagctcgatttaaaaaccttgatgagtcgaacagtctagatactgaca
cgtgtcgttatgtaacgccgtggcagcacctggattatactgggacccac
tgtaaatagttaattcaaaacgaagcttcgcgcgcgtatcctaaaccgtt
agattccaccatattgttgaatagccgttggatcaaaatctttctctgga
aacgtttagtagtcggtcgtatttaattatccaaagtaattagcgattaa
tcttttaattaattaagacaaaatcttatataaagcaccattaagcatca
cccacat
```

The D7 promoter associated with the *Arabidopsis thaliana* AT5G18130 gene has the following sequence (SEQ ID NO:7).

```
taatctaaaagctaccaaataacctaatattagtgttttttgaataattgc
ctttgtattttacaagtattgatttagttgattttcgacgaaaagctttc
ctcaaatttttttaatattatcacctatattctcattacgtaaaggatcat
atcaaggatgataagaaattataataagaaaaataaatgattctaggtgt
ttattaaatgactccctctttctacacttgttaaatgaaaacgtagttgc
tttttcctggaataacactaataattccgagcaagcaacctccactacta
ctatcttttatcattttttatccctagaaagggactttaaacttgtaactt
gtataacacatcacatcatcttctttttttcttcctttcgttttgtggtt
aatttggtaatttactttcgatgcaataaacaagccgaaaatatgaaaaa
cgttcatctgttaattagtaccaagtttatacttgaagcttgaatatagt
tatctacaccaataattttgtattattttacaagaaatttaaataccccg
cttaggtagacgtcttaatccataacttatagaaacttaaaaaacttggt
acgaaagattcttcttaatcatcagctaactaaatcttgtttttatcact
aaatattttattagcaatcaaatattgtggaaatgaattagcgtgttaa
ccaatgggtttggttataggaaatataaaatatcaaggagagaagggac
cttgtcaaagaagacaatcgatacttcttaacgtgggtcctaaaatggca
acatcttttttttgtcatttcatgtgtgtagataagctctaattcttac
ctcaccaatggttatatgaatataaaaatgatttctgtaaacaattctgt
tgaaattatgtaattatcattatatattaaatcactaatcaacactttat
acttttaacagtgacaacactaaatgcgtccatttaagagtttcgcttt
tccgtctcttcttcttctttgatcatctatttaaggatctagagaaacca
cttcg
```

The D8 promoter associated with the *Arabidopsis thaliana* AT2G25625 gene has the following sequence (SEQ ID NO:8).

```
atgagaagtaaacatagtattttgaaaaatagcaagaaaggaaatctgaa
attttagactaatagcaaaaagattttgagttaagttgacaaaattgaat
tttagtaacttgggaccttttttacatctttttttatataaaaaagtcga
cacatgagatattacttataaaattaaaaatacattattttcatgaatat
ttaatagagtttatgaatttctcacatatgttaattattaagtgctgaaa
aatgtttaattgttttctgtataaatgttaagtactgaaaaatgcttgg
aatgttttctatatttatatctctgctatttatatgtgtgatttagtgt
tatttagggcattaaatataagtattaaaatattaaattttctataat
ttaaaaataagtaaataaacatgttgtagaccgtaattgccagattattt
gtgctgtttcctaaatacttttacattctttgatggtcaccaaattaact
ataagaaaaattaggactcagtctcattaattttcggaagagaaaaaga
atcagtctcatggtagttgttaggaaatatttgaatattgtttcgccatt
agaaactttttatgtggattttttttcctgaaaacgatggttactattaat
taaacggaccgacaagaaccttgttgacgtggtaacaagtgatgacacat
gctaattggccatcattgtcaaataatttgttcgcaaggcgtgatacgtg
tacgttgttattcagacgtagcaaacagattcacgacttttgttcaattt
gtctttgtatggagtatggacctaacatctccaacggaccaatgctattg
ggtcaagtccatcttttctaggttaagttcattctttgggctttagttaa
gtatagagaaagaacatattggaagaaaaatttagatgtggtttgtattg
catgcgcatatgaaatgtaataatttgaggatacatatatagtaagaaaa
aatgagtgacccaagtaagaatg
```

The D9 promoter associated with the *Arabidopsis thaliana* AT2G46680 gene has the following sequence (SEQ ID NO:9).

```
ctattatatgccatttctatttagttttttttctaaaaatatatataaa
tatggtgttgttaacataaaaacagaaaaaaagaaaaatttagaaaattt
tctcaagaatcattatatctgtgatttatcatataagttcaaatatgata
ttagaaacaaatagtttacgagtataatagtattgtcaattttttcaatct
gaagtaaatatctttttgtaaggaaggggtcaacaaatgatcacaacaga
gttggcaaaaagttatcaaatcgcatgcacggaagttttacgtgtggtga
aggtaaacttgtattacacttatctataaaattagtttaggctttgatt
ctaaatcaaatctccgattagaaaaaattgcgtaagcaaatagctggaaa
aaattgtatcccatcatacttaagtcacaatgttttgttttgagatttg
tgatgtaatcaatatatgttttacaatgcaagtataataatattaaagtc
acattctaagaaaattatgatttgtgtcatacgtatacaaaaacacccgt
cacacatcctgacttctgaacgttaaatctgtcgcacacaatcataaaaa
tttaaaaattcaccagagatgtactgaaaagaatataattaatcacatga
tgatatatgcataggagatgaggattattcattttctgaaattccctata
tgaaccattataattgtttagtaatcagttcagaaatgctaatcattata
tgaaccattataattcccttcattttattaagatccacttaacaggat
ttgttaatatgcacccacatcactaaatacattggtacgcaaccgttgtt
```

-continued
ccatttccattttcacatcgaccagaatgtttactatgcggtaaattgtg tagtatgcagatttttttgtatcatttaattttctaacacttgttaagtc gaaactaattttgtcacaagtaaaagaaataaaaaaggtggaaattatta atcagtagttagatgattagtttcgagttgaaatgaaactcgacttaaca agtgatagcgacgactctagaaacagccaaaatccgccctattgctacct gtcgacccacaaatcgtttactcaaaaatgaataaaaaatttacgataaa gcaaacccaaagttatatcttattat The RD29A promoter (responsive to desiccation 29A) associated with the *Arabidopsis thaliana* AT5G52310 has the following sequence (SEQ ID NO:10).

GAGGAGAGAGGAGGTAAACATTTTCTTCTATTTTTTCATATTTTCAGGAT

AAATTATTGTAAAAGTTTACAAGATTTCCATTTGACTAGTGTAAATGAGG

AATATTCTCTAGTAAGATCATTATTTCATCTACTTCTTTTATCTTCTACC

AGTAGAGGAATAAACAATATTCAGCTCCTTTGTAAATACAAATTAATTTT

CGTTCTTGACATCATTCAATTTTAATTTTACGTATAAAATAAAAGATCAT

ACCTATTAGAACGATTAAGGAGAAATACAATTCGAATGAGAAGGATGTGC

CGTTTGTTATAATAAACAGCCACACGACGTAAACGTAAAATGACCACATG

ATGGGCCAATAGACATGGACCGACTACTAATAATAGTAAGTTACATTTTA

GGATGGAATAAATATCATACCGACATCAGTTTGAAAGAAAAGGGAAAAAA

AGAAAAAATAAATAAAAGATATACTACCGACATGAGTTCCAAAAAGCAAA

AAAAAAGATCAAGCCGACACAGACACGCGTAGAGAGCAAAATGACTTTGA

CGTCACACCACGAAAACAGACGCTTCATACGTGTCCCTTTATCTCTCTCA

GTCTCTCTATAAACTTAGTGAGACCCTCCTCTGTTTTACTCACAAATATG

CAAACTAGAAAACAATCATCAGGAATAAAGGGTTTG

The 7D2A promoter is a synthetic promoter that was generated by inserting two abiotic cis regulatory elements into the native XERICO promoter. The two abiotic cis regulatory elements are the DRE (drought response element, TACCGACAT) and ABRE (ABA response element, ACACGTGT) with the structure shown in FIG. 2B. The 7D2A promoter has the following sequence (SEQ ID NO:11), where the two underlined sequences (ACTAGT) are SpeI restriction enzyme sites flanking the DRE and ABRE drought response elements.

CCTGAAGCCAACCATATGCTAAGAATATTTACATAAAATACCTTAAATCG

AATATAATCTATATGGGTAATTATATCCAAAAATATCACGAAATATTATT

TCGTTGATGATAGACTTTAAAAATTGCATATTATGTACAGAAATACAATT

ACCGAACAGGAATAATTTTTTGATTACATTGACCACATAATATAACAAAA

CACTAATATTGTTTTGATAAATATTTGATGTTTTAGGAACAAAATACATG

ATGTTTTCAACTTTCAATATAAAATTAATTAATATACTTTTTTGGGTTTA

GAGGTTTCTATTCTGTAAATTGTATTTTTTTTCCTGTAGATTGTATTAC

TATTGGTCGATTAAATGGATAATAAATTAATTTTAGTTTGGAAATAAAAA

CAAATAAATGAATCCTTAAACATCAACTATAAAAAGACAGAGGAGTATCT

TTAAAGAAACTTGGATTGTGATATTGCACTGTAAATAGAACATAAAATGT

TGCAGTGTAACTTTATTTTAATCAAATAAACAAATGTTAGTAAAAAAAAA

TATATATGTTGCAAACAAGGATTAAATTC<u>ACTAG</u>TACCGACATACTAATA

CCGACATCAGTTTACCGACATGAGTTTACCGACATAGACATACCGACATA

CTAATACCGACATCAGTTTACCGACATAGACAACACGTGTCCCTTACACG

TGT<u>ACTAGT</u>AAATTCTCATTAACAAACAAACAAAAACAAAAACAAAAACA

AAGATAGTGCCAAGCATTACATATATAAACAATAAAAAGACCCTACTTAT

TAATATCTTTCCTTAAAGAAACATGGATTATTATCATTTTGGCAGTGTAT

GAAGTAATAAATATAAACAAAATGAAATAAGAAAATGCAAGCAAGTACAA

TTGATGATATAAAGTAACCATGGTTAATCAAAAAAACCTGAAAGACTGAA

ATAGAGTTAACCATAGTTAAGCTTCTCTGGTTAAAAGATAATTGCTTTGC

TATATATTAAACAACAATTGGAACCTCCTCTTTTATCAAAACCAACTCTC

TCTACACACTT

The XERICO promoter has the following sequence (SEQ ID NO:12), with the SpeI restriction site indicated by underlining.

CCTGAAGCCAACCATATGCTAAGAATATTTACATAAAATACCTTAAATCG

AATATAATCTATATGGGTAATTATATCCAAAAATATCACGAAATATTATT

TCGTTGATGATAGACTTTAAAAATTGCATATTATGTACAGAAATACAATT

ACCGAACAGGAATAATTTTTTGATTACATTGACCACATAATATAACAAAA

CACTAATATTGTTTTGATAAATATTTGATGTTTTAGGAACAAAATACATG

ATGTTTTCAACTTTCAATATAAAATTAATTAATATACTTTTTTGGGTTTA

GAGGTTTCTATTCTGTAAATTGTATTTTTTTTCCTGTAGATTGTATTAC

TATTGGTCGATTAAATGGATAATAAATTAATTTTAGTTTGGAAATAAAAA

CAAATAAATGAATCCTTAAACATCAACTATAAAAAGACAGAGGAGTATCT

TTAAAGAAACTTGGATTGTGATATTGCACTGTAAATAGAACATAAAATGT

TGCAGTGTAACTTTATTTTAATCAAATAAACAAATGTTAGTAAAAAAAAA

TATATATGTTGCAAACAAGGATTAAATTC<u>ACTAG</u>TAAATTCTCATTAACA

AACAAACAAAACAAAACAAAAACAAAGATAGTGCCAAGCATTACATAT

ATAAACAATAAAAAGACCCTACTTATTAATATCTTTCCTTAAAGAAACAT

GGATTATTATCATTTTGGCAGTGTATGAAGTAATAAATATAAACAAATG

AAATAAGAAAATGCAAGCAAGTACAATTGATGATATAAAGTAACCATGGT

TAATCAAAAAAACCTGAAAGACTGAAATAGAGTTAACCATAGTTAAGCTT

CTCTGGTTAAAAGATAATTGCTTTGCTATATATTAAACAACAATTGGAAC

CTCCTCTTTTATCAAAACCAACTCTCTCTACACACTT

Schematic diagrams of several of these promoters operably linked to the uidA coding region are shown in FIG. 2B.

The GUS coding region was replaced with a XERICO coding region. Characteristics of the promoters or ABA treatment under drought conditions are summarized in Table 2 below, where "Up" indicates that expression from the indicated promoter was increased.

TABLE 2

Characteristics of Promoter Transformants

| Promoter Source | Ref | GeneChip array data | | | |
| --- | --- | --- | --- | --- | --- |
| | | mDr day 1 | mDr day 10 | pDr | ABA* |
| AT1G67870 | D1 | | | Up | |
| AT2G18050 | D2 | Up | Up | Up | Up |
| AT1G10070 | D3 | Up | Up | Up | Up |
| AT5G25110 | D4 | Up | Up | Up | Up |
| AT1G07430 | D5 | Up | Up | Up | Up |
| AT1G56600 | D6 | Up | Up | Up | Up |
| AT5G18130 | D7 | Up | Up | Up | Up |
| AT2G25625 | D8 | Up | Up | Up | Up |
| AT2G46680 | D9 | Up | Up | Up | Up |

*Arabidopsis transformants were subjected to moderate (mDr) drought treatment by controlling the soil moisture level at a level that was nonlethal but above the wilting point, at 30% field capacity, and by replenishing the evaporated/transpired water for 1-10 days. Some plants were also subjected to progressive drought (pDr) treatment where water was withheld for a certain period of time until symptoms of wilting are observed. Some plants were treated with the phytohormone abscisic acid (ABA). See, e.g., Harb et al., Plant Physiol. 154: 1254-1271 (2010), specifically incorporated by reference herein in its entirety, which provides information about drought stress conditions and responses thereto.

FIG. 3C illustrates GUS expression from the XERICO, D5, 7D2A, and RD29A drought-inducible promoters in 8 day old T3 transgenic seedlings subjected to drought stress by keeping the lid off the petri dish for 20 hours on a clean bench before detection of GUS analysis by histochemical staining. As illustrated in FIG. 3C, GUS expression is strongly induced under drought stress conditions in plants where GUS is expressed from the RD29A and 7D2A promoters; plants with GUS expressed from the D5 and XERICO promoters also exhibit drought inducible expression.

FIG. 4A illustrates drought tolerance of transgenic plants, where expression of XERICO is driven by the RD29A, 7D2A, and D5 drought-inducible promoters. Transgenic plants with the CaMV 35S promoter-XERICO construct were used as a positive control. Drought stress treatment was achieved by growing the seedlings on media supplemented with polyethylene glycol (PEG) at −0.7 and −1.2 Mpa (see, Verslues et al., Plant J. 45(4): 523-39 (2006) for information on PEG-related drought conditions). As shown, plants expressing XERICO driven by the RD29A, 7D2A and D5 drought-inducible promoters grew normally and exhibited tolerance to PEG at −0.7 and −1.2 Mpa.

FIG. 4B illustrates growth of 21-day old wild-type and transgenic Arabidopsis plants grown under no-drought stress conditions. As shown in FIG. 4B, constitutive overexpression of XERICO from the CaMV 35S promoter resulted smaller growth, but plants expressing XERICO driven by the RD29A, 7D2A, and D5 drought-inducible promoters grew normally.

FIG. 5 illustrates drought tolerance of wild type plants (Col-0) compared to transgenic plants expressing XERICO driven by the RD29A, 7D2A, and D5 drought-inducible promoters. Growth of transgenic plants with the CaMV 35S promoter-XERICO construct is also shown. Three-week old seedlings were watered (control, Top panels of FIG. 5), and then water was withheld for two weeks (middle panels of FIG. 5). After this 2 week period of withholding water, the plants were watered (bottom panels of FIG. 5 show the plants 2 weeks after re-watering). As shown, plants with XERICO expression driven by the RD29A, 7D2A, and D5 drought-inducible promoters became green after re-watering, but the control plants without such expression (Col-0) did not.

FIG. 6 shows images of stomata that open and close under normal (no drought stress) conditions. Stomata were closed in transgenic Arabidopsis plants with constitutive overexpression of XERICO (3SS::XERICO; arrows), while those of wild-type control (Col-0) or the transgenic plants with the three drought-inducible expression (RD29A::XERICO, 7D2A::XERICO, and DS::XERICO) remained open under these non-drought conditions.

To measure the transpiration rate of plants, detached fresh leaves were placed abaxial side up on an open petri dish and weighed at different time intervals at room temperature. Leaves of similar developmental stages (fifth true rosette leaves) from 4-week-old soil-grown plants were used. FIG. 7 graphically illustrates the percentage water loss of transgenic plants expressing XERICO driven by drought-inducible promoters compared to wild-type control plants. As shown in FIG. 7, plants expression XERICO driven by the drought-inducible promoters lost less water than did the wild type control plants (Col-0) that did not express XERICO.

To measure the chlorophyll contents of plants, fresh leaves were collected from different drought treatment condition. The leaves were sampled every three-day from the soil moisture level at a level that was nonlethal but above the wilting point (9-day-old plant).

FIG. 8 graphically illustrates the chlorophyll content of transgenic plants expressing XERICO driven by drought-inducible promoters compared to wild-type control plants. As shown in FIG. 8, plants expression XERICO driven by the drought-inducible promoters lost less chlorophyll contents than did wild type plants that did not express XERICO.

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements:
1. A nucleic acid segment comprising one or more of nucleotide sequences with at least 50% sequence identity to any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or a combination thereof, which nucleic acid segment is removed from its natural chromosomal location, and covalently linked to a heterologous nucleic acid.
2. The nucleic acid segment of statement 1, which has at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of the promoters with any of SEQ ID NO:1-12.
3. The nucleic acid segment of statement 1 or 2, wherein the heterologous nucleic acid comprises at least one coding region.
4. The nucleic acid segment of any of statements 1-3, wherein the heterologous nucleic acid comprises at least one translational initiation region.

5. The nucleic acid segment of any of statements 1-4, wherein the heterologous nucleic acid comprises at least one multi-cloning site.
6. The nucleic acid segment of any of statements 1-5, wherein the heterologous nucleic acid comprises at least one plant transcriptional termination sequence.
7. The nucleic acid segment of any of statements 1-6, wherein the heterologous nucleic acid comprises at least one plant translational termination sequence.
8. The nucleic acid segment of any of statements 1-7, wherein the heterologous nucleic acid comprises an expression cassette.
9. The nucleic acid segment of any of statements 1-8, wherein the heterologous nucleic acid comprises an expression vector.
10. The nucleic acid segment of any of statements 1-9, wherein the heterologous nucleic acid comprises an origin of replication.
11. The nucleic acid segment of any of statements 1-10, wherein the heterologous nucleic acid comprises a coding region that encodes a drought tolerance factor.
12. The nucleic acid segment of any of statements 1-11, wherein the heterologous nucleic acid comprises at least one coding region that encodes a drought tolerance factor with at least 50% amino acid sequence identity to any of SEQ ID NO:14, 16, or 18.
13. The nucleic acid segment of any of statements 1-12, wherein the heterologous nucleic acid comprises at least one coding region that encodes a drought tolerance factor that has at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of the promoters with any of amino acid sequence SEQ ID NO:14, 16, or 18.
14. The nucleic acid segment of any of statements 1-13, wherein the heterologous nucleic acid comprises at least one coding region that encodes a drought tolerance factor, where the coding region has at least 50% nucleotide sequence identity to any of SEQ ID NO:13, 15, or 17.
15. The nucleic acid segment of any of statements 1-14, wherein the heterologous nucleic acid comprises at least one coding region that encodes a drought tolerance factor, where the coding region has at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of the promoters with any of amino acid sequence SEQ ID NO:13, 15, or 17.
16. A plant cell comprising the nucleic acid segment of any of statements 1-15.
17. A plant tissue comprising the nucleic acid segment of any of statements 1-15.
18. A plant seed comprising the nucleic acid segment of any of statements 1-15.
19. A plant comprising the nucleic acid segment of any of statements 1-15.
20. The plant of statement 19, which loses at least about 1%, or at least about 2%, or at least about 3%, or at least about 4%, or at least about 5%, or at least about 6%, or at least about 7%, or at least about 8%, or at least about 9%, or at least about 10%, or at least about 12%, or at least about 15%, or at least about 20%, or at least about 30% less water under drought conditions than a plant that does not have the nucleic acid segment of any of statements 1-15.
21. The plant cell, plant tissue, plant seed, or plant of any of statements 16-20, which is a monocot.
22. The plant cell, plant tissue, plant seed, or plant of any of statements 16-21, which is a dicot.
23. The plant cell, plant tissue, plant seed, or plant of any of statements 16-22, which is a gymnosperm.
24. The plant cell, plant tissue, plant seed, or plant of any of statements 16-23, which is a plant crop species.
25. The plant cell, plant tissue, plant seed, or plant of any of statements 16-24, which is a food crop species (e.g., sugar beets, beets, tomatoes, lettuce, spinach, carrots, peppers, peas, broccoli, beans, asparagus), a legume species (e.g., peas, beans, lentils, peanuts), a fiber-containing plant species, a tree species, flax, a grain species (e.g., maize, wheat, barley, oats, rice, sorghum, millet, and rye), a grass species (e.g., switchgrass, prairie grass, wheat grass, sudangrass, sorghum, straw-producing plants), a woody plant species (e.g., a poplar species, pine species, or *eucalyptus* species), a softwood, a hardwood, an oil and/or starch producing plant species (e.g., canola, potatoes, lupins, sunflower and cottonseed), a forage plant species (e.g., alfalfa, clover, or fescue).
26. A method of producing a drought tolerant plant comprising transforming one or more plant cells with the nucleic acid segment of any of statements 1-15, and generating a plant from the one or more plant cells.
27. A method of producing a drought tolerant plant comprising expressing the nucleic acid segment of any of statements 1-15 in the plant.
28. A method of producing a drought tolerant plant comprising expressing the nucleic acid segment of any of statements 1-15 in a plant or part thereof, wherein expression of the heterologous nucleic acid produces a drought tolerance factor.
29. The method of any of statements 26-28, wherein the plant expresses a drought tolerance factor comprising at least 50% amino acid sequence identity to any of SEQ ID NO:14, 16, or 18.
30. The method of any of statements 26-29, wherein the plant expresses a drought tolerance factor comprising at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of amino acid sequences SEQ ID NO:14, 16, or 18.
31. The method of any of statements 26-30, wherein the plant expresses a drought tolerance factor from a coding region comprising at least 50% nucleotide sequence identity to any of SEQ ID NO:13, 15, or 17.
32. The method of any of statements 26-31, wherein the plant expresses a drought tolerance factor from a coding region comprising at least 55%, or at least 60%, or at least 65%, or at least 70%, or at least 75%, or at least 80%, or at least 85%, or at least 90%, or at least 95%, or at least 96%, or at least 97%, or at least 98%, or at least 99% sequence identity to any of the promoters with any of nucleotide sequences SEQ ID NO:13, 15, or 17.
33. The method of any of statements 26-32, wherein the plant is a monocot.
34. The method of any of statements 26-33, wherein the plant is a dicot.

35. The method of any of statements 26-34, wherein the plant is a gymnosperm.
36. The method of any of statements 26-35, wherein the plant is a crop species.
37. The method of any of statements 26-36, wherein the plant is a food crop species (e.g., sugar beet, beet, tomato, lettuce, spinach, carrot, pepper, pea, broccoli, bean, asparagus species), a legume species (e.g., pea, bean, lentil, peanut species), a fiber-containing plant species, a tree species, flax, a grain species (e.g., maize, wheat, barley, oats, rice, sorghum, millet, rye species), a grass species (e.g., switchgrass, prairie grass, wheat grass, sudangrass, sorghum, straw-producing plant species), a woody plant species (e.g., a poplar species, pine species, or *eucalyptus* species), a softwood, a hardwood, an oil and/or starch producing plant species (e.g., canola, potatoes, lupins, sunflower, cottonseed species), a forage plant species (e.g., alfalfa, clover, or fescue species).
38. The method of any of statements 26-37, wherein the plant loses at least about 1%, or at least about 2%, or at least about 3%, or at least about 4%, or at least about 5%, or at least about 6%, or at least about 7%, or at least about 8%, or at least about 9%, or at least about 10%, or at least about 12%, or at least about 15%, or at least about 20%, or at least about 30% less water under drought conditions than a plant that does not have the nucleic acid segment.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential.

The methods and processes illustratively described herein suitably may be practiced in differing orders of steps, and the methods and processes are not necessarily restricted to the orders of steps indicated herein or in the claims. As used herein and in the appended claims, the singular forms "a," "an," and "the" include plural reference unless the context clearly dictates otherwise. Thus, for example, a reference to "a nucleic acid" or "a promoter" includes a plurality of such nucleic acids or promoters (for example, a solution of nucleic acids or a series of promoters), and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as summarized by the statements of the invention and as defined by the appended claims.

What is claimed:

1. A plant comprising a promoter comprising SEQ ID NO: 11, wherein said promoter is operably linked to a heterologous nucleic acid.

2. The plant of claim 1, wherein the heterologous nucleic acid comprises at least one coding region.

3. The plant of claim 1, wherein the heterologous nucleic acid comprises at least one translational initiation region, at least one multi-cloning site, at least one plant transcriptional termination sequence, at least one plant translational termination sequence, or any combination thereof.

4. The plant of claim 1, wherein the plant comprises an expression cassette, or an expression vector, comprising the nucleic acid segment operably linked to the heterologous nucleic acid.

5. The plant of claim 1, wherein the heterologous nucleic acid comprises a coding region that encodes a drought tolerance factor.

6. The plant of claim 5, wherein the drought tolerance factor comprises a sequence with at least 95% amino acid sequence identity to a sequence selected from the group consisting of SEQ ID NO: 14, 16, and 18.

7. The plant of claim 5, wherein the drought tolerance factor comprises a coding region that has at least 95% nucleotide sequence identity to a sequence selected from the group consisting of SEQ ID NO: 13, 15, and 17.

8. The plant of claim 5, wherein the heterologous nucleic acid comprises at least one coding region that encodes a drought tolerance factor with at least 95% amino acid sequence identity to SEQ ID NO: 16, and wherein the plant loses over 8 hours of drought conditions at least about 5% less water than a plant that does not have the heterologous nucleic acid that encodes a drought tolerance factor.

9. The plant of claim 1, wherein the plant is a monocot, dicot, or gymnosperm.

10. The plant of claim 1, wherein the plant is a plant crop species.

11. A plant seed, a plant cell or plant tissue comprising a promoter comprising SEQ ID NO: 11, wherein said promoter operably linked to a heterologous nucleic acid.

12. The plant seed, a plant cell or plant tissue of claim 11, wherein the heterologous nucleic acid comprises a coding region that encodes a drought tolerance factor.

13. The plant seed, a plant cell or plant tissue of claim 12, wherein the drought tolerance factor comprising at least 95% amino acid sequence identity to a sequence selected from the group consisting of SEQ ID NO: 14, 16, and 18.

14. The plant seed, a plant cell or plant tissue of claim 12, wherein the drought tolerance factor comprises a coding region has at least 95% nucleotide sequence identity to a sequence selected from the group consisting of SEQ ID NO: 13, 15, and 17.

15. A method of producing a drought tolerant plant, the method comprising expressing in a plant a construct comprising nucleic acid encoding a drought tolerance factor operably linked to a heterologous a promoter comprising SEQ ID NO: 11.

16. The method of claim 15, further comprising (a) transforming one or more plant cells with the construct, and (b) generating a plant from the one or more plant cells.

17. The method of claim 15, wherein the drought tolerance factor comprises at least 95% amino acid sequence identity to a sequence selected from the group consisting of SEQ ID NO: 14, 16, and 18.

18. The method of claim 15, wherein the drought tolerance factor comprises a coding sequence comprising at least 95% nucleotide sequence identity to a sequence selected from the group consisting of SEQ ID NO: 13, 15, and 17.

19. The method of claim 15, wherein the plant is a monocot, dicot, or gymnosperm.

20. The method of claim 15, wherein the plant is a crop species.

21. The method of claim 15, wherein the plant is a food crop species, a legume species, a fiber-containing plant species, a tree species, flax, a grain species, a grass species, a woody plant species, a softwood, a hardwood, an oil producing plant species, a starch producing plant species, or a forage plant species.

22. The method of claim 15, wherein the drought tolerance factor comprises at least 95% amino acid sequence identity to SEQ ID NO: 16, and wherein the plant loses over 8 hours of drought conditions at least about 5% less water than a plant that does not comprise the construct.

* * * * *